United States Patent
Ferreira et al.

(10) Patent No.: US 12,186,378 B2
(45) Date of Patent: Jan. 7, 2025

(54) METHODS OF TREATING SKIN CANCER WITH HISTIDINE AMMONIA-LYASE (HAL) AGONISTS

(71) Applicant: Regeneron Pharmaceuticals, Inc., Tarrytown, NY (US)

(72) Inventors: Manuel Allen Revez Ferreira, Tarrytown, NY (US); Joshua Backman, Tarrytown, NY (US); Alexander Li, Tarrytown, NY (US); Michael Kessler, Tarrytown, NY (US); Eric Jorgenson, Tarrytown, NY (US); Aris Baras, Tarrytown, NY (US); Goncalo Abecasis, Tarrytown, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 62 days.

(21) Appl. No.: 17/810,816

(22) Filed: Jul. 5, 2022

(65) Prior Publication Data

US 2023/0016750 A1    Jan. 19, 2023

Related U.S. Application Data

(60) Provisional application No. 63/219,460, filed on Jul. 8, 2021.

(51) Int. Cl.
| | | |
|---|---|---|
| *A61K 38/51* | (2006.01) | |
| *A61K 31/198* | (2006.01) | |
| *A61P 35/00* | (2006.01) | |
| *C12Q 1/6869* | (2018.01) | |
| *C12Q 1/6886* | (2018.01) | |

(52) U.S. Cl.
CPC ............ *A61K 38/51* (2013.01); *A61K 31/198* (2013.01); *A61P 35/00* (2018.01); *C12Q 1/6886* (2013.01); *C12Q 1/6869* (2013.01); *C12Q 2600/156* (2013.01)

(58) Field of Classification Search
None
See application file for complete search history.

(56) References Cited

U.S. PATENT DOCUMENTS

2003/0092019 A1* 5/2003 Meyer .................. C07K 14/47
435/6.14

FOREIGN PATENT DOCUMENTS

WO     200179469     10/2001

OTHER PUBLICATIONS

Juppner (Bone 1995 vol. 17 No. 2 Supplement 39S-42S) (Year: 1995).*
Luongo et al., "The Sonic Hedgehog-Induced Type 3 Deiodinase Facilitates Tumorigenesis of Basal Cell Carcinoma by Reducing Gli2 Inactivation", Endocrinology, 2014, 155(6), pp. 2077-2088.
Welsh et al., "A role for ultraviolet radiation immunosuppression in non-melanoma skin cancer as evidenced by gene-environment interactions", Carcinogenesis, 2008, 29(10), pp. 1950-1954.
Welsh et al., "Genetic Determinants of UV-Susceptibility in Non-Melanoma Skin Cancer", PLOS ONE, 2011, 6(7), pp. e20019.
Backman et al., "Exome sequencing and analysis of 454,787 UK Biobank participants", Nature, 2021, 599(7886), pp. 628-634.

* cited by examiner

*Primary Examiner* — Katherine D Salmon
(74) *Attorney, Agent, or Firm* — Armstrong Teasdale LLP

(57) ABSTRACT

The present disclosure provides methods of treating subjects having skin cancer or at risk of developing skin cancer, and methods of identifying subjects having an increased risk of developing skin cancer.

10 Claims, 2 Drawing Sheets
Specification includes a Sequence Listing.

| Phenotype | Study | Effect (95% CI) | P-value | N cases with 0|1|2 copies of the effect allele | N controls with 0|1|2 copies of the effect allele | EAF |
|---|---|---|---|---|---|---|
| *Burden of rare pLOF and deleterious missense variants in HAL* | | | | | | |
| Vitamin D | UKB | 0.116[0.099,0.132] | 3.70E-43 | 381231|13124|27 | NA|NA|NA | 0.0167 |
| | GHS | 0.059[0.017,0.100] | 5.80E-03 | 54242|2039|1 | NA|NA|NA | 0.0181 |
| | Meta-analysis | 0.108[0.093,0.123] | 1.80E-43 | 435473|15163|28 | NA|NA|NA | 0.0169 |
| Skin tanning | UKB | 1.138[1.091,1.187] | 2.20E-09 | 86331|3244|9 | 322123|10845|18 | 0.0167 |
| | GHS | 1.230[1.020,1.483] | 3.00E-02 | 2887|123|0 | 371288|12749|25 | 0.0167 |
| | Meta-analysis | 1.244[1.106,1.399] | 2.80E-04 | 9758|426|0 | 103672|3874|2 | 0.0183 |
| Actinic keratosis | UKB | 1.240[1.122,1.370] | 2.40E-05 | 12645|549|0 | 474960|16623|27 | 0.0171 |
| | GHS | | | | | |
| | Meta-analysis | 1.136[1.062,1.216] | 2.10E-04 | 26054|996|4 | 388511|13299|23 | 0.0167 |
| Non melanoma skin cancer | UKB | 1.039[0.891,1.210] | 6.30E-01 | 5560|203|0 | 105832|3998|2 | 0.0182 |
| | GHS | 1.120[1.052,1.191] | 3.40E-04 | 31614|1204|4 | 494143|17297|25 | 0.017 |
| | Meta-analysis | 1.123[0.944,1.336] | 1.90E-01 | 3863|148|0 | 411891|14203|27 | 0.0167 |
| Melanoma skin cancer | UKB | 1.178[0.872,1.592] | 2.90E-01 | 1203|53|0 | 109815|4161|3 | 0.0183 |
| | GHS | 1.136[0.978,1.321] | 9.60E-02 | 5066|201|0 | 521706|18364|30 | 0.0171 |
| | Meta-analysis | | | | | |
| Skin color (dark olive) | UKB | 1.071[0.939,1.222] | 3.10E-01 | 6956|254|0 | 404178|13946|27 | 0.0168 |
| *GWAS sentinel variant (rs10859995-C) that is in high LD with a sentinel eQTL (rs3819817-T) that increases HAL expression in skin tissue* | | | | | | |
| Vitamin D | UKB | -0.040[-0.044,-0.035] | 3.60E-74 | 69201|192291|132890 | NA|NA|NA | 0.5808 |
| | GHS | -0.026[-0.037,-0.015] | 3.80E-06 | 11106|27942|17234 | NA|NA|NA | 0.5532 |
| | Meta-analysis | -0.038[-0.042,-0.034] | 9.00E-78 | 80307|220233|150124 | NA|NA|NA | 0.5775 |
| Skin tanning | UKB | 0.954[0.943,0.964] | 8.80E-17 | 16507|44025|29052 | 57476|162040|113470 | 0.5811 |
| | GHS | 0.988[0.947,1.029] | 5.50E-01 | 436|1113|805 | 80368|224007|155210 | 0.5814 |
| | Meta-analysis | 0.941[0.911,0.972] | 2.60E-04 | 2117|5035|3032 | 21204|53211|33133 | 0.5533 |
| Actinic keratosis | UKB | 0.951[0.924,0.978] | 4.90E-04 | 2553|6148|3837 | 101572|277218|183343 | 0.576 |
| | GHS | 0.958[0.941,0.976] | 3.40E-06 | 4995|13075|8958 | 69988|195779|135576 | 0.5812 |
| | Meta-analysis | 0.949[0.912,0.987] | 9.40E-03 | 1295|2905|1829 | 22436|56179|34883 | 0.5531 |
| Non melanoma skin cancer | UKB | 0.956[0.941,0.972] | 1.10E-07 | 6290|15980|10787 | 92424|251958|170459 | 0.5753 |
| | GHS | 0.915[0.875,0.957] | 9.80E-05 | 773|1981|1256 | 74478|207523|143801 | 0.5812 |
| | Meta-analysis | 0.928[0.857,1.004] | 6.40E-02 | 280|656|374 | 23311|58371|36150 | 0.5531 |
| Melanoma skin cancer | UKB | 0.918[0.883,0.955] | 1.70E-05 | 1053|2637|1630 | 97789|265894|179951 | 0.5754 |
| | GHS | | | | | |
| | Meta-analysis | 0.971[0.939,1.005] | 9.30E-02 | 1322|3567|2321 | 73177|203844|141130 | 0.5811 |

Figure 2

METHODS OF TREATING SKIN CANCER WITH HISTIDINE AMMONIA-LYASE (HAL) AGONISTS

REFERENCE TO SEQUENCE LISTING

This application includes a Sequence Listing submitted electronically as an XML file named 381203537SEQ220907, created on Sep. 7, 2022, with a size of 164 kilobytes. The Sequence Listing is incorporated herein by reference.

FIELD

The present disclosure relates generally to the treatment of subjects having skin cancer or at risk of developing skin cancer with Histidine Ammonia-Lyase (HAL) agonists, and methods of identifying subjects having an increased risk of developing skin cancer.

BACKGROUND

Skin cancer refers to all cancers that occur in the skin. These relatively common cancers are often mistaken by patients for non-malignant skin abnormalities, which can result in late detection that leads to difficulties in treating the disease and fatal outcomes. The most common of skin cancers is basal cell carcinoma (BCC), which accounts for about 80% of all skin cancers. Other types of skin cancers are squamous cell carcinoma (SCC), which accounts for approximately 16%, of all skin cancers, and melanoma, which accounts for about 4%. BCC and SCC are collectively referred to as non-melanoma skin cancer (NMSC). Melanoma occurs from melanocytes in the epidermis, many of which are metastatic cancers or carcinomas that lead to death. In 2000, 47,000 people were identified as having new melanomas, of which 7,700 were reported to have died (Greenlee et al., Cancer J. Clin., 2000, 50, 7-33. It is estimated that melanoma caused by ultraviolet rays is caused by intermittent exposure, such as intense tanning rather than chronic exposure to ultraviolet rays (Gilchrest et al., New Engl. J. Med., 1999, 340, 1341-1348). Another rare form of aggressive skin cancer is Merkel cell carcinoma (MCC), which is similar to melanoma.

The HAL gene encodes the enzyme histidine ammonia-lyase (or histidase) that converts histidine (an essential amino acid that is incorporated into fillaggrin, among other functions) into trans-urocanic acid, a major ultraviolet (UV)-absorbing chromophore that accumulates in the stratum corneum (Barresi et al., J. Invest. Dermatol., 2011, 131, 188-194). Inactivation of histidase is expected to decrease the ability of the outermost layer of the epidermis to block UV light.

SUMMARY

The present disclosure provides methods of treating a subject having skin cancer or at risk of developing skin cancer, the methods comprising administering a HAL agonist to the subject.

The present disclosure also provides methods of treating a subject having non-melanoma skin cancer or preventing a subject from developing non-melanoma skin cancer, the methods comprising administering a HAL agonist to the subject.

The present disclosure also provides methods of treating a subject having basal cell carcinoma or preventing a subject from developing basal cell carcinoma, the methods comprising administering a HAL agonist to the subject.

The present disclosure also provides methods of treating a subject having squamous cell carcinoma or preventing a subject from developing squamous cell carcinoma, the methods comprising administering a HAL agonist to the subject.

The present disclosure also provides methods of treating a subject having melanoma or preventing a subject from developing melanoma, the methods comprising administering a HAL agonist to the subject.

The present disclosure also provides methods of treating a subject having Merkel cell carcinoma or preventing a subject from developing Merkel cell carcinoma, the methods comprising administering a HAL agonist to the subject.

The present disclosure also provides methods of treating a subject having dermatofibrosarcoma protuberans or preventing a subject from developing dermatofibrosarcoma protuberans, the methods comprising administering a HAL agonist to the subject.

The present disclosure also provides methods of treating a subject having sebaceous carcinoma or preventing a subject from developing sebaceous carcinoma, the methods comprising administering a HAL agonist to the subject.

The present disclosure also provides methods of treating a subject with a therapeutic agent that treats or prevents skin cancer, wherein the subject has skin cancer or is at risk for developing skin cancer, the methods comprising: determining whether the subject has a HAL variant nucleic acid molecule encoding a HAL predicted gain-of-function polypeptide by: obtaining or having obtained a biological sample from the subject; and performing or having performed a sequence analysis on the biological sample to determine if the subject has a genotype comprising the HAL variant nucleic acid molecule encoding the HAL predicted gain-of-function polypeptide; and administering or continuing to administer the therapeutic agent that treats or prevents skin cancer in a standard dosage amount to a subject that is HAL reference, and/or administering a HAL agonist to the subject; and administering or continuing to administer the therapeutic agent that treats or prevents skin cancer in an amount that is the same as or less than a standard dosage amount to a subject that is heterozygous for the HAL variant nucleic acid molecule, and/or administering a HAL agonist to the subject; wherein the presence of a genotype having the HAL variant nucleic acid molecule encoding the HAL predicted gain-of-function polypeptide indicates the subject has a decreased risk of developing skin cancer.

The present disclosure also provides methods of identifying a subject having an increased risk of developing skin cancer, the methods comprising: determining or having determined the presence or absence of a HAL variant nucleic acid molecule encoding a HAL predicted gain-of-function polypeptide in a biological sample obtained from the subject; wherein: when the subject is HAL reference, then the subject has an increased risk of developing skin cancer; and when the subject is heterozygous or homozygous for a HAL variant nucleic acid molecule encoding the HAL predicted gain-of-function polypeptide, then the subject has a decreased risk of developing skin cancer.

The present disclosure also provides therapeutic agents that treat or prevent skin cancer for use in the treatment or prevention of skin cancer in a subject identified as having a genomic nucleic acid molecule encoding a HAL predicted gain-of-function polypeptide, or the complement thereof, wherein the genomic nucleic acid molecule has a nucleotide sequence comprising: i) an adenine at a position corresponding to position 11,352 according to SEQ ID NO:2, or the complement thereof; or ii) a guanine at a position corresponding to position 14,441 according to SEQ ID NO:3, or the complement thereof.

The present disclosure also provides HAL agonists for use in the treatment or prevention of skin cancer in a subject that: a) is reference for a HAL genomic nucleic acid molecule, a HAL mRNA molecule, or a HAL cDNA molecule; or b) is heterozygous for a genomic nucleic acid molecule encoding a HAL predicted gain-of-function polypeptide, or the complement thereof, wherein the genomic nucleic acid molecule has a nucleotide sequence comprising: i) an adenine at a position corresponding to position 11,352 according to SEQ ID NO:2, or the complement thereof; or ii) a guanine at a position corresponding to position 14,441 according to SEQ ID NO:3, or the complement thereof.

BRIEF DESCRIPTION OF THE DRAWINGS

The accompanying figures, which are incorporated in and constitute a part of this specification, illustrate several features of the present disclosure.

FIG. 2 shows an association between non-coding variants in HAL and vitamin D levels and skin cancer-related traits.

DESCRIPTION

Figure 1:
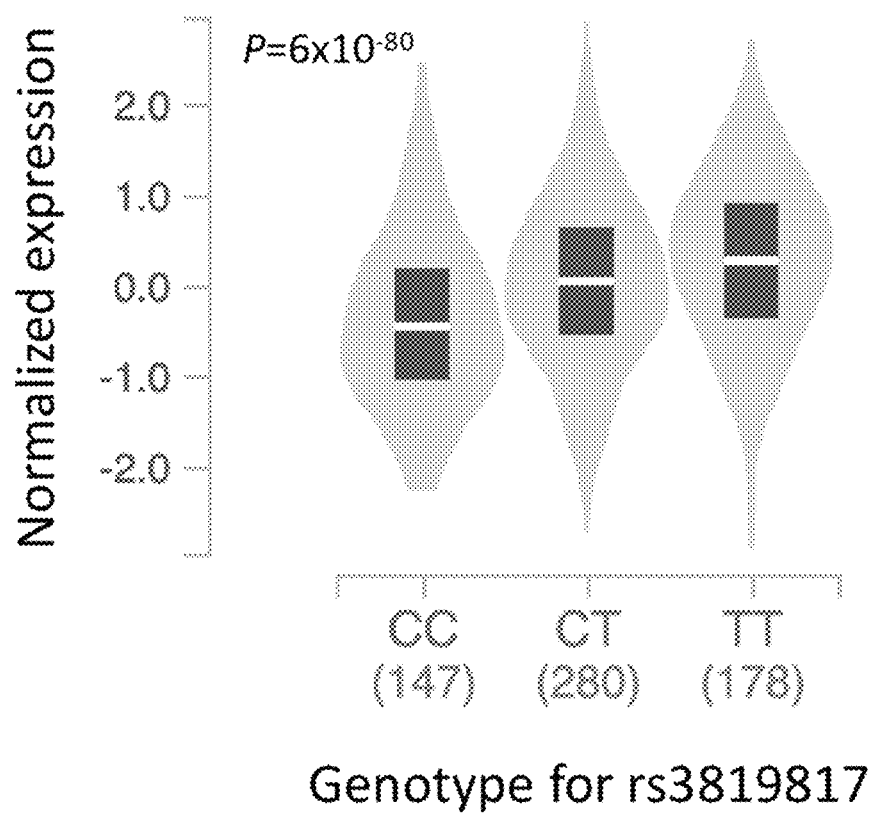
FIG. 1 shows an association between a non-coding variant in HAL and gene expression in skin tissue (sun exposed—lower leg) from GTEx.

Various terms relating to aspects of the present disclosure are used throughout the specification and claims. Such terms are to be given their ordinary meaning in the art, unless otherwise indicated. Other specifically defined terms are to be construed in a manner consistent with the definitions provided herein.

Unless otherwise expressly stated, it is not intended that any method or aspect set forth herein be construed as requiring that its steps be performed in a specific order. Accordingly, where a method claim does not specifically state in the claims or descriptions that the steps are to be limited to a specific order, it is not intended that an order be inferred, in any respect. This holds for any possible non-expressed basis for interpretation, including matters of logic with respect to arrangement of steps or operational flow, plain meaning derived from grammatical organization or punctuation, or the number or type of aspects described in the specification.

As used herein, the singular forms "a," "an" and "the" include plural referents unless the context clearly dictates otherwise.

As used herein, the term "about" means that the recited numerical value is approximate and small variations would not significantly affect the practice of the disclosed embodiments. Where a numerical value is used, unless indicated otherwise by the context, the term "about" means the numerical value can vary by ±10% and remain within the scope of the disclosed embodiments.

As used herein, the term "comprising" may be replaced with "consisting" or "consisting essentially of" in particular embodiments as desired.

As used herein, the term "isolated", in regard to a nucleic acid molecule or a polypeptide, means that the nucleic acid molecule or polypeptide is in a condition other than its native environment, such as apart from blood and/or other tissue. In some embodiments, an isolated nucleic acid molecule or polypeptide is substantially free of other nucleic acid molecules or other polypeptides, particularly other nucleic acid molecules or polypeptides of animal origin. In some embodiments, the nucleic acid molecule or polypeptide can be in a highly purified form, i.e., greater than 95% pure or greater than 99% pure. When used in this context, the term "isolated" does not exclude the presence of the same nucleic acid molecule or polypeptide in alternative physical forms, such as dimers or alternatively phosphorylated or derivatized forms.

As used herein, the terms "nucleic acid", "nucleic acid molecule", "nucleic acid sequence", "polynucleotide", or "oligonucleotide" can comprise a polymeric form of nucleotides of any length, can comprise DNA and/or RNA, and can be single-stranded, double-stranded, or multiple stranded. One strand of a nucleic acid also refers to its complement.

As used herein, the term "subject" includes any animal, including mammals. Mammals include, but are not limited to, farm animals (such as, for example, horse, cow, pig), companion animals (such as, for example, dog, cat), laboratory animals (such as, for example, mouse, rat, rabbits), and non-human primates (such as, for example, apes and monkeys). In some embodiments, the subject is a human. In some embodiments, the subject is a patient under the care of a physician.

A burden of common putative gain-of-function (GOF) in the HAL gene associated with a decreased risk of developing skin cancer in humans has been identified in accordance with the present disclosure. For example, a genetic alteration that changes the guanine at position 11,352 in the HAL reference genomic nucleic acid molecule (see, SEQ ID NO:1) to an adenine or changes the adenine at position 14,441 in the HAL reference genomic nucleic acid molecule to a guanine, has been observed to indicate that the subject having such an alteration may have a decreased risk of developing skin cancer. Altogether, the genetic analyses described herein surprisingly indicate that the HAL gene and, in particular, pGOFs in the HAL gene, associates with a decreased risk of developing skin cancer. Therefore, subjects that are HAL reference that have an increased risk of developing skin cancer, such as non-melanoma skin cancer, basal cell carcinoma, squamous cell carcinoma, melanoma, Merkel cell carcinoma, dermatofibrosarcoma protuberans, or sebaceous carcinoma, may be treated such that the skin cancer is prevented, the symptoms thereof are reduced, and/or development of symptoms is repressed. Accordingly, the present disclosure provides methods of leveraging the identification of such variants in subjects to identify or stratify risk in such subjects of developing skin cancer, such as non-melanoma skin cancer, basal cell carcinoma, squamous cell carcinoma, melanoma, Merkel cell carcinoma, dermatofibrosarcoma protuberans, or sebaceous carcinoma, or to diagnose subjects as having an increased risk of developing skin cancer, such as non-melanoma skin cancer, basal cell carcinoma, squamous cell carcinoma, melanoma, Merkel cell carcinoma, dermatofibrosarcoma protuberans, or sebaceous carcinoma, such that subjects at risk or subjects with active disease may be treated accordingly.

It has been further observed in accordance with the present disclosure that HAL variant nucleic acid molecules encoding a HAL predicted gain-of-function polypeptide (whether these variations are homozygous or heterozygous in a particular subject) associate with a decreased risk of developing skin cancer. Moreover, the identification by the present disclosure of the association between additional variants and gene burden masks indicates that HAL may be responsible for a protective effect in skin cancer.

For purposes of the present disclosure, any particular subject can be categorized as having one of three HAL genotypes: i) HAL reference; ii) heterozygous for a HAL variant nucleic acid molecule encoding a HAL predicted gain-of-function polypeptide; or iii) homozygous for a HAL variant nucleic acid molecule encoding a HAL predicted gain-of-function polypeptide. A subject is HAL reference when the subject does not have a copy of a HAL variant nucleic acid molecule encoding a HAL predicted gain-of-function polypeptide. A subject is heterozygous for a HAL variant nucleic acid molecule encoding a HAL predicted gain-of-function polypeptide when the subject has a single copy of a HAL variant nucleic acid molecule. As used herein, a HAL variant nucleic acid molecule is any HAL nucleic acid molecule (such as, a genomic nucleic acid molecule, an mRNA molecule, or a cDNA molecule) encoding a HAL polypeptide having a partial gain-of-function, a complete gain-of-function, a predicted partial gain-of-function, or a predicted complete gain-of-function. A subject who has a HAL variant nucleic acid molecule encoding a HAL predicted gain-of-function polypeptide having a partial gain-of-function (or predicted partial gain-of-function) is hypomorphic for HAL. A subject is homozygous for a HAL variant nucleic acid molecule encoding a HAL predicted gain-of-function polypeptide when the subject has two copies of a HAL variant nucleic acid molecule encoding a HAL predicted gain-of-function polypeptide.

For subjects that are genotyped or determined to be HAL reference, such subjects have an increased risk of developing skin cancer, such as non-melanoma skin cancer, basal cell carcinoma, squamous cell carcinoma, melanoma, Merkel cell carcinoma, dermatofibrosarcoma protuberans, and/or sebaceous carcinoma. For subjects that are genotyped or determined to be either HAL reference or heterozygous for a HAL variant nucleic acid molecule encoding a HAL predicted gain-of-function polypeptide, such subjects can be treated with a HAL agonist.

In any of the embodiments described throughout the present disclosure, the HAL variant nucleic acid molecule can be any HAL nucleic acid molecule (such as, for example, genomic nucleic acid molecule, mRNA molecule, or cDNA molecule) encoding a HAL polypeptide having a partial gain-of-function, a complete gain-of-function, a predicted partial gain-of-function, or a predicted complete gain-of-function.

In any of the embodiments described throughout the present disclosure, the HAL predicted gain-of-function polypeptide can be any HAL polypeptide having a partial gain-of-function, a complete gain-of-function, a predicted partial gain-of-function, or a predicted complete gain-of-function.

Any one or more (i.e., any combination) of the HAL variant nucleic acid molecules encoding a HAL predicted gain-of-function polypeptide can be used within any of the methods described herein to determine whether a subject has an increased risk of developing skin cancer. The combinations of particular variants can form a mask used for statistical analysis of the particular correlation of HAL and decreased risk of developing skin cancer.

In any of the embodiments described throughout the present disclosure, the skin cancer is non-melanoma skin cancer, basal cell carcinoma, squamous cell carcinoma, melanoma, Merkel cell carcinoma, dermatofibrosarcoma protuberans, or sebaceous carcinoma. In any of the embodiments described throughout the present disclosure, the skin cancer is non-melanoma skin cancer. In any of the embodiments described throughout the present disclosure, the skin cancer is basal cell carcinoma. In any of the embodiments described throughout the present disclosure, the skin cancer is squamous cell carcinoma. In any of the embodiments described throughout the present disclosure, the skin cancer is melanoma. In any of the embodiments described throughout the present disclosure, the skin cancer is Merkel cell carcinoma. In any of the embodiments described throughout the present disclosure, the skin cancer is dermatofibrosarcoma protuberans. In any of the embodiments described throughout the present disclosure, the skin cancer is sebaceous carcinoma.

Symptoms of basal cell carcinoma include, but are not limited to, a raised, smooth, pearly bump on the sun-exposed skin of an individual's head, neck or shoulders. Often small blood vessels can be seen within the tumor. Crusting of the tumor, as well as bleeding can occur. Individuals sometimes mistake basal cell carcinoma as a sore that will not heal. Basal cell carcinoma is the least deadly form of skin cancer and often times with proper treatment can be completely eliminated.

Symptoms of squamous cell carcinoma include, but are not limited to a red, scaling, thickened patch on the sun exposed skin of an individual. Some forms of squamous cell carcinoma appear as firm hard nodules and as dome shapes. Breaks and bleeding of the nodules may occur. If left untreated, the squamous cell carcinoma could develop into a large mass. Squamous cell carcinoma is the second most common form of skin cancer.

Symptoms of melanoma include, but are not limited to, shades or brown to black lesions. There are also some melanomas which appear pink, red or flesh color, these are called amelanotic melanomas. The amelanotic melanomas are a more aggressive form of melanoma. Some of the warning signs of malignant melanoma could include changes in size, shape, color, elevation of a mole, the development of a new mole in the transitional period from puberty to adulthood, itching, ulceration or bleeding. Melanoma is the most deadly form of skin cancer.

Symptoms of Merkel cell carcinoma include, but are not limited to rapid growing, non-tender flesh colored to red/violet bumps that are usually not painful or itchy. These bumps appear on the highly sun exposed skin of the head, neck and arms. Individuals often mistake Merkel cell carcinoma for a cyst or other type of cancer.

Symptoms of dermatofibrosarcoma protuberans include, but are not limited to small, slightly-raised, red or purple patch of skin 1 to 5 centimeters wide that can become a raised nodule and in some cases may cause redness, open up or bleed.

Symptoms of sebaceous carcinoma include, but are not limited to slow-growing sometimes yellow painless lump at an eyelid. The bump may bleed or ooze and may also have a thickening or yellow or reddish crust, where the eyelid meets the lash.

The present disclosure provides methods of treating a subject having skin cancer or at risk of developing skin cancer, the methods comprising administering a HAL agonist to the subject.

The present disclosure also provides methods of treating a subject having non-melanoma skin cancer or at risk of developing non-melanoma skin cancer, the methods comprising administering a HAL agonist to the subject.

The present disclosure also provides methods of treating a subject having basal cell carcinoma or at risk of developing basal cell carcinoma, the methods comprising administering a HAL agonist to the subject.

The present disclosure also provides methods of treating a subject having squamous cell carcinoma or at risk of developing squamous cell carcinoma, the methods comprising administering a HAL agonist to the subject.

The present disclosure also provides methods of treating a subject having melanoma or at risk of developing melanoma, the methods comprising administering a HAL agonist to the subject.

The present disclosure also provides methods of treating a subject having Merkel cell carcinoma or at risk of developing Merkel cell carcinoma, the methods comprising administering a HAL agonist to the subject.

The present disclosure also provides methods of treating a subject having dermatofibrosarcoma protuberans or at risk of developing dermatofibrosarcoma protuberans, the methods comprising administering a HAL agonist to the subject.

The present disclosure also provides methods of treating a subject having sebaceous carcinoma or at risk of developing sebaceous carcinoma, the methods comprising administering a HAL agonist to the subject.

In some embodiments, the HAL agonist is HAL protein, or a functionally active fragment thereof, or thyroid hormone ($T_3$).

In some embodiments, the methods of treatment further comprise detecting the presence or absence of a HAL variant nucleic acid molecule encoding a HAL predicted gain-of-function polypeptide in a biological sample obtained from the subject. As used throughout the present disclosure, "a HAL variant nucleic acid molecule" is any HAL nucleic acid molecule (such as, for example, genomic nucleic acid molecule, mRNA molecule, or cDNA molecule) encoding a HAL polypeptide having a partial gain-of-function, a complete gain-of-function, a predicted partial gain-of-function, or a predicted complete gain-of-function.

The present disclosure also provides methods of treating a subject with a therapeutic agent that treats or prevents skin cancer. In some embodiments, the subject has skin cancer. In some embodiments, the subject is at risk of developing skin cancer. In some embodiments, the methods comprise determining whether the subject has a HAL variant nucleic acid molecule encoding a HAL predicted gain-of-function polypeptide by obtaining or having obtained a biological sample obtained from the subject, and performing or having performed a sequence analysis on the biological sample to determine if the subject has a genotype comprising the HAL variant nucleic acid molecule. When the subject is HAL reference, the therapeutic agent that treats or prevents skin cancer is administered or continued to be administered to the subject in a standard dosage amount, and/or a HAL agonist is administered to the subject. When the subject is heterozygous for a HAL variant, the therapeutic agent that treats or prevents skin cancer is administered or continued to be administered to the subject in an amount that is the same as or less than a standard dosage amount, and/or a HAL agonist is administered to the subject. The presence of a genotype having the HAL variant nucleic acid molecule encoding the HAL predicted gain-of-function polypeptide indicates the subject has a decreased risk of developing skin cancer. In some embodiments, the subject is HAL reference. In some embodiments, the subject is heterozygous for the HAL variant nucleic acid molecule encoding a HAL predicted gain-of-function polypeptide.

For subjects that are genotyped or determined to be either HAL reference or heterozygous for a HAL variant nucleic acid molecule encoding a HAL predicted gain-of-function polypeptide, such subjects can be treated with a HAL agonist, as described herein.

Detecting the presence or absence of a HAL variant nucleic acid molecule encoding a HAL predicted gain-of-function polypeptide in a biological sample obtained from a subject and/or determining whether a subject has a HAL variant nucleic acid molecule encoding a HAL predicted gain-of-function polypeptide can be carried out by any of the methods described herein. In some embodiments, these methods can be carried out in vitro. In some embodiments, these methods can be carried out in situ. In some embodiments, these methods can be carried out in vivo. In any of these embodiments, the HAL variant nucleic acid molecule encoding a HAL predicted gain-of-function polypeptide can be present within a cell obtained from the subject.

In some embodiments, when the subject is HAL reference, the subject is also administered a therapeutic agent that treats or prevents skin cancer in a standard dosage amount. In some embodiments, when the subject is heterozygous for a HAL variant nucleic acid molecule encoding a HAL predicted gain-of-function polypeptide, the subject is administered a therapeutic agent that treats or prevents skin cancer in a dosage amount that is the same as or less than a standard dosage amount.

In some embodiments, the treatment methods further comprise detecting the presence or absence of a HAL predicted gain-of-function polypeptide in a biological sample obtained from the subject. In some embodiments, when the subject does not have a HAL predicted gain-of-function polypeptide, the subject is administered a therapeutic agent that treats or prevents skin cancer in a standard dosage amount. In some embodiments, when the subject has a HAL predicted gain-of-function polypeptide, the subject is administered a therapeutic agent that treats or prevents skin cancer in a dosage amount that is the same as or less than a standard dosage amount.

The present disclosure also provides methods of treating a subject with a therapeutic agent that treats or prevents skin cancer. In some embodiments, the subject has skin cancer. In some embodiments, the subject is at risk of developing skin cancer. In some embodiments, the methods comprise determining whether the subject has a HAL predicted gain-of-function polypeptide by obtaining or having obtained a biological sample from the subject, and performing or having performed an assay on the biological sample to determine if the subject has a HAL predicted gain-of-function polypeptide. When the subject does not have a HAL predicted gain-of-function polypeptide, the therapeutic agent that treats or prevents skin cancer is administered or continued to be administered to the subject in a standard dosage amount, and/or a HAL agonist is administered to the subject. When the subject has a HAL predicted gain-of-function polypeptide, the therapeutic agent that treats or prevents skin cancer is administered or continued to be administered to the subject in an amount that is the same as or less than a standard dosage amount, and/or a HAL agonist is administered to the subject. The presence of a HAL predicted gain-of-function polypeptide indicates the subject has a decreased risk of developing skin cancer. In some embodiments, the subject has a HAL predicted gain-of-function polypeptide. In some embodiments, the subject does not have a HAL predicted gain-of-function polypeptide.

Detecting the presence or absence of a HAL predicted gain-of-function polypeptide in a biological sample obtained from a subject and/or determining whether a subject has a HAL predicted gain-of-function polypeptide can be carried out by any of the methods described herein. In some embodiments, these methods can be carried out in vitro. In some embodiments, these methods can be carried out in situ. In some embodiments, these methods can be carried out in vivo. In any of these embodiments, the HAL predicted gain-of-function polypeptide can be present within a cell obtained from the subject.

Examples of therapeutic agents that treat or prevent skin cancer include, but are not limited to: thiazide diuretics (such as, chlorthalidone, chlorothiazide, hydrochlorothiazide, indapamide, or metolazone); potassium-sparing diuretics (such as, amiloride, spironolactone, or triamterene); loop diuretics (such as, bumetanide, furosemide, or torsemide); beta blockers (such as, acebutolol, atenolol, betaxolol, bisoprolol, bisoprolol/hydrochlorothiazide, metoprolol tartrate, metoprolol succinate, nadolol, pindolol, propranolol, solotol, or timolol); angiotensin converting enzyme (ACE) agonists (such as, benazepril, captopril, enalapril, fosinopril, lisinopril, moexipril, perindopril, quinapril, ramipril, or trandolapril); angiotensin II receptor blockers (ARBs) (such as, candesartan, eprosartan, irbesartan, losartan, telmisartan, or valsartan); calcium channel blockers (such as, amlodipine, diltiazem, felodipine, isradipine, nicardipine, nifedipine, nisoldipine, or verapamil); alpha-blockers (such as, doxazosin, prazosin, or terazosin); alpha-beta-blockers (such as carvedilol or labetalol); central agonists (such as, methyldopa, clonidine, or guanfacine); vasodilators (such as, hydralazine or minoxidil); aldosterone receptor antagonists (such as, eplerenone or spironolactone), and renin agonists (such as aliskiren).

In some embodiments, the therapeutic agent that treats or prevents skin cancer is a thiazide diuretic, a potassium-sparing diuretic, a loop diuretic, a beta blocker, an ACE inhibitor, an ARB, a calcium channel blocker, an alpha-blocker, an alpha-beta-blocker, a central agonist, a vasodilator, an aldosterone receptor antagonist, or a renin inhibitor. In some embodiments, the thiazide diuretic is chlorthalidone, chlorothiazide, hydrochlorothiazide, indapamide, or metolazone. In some embodiments, the potassium-sparing diuretic is amiloride, spironolactone, or triamterene. In some embodiments, the loop diuretic is bumetanide, furosemide, or torsemide. In some embodiments, the beta blocker is acebutolol, atenolol, betaxolol, bisoprolol, bisoprolol/hydrochlorothiazide, metoprolol tartrate, metoprolol succinate, nadolol, pindolol, propranolol, solotol, or timolol). In some embodiments, the ACE inhibitor is benazepril, captopril, enalapril, fosinopril, lisinopril, moexipril, perindopril, quinapril, ramipril, or trandolapril. In some embodiments, the ARB is candesartan, eprosartan, irbesartan, losartan, telmisartan, or valsartan. In some embodiments, the calcium channel blocker is amlodipine, diltiazem, felodipine, isradipine, nicardipine, nifedipine, nisoldipine, or verapamil. In some embodiments, the alpha-blocker is doxazosin, prazosin, or terazosin. In some embodiments, the alpha-beta-blocker is carvedilol or labetalol. In some embodiments, the central agonist is methyldopa, clonidine, or guanfacine). In some embodiments, the vasodilator is hydralazine or minoxidil. In some embodiments, the aldosterone receptor antagonist is eplerenone or spironolactone. In some embodiments, the renin inhibitor is aliskiren.

In some embodiments, the dose of the therapeutic agents that treat or prevent skin cancer can be reduced by about 10%, by about 20%, by about 30%, by about 40%, by about 50%, by about 60%, by about 70%, by about 80%, or by about 90% for subjects that are heterozygous for a HAL variant nucleic acid molecule encoding a HAL predicted gain-of-function polypeptide (i.e., less than the standard dosage amount) compared to subjects that are HAL reference (who may receive a standard dosage amount). In some embodiments, the dose of the therapeutic agents that treat or prevent skin cancer can be reduced by about 10%, by about 20%, by about 30%, by about 40%, or by about 50%. In addition, the dose of therapeutic agents that treat or prevent skin cancer in subjects that are heterozygous for a HAL variant nucleic acid molecule encoding a HAL predicted gain-of-function polypeptide can be administered less frequently compared to subjects that are HAL reference.

Administration of the therapeutic agents that treat or prevent skin cancer and/or HAL agonists can be repeated, for example, after one day, two days, three days, five days, one week, two weeks, three weeks, one month, five weeks, six weeks, seven weeks, eight weeks, two months, or three months. The repeated administration can be at the same dose or at a different dose. The administration can be repeated once, twice, three times, four times, five times, six times, seven times, eight times, nine times, ten times, or more. For example, according to certain dosage regimens a subject can receive therapy for a prolonged period of time such as, for example, 6 months, 1 year, or more. In addition, the therapeutic agents that treat or prevent skin cancer and/or HAL agonists can be administered sequentially or at the same time. In addition, the therapeutic agents that treat or prevent skin cancer and/or HAL agonists can be administered in separate compositions or can be administered together in the same composition.

Administration of the therapeutic agents that treat or prevent skin cancer and/or HAL agonists can occur by any suitable route including, but not limited to, parenteral, intravenous, oral, subcutaneous, intra-arterial, intracranial, intrathecal, intraperitoneal, topical, intranasal, or intramuscular. Pharmaceutical compositions for administration are desirably sterile and substantially isotonic and manufactured under GMP conditions. Pharmaceutical compositions can be provided in unit dosage form (i.e., the dosage for a single administration). Pharmaceutical compositions can be formulated using one or more physiologically and pharmaceutically acceptable carriers, diluents, excipients or auxiliaries. The formulation depends on the route of administration chosen. The term "pharmaceutically acceptable" means that the carrier, diluent, excipient, or auxiliary is compatible with the other ingredients of the formulation and not substantially deleterious to the recipient thereof.

The terms "treat", "treating", and "treatment" and "prevent", "preventing", and "prevention" as used herein, refer to eliciting the desired biological response, such as a therapeutic and prophylactic effect, respectively. In some embodiments, a therapeutic effect comprises one or more of a decrease/reduction in skin cancer, a decrease/reduction in the severity of skin cancer (such as, for example, a reduction or inhibition of development of skin cancer), a decrease/reduction in symptoms and skin cancer-related effects, delaying the onset of symptoms and skin cancer-related effects, reducing the severity of symptoms of skin cancer-related effects, reducing the severity of an acute episode, reducing the number of symptoms and skin cancer-related effects, reducing the latency of symptoms and skin cancer-related effects, an amelioration of symptoms and skin cancer-related effects, reducing secondary symptoms, reducing secondary infections, preventing relapse to skin cancer, decreasing the number or frequency of relapse episodes, increasing latency between symptomatic episodes, increasing time to sustained progression, expediting remission, inducing remission, augmenting remission, speeding recovery, or increasing efficacy of or decreasing resistance to alternative therapeutics, and/or an increased survival time of the affected host animal, following administration of the agent or composition comprising the agent. A prophylactic effect may comprise a complete or partial avoidance/inhibition or a delay of skin cancer development/progression (such as, for example, a complete or partial avoidance/inhibition or a delay), and an increased survival time of the affected host animal, following administration of a therapeutic protocol. Treatment of skin cancer encompasses the treatment of subjects already diagnosed as having any form of skin cancer at any clinical stage or manifestation, the delay of the onset or evolution or aggravation or deterioration of the symptoms or signs of skin cancer, and/or preventing and/or reducing the severity of skin cancer.

The present disclosure also provides methods of identifying a subject having an increased risk of developing skin cancer. In some embodiments, the methods comprise determining or having determined the presence or absence of a HAL variant nucleic acid molecule (such as a genomic nucleic acid molecule, mRNA molecule, and/or cDNA molecule) encoding a HAL predicted gain-of-function polypeptide in a biological sample obtained from the subject. When the subject lacks a HAL variant nucleic acid molecule encoding a HAL predicted gain-of-function polypeptide (i.e., the subject is genotypically categorized as HAL reference), then the subject has an increased risk of developing skin cancer. When the subject has a HAL variant nucleic acid molecule encoding a HAL predicted gain-of-function polypeptide (i.e., the subject is heterozygous or homozygous for a HAL variant nucleic acid molecule), then the subject has a decreased risk of developing skin cancer compared to a subject that is HAL reference.

Having a single copy of a HAL variant nucleic acid molecule encoding a HAL predicted gain-of-function polypeptide is more protective of a subject from developing skin cancer than having no copies of a HAL variant nucleic acid molecule encoding a HAL predicted gain-of-function polypeptide. Without intending to be limited to any particular theory or mechanism of action, it is believed that a single copy of a HAL variant nucleic acid molecule (i.e., heterozygous for a HAL variant nucleic acid molecule) is protective of a subject from developing skin cancer, and it is also believed that having two copies of a HAL variant nucleic acid molecule encoding a HAL predicted gain-of-function polypeptide (i.e., homozygous for a HAL variant nucleic acid molecule) may be more protective of a subject from developing skin cancer, relative to a subject with a single copy. Thus, in some embodiments, a single copy of a HAL variant nucleic acid molecule encoding a HAL predicted gain-of-function polypeptide may not be completely protective, but instead, may be partially or incompletely protective of a subject from developing skin cancer. While not desiring to be bound by any particular theory, there may be additional factors or molecules involved in the development of skin cancer that are still present in a subject having a single copy of a HAL variant nucleic acid molecule encoding a HAL predicted gain-of-function polypeptide, thus resulting in less than complete protection from the development of skin cancer.

Detecting the presence or absence of a HAL variant nucleic acid molecule encoding a HAL predicted gain-of-function polypeptide in a biological sample obtained from a subject and/or determining whether a subject has a HAL variant nucleic acid molecule encoding a HAL predicted gain-of-function polypeptide can be carried out by any of the methods described herein. In some embodiments, these methods can be carried out in vitro. In some embodiments, these methods can be carried out in situ. In some embodiments, these methods can be carried out in vivo. In any of these embodiments, the HAL variant nucleic acid molecule encoding a HAL predicted gain-of-function polypeptide can be present within a cell obtained from the subject.

In some embodiments, when a subject is identified as having an increased risk of developing skin cancer, the subject is further treated with a therapeutic agent that treats or prevents skin cancer and/or a HAL agonist, as described herein. For example, when the subject is HAL reference, and therefore has an increased risk for developing skin cancer, the subject is administered a HAL agonist. In some embodiments, such a subject is also administered a therapeutic agent that treats or prevents skin cancer. In some embodiments, when the subject is heterozygous for a HAL variant nucleic acid molecule encoding a HAL predicted gain-of-function polypeptide, the subject is administered the therapeutic agent that treats or prevents skin cancer in a dosage amount that is the same as or less than a standard dosage amount, and/or is administered a HAL agonist. In some embodiments, the subject is HAL reference. In some embodiments, the subject is heterozygous for a HAL variant nucleic acid molecule encoding a HAL predicted gain-of-function polypeptide.

In some embodiments, any of the methods described herein can further comprise determining the subject's aggregate burden of having a HAL variant nucleic acid molecule encoding a HAL predicted gain-of-function polypeptide, and/or a HAL predicted gain-of-function variant polypeptide associated with a decreased risk of developing skin cancer. The aggregate burden is the aggregate of all variants in the HAL gene, which can be carried out in an association analysis with skin cancer. In some embodiments, the subject is homozygous for one or more HAL variant nucleic acid molecules encoding a HAL predicted gain-of-function polypeptide associated with a decreased risk of developing skin cancer. In some embodiments, the subject is heterozygous for one or more HAL variant nucleic acid molecules encoding a HAL predicted gain-of-function polypeptide associated with a decreased risk of developing skin cancer. The result of the association analysis suggests that HAL variant nucleic acid molecules encoding a HAL predicted gain-of-function polypeptide are associated with decreased risk of developing skin cancer. When the subject has a lower aggregate burden, the subject is at a higher risk of developing skin cancer and the subject is administered or continued to be administered the therapeutic agent that treats or prevents skin cancer in a standard dosage amount, and/or a HAL agonist. When the subject has a greater aggregate burden, the subject is at a lower risk of developing skin cancer and the subject is administered or continued to be administered the therapeutic agent that treats or prevents skin cancer in an amount that is the same as or less than the standard dosage amount. The greater the aggregate burden, the lower the risk of developing skin cancer.

HAL variants that can be used in the aggregate burden analysis include any one or more, or any combination, of the following Table 1:

TABLE 1

| Variant | rsID |
|---|---|
| 12:95980972:G:A | rs2270318 |
| 12:95981904:T:C | rs10859995 |
| 12:95984993:C:T | rs3819817 |
| 12:95986028:G:A | rs3213737 |

In some embodiments, the subject's aggregate burden of having any one or more HAL variant nucleic acid molecules encoding a HAL predicted gain-of-function polypeptide represents a weighted aggregate of a plurality of any of the HAL variant nucleic acid molecules encoding a HAL predicted gain-of-function polypeptide. In some embodiments, the aggregate burden is calculated using at least about 2, at least about 3, at least about 4, at least about 5, at least about 10, at least about 20, at least about 30, at least about 40, at least about 50, at least about 60, at least about 70, at least about 80, at least about 100, at least about 120, at least about 150, at least about 200, at least about 250, at least about 300, at least about 400, at least about 500, at least about 1,000, at least about 10,000, at least about 100,000, or at least about or more than 1,000,000 genetic variants present in or around (up to 10 Mb) the HAL gene where the genetic burden is the number of alleles multiplied by the association estimate with skin cancer or related outcome for each allele (e.g., a weighted polygenic burden score). This can include any genetic variants, regardless of their genomic annotation, in proximity to the HAL gene (up to 10 Mb around the gene) that show a non-zero association with skin cancer-related traits in a genetic association analysis. In some embodiments, when the subject has an aggregate burden above a desired threshold score, the subject has a decreased risk of developing skin cancer. In some embodiments, when the subject has an aggregate burden below a desired threshold score, the subject has an increased risk of developing skin cancer.

In some embodiments, the aggregate burden may be divided into quintiles, e.g., top quintile, intermediate quintile, and bottom quintile, wherein the top quintile of aggregate burden corresponds to the lowest risk group and the bottom quintile of aggregate burden corresponds to the highest risk group. In some embodiments, a subject having a greater aggregate burden comprises the highest weighted aggregate burdens, including, but not limited to the top 10%, top 20%, top 30%, top 40%, or top 50% of aggregate burdens from a subject population. In some embodiments, the genetic variants comprise the genetic variants having association with skin cancer in the top 10%, top 20%, top 30%, top 40%, or top 50% of p-value range for the association. In some embodiments, each of the identified genetic variants comprise the genetic variants having association with skin cancer with p-value of no more than about $10^{-2}$, about $10^{-3}$, about $10^{-4}$, about $10^{-5}$, about $10^{-6}$, about $10^{-7}$, about $10^{-8}$, about $10^{-9}$, about $10^{-10}$, about $10^{-11}$, about $10^{-12}$, about $10^{-13}$, about $10^{-14}$, about or $10^{-15}$. In some embodiments, the identified genetic variants comprise the genetic variants having association with skin cancer with p-value of less than $5 \times 10^{-8}$. In some embodiments, the identified genetic variants comprise genetic variants having association with skin cancer in high-risk subjects as compared to the rest of the reference population with odds ratio (OR) about 1.5 or greater, about 1.75 or greater, about 2.0 or greater, or about 2.25 or greater for the top 20% of the distribution; or about 1.5 or greater, about 1.75 or greater, about 2.0 or greater, about 2.25 or greater, about 2.5 or greater, or about 2.75 or greater. In some embodiments, the odds ratio (OR) may range from about 1.0 to about 1.5, from about 1.5 to about 2.0, from about 2.0 to about 2.5, from about 2.5 to about 3.0, from about 3.0 to about 3.5, from about 3.5 to about 4.0, from about 4.0 to about 4.5, from about 4.5 to about 5.0, from about 5.0 to about 5.5, from about 5.5 to about 6.0, from about 6.0 to about 6.5, from about 6.5 to about 7.0, or greater than 7.0. In some embodiments, high-risk subjects comprise subjects having aggregate burdens in the bottom decile, quintile, or tertile in a reference population. The threshold of the aggregate burden is determined on the basis of the nature of the intended practical application and the risk difference that would be considered meaningful for that practical application.

In some embodiments, when a subject is identified as having an increased risk of developing skin cancer, the subject is further administered a therapeutic agent that treats or prevents skin cancer, and/or a HAL agonist, as described herein. For example, when the subject is HAL reference, and therefore has an increased risk of developing skin cancer, the subject is administered a HAL agonist. In some embodiments, such a subject is also administered a therapeutic agent that treats or prevents skin cancer. In some embodiments, when the subject is heterozygous for a HAL variant nucleic acid molecule encoding a HAL predicted gain-of-function polypeptide, the subject is administered the therapeutic agent that treats or prevents skin cancer in a dosage amount that is the same as or less than a standard dosage amount, and/or is administered a HAL agonist. In some embodiments, the subject is HAL reference. In some embodiments, the subject is heterozygous for a HAL variant nucleic acid molecule encoding a HAL predicted gain-of-function polypeptide. Furthermore, when the subject has a lower aggregate burden for having a HAL variant nucleic acid molecule encoding a HAL predicted gain-of-function polypeptide, and therefore has an increased risk of developing skin cancer, the subject is administered a therapeutic agent that treats or prevents skin cancer. In some embodiments, when the subject has a lower aggregate burden for having a HAL variant nucleic acid molecule encoding a HAL predicted gain-of-function polypeptide, the subject is administered the therapeutic agent that treats or prevents skin cancer in a dosage amount that is the same as or greater than the standard dosage amount administered to a subject who has a greater aggregate burden for having a HAL variant nucleic acid molecule encoding a HAL predicted gain-of-function polypeptide.

The present disclosure also provides methods of detecting the presence or absence of a HAL variant genomic nucleic acid molecule encoding a HAL predicted gain-of-function polypeptide in a biological sample obtained from a subject. It is understood that gene sequences within a population and mRNA molecules encoded by such genes can vary due to polymorphisms such as single nucleotide polymorphisms (SNPs). The sequences provided herein for the HAL variant genomic nucleic acid molecules are only exemplary sequences. Other sequences for the HAL variant genomic nucleic acid molecules are also possible.

The biological sample can be derived from any cell, tissue, or biological fluid from the subject. The biological sample may comprise any clinically relevant tissue such as, for example, a bone marrow sample, a tumor biopsy, a fine needle aspirate, or a sample of bodily fluid, such as blood, gingival crevicular fluid, plasma, serum, lymph, ascitic fluid, cystic fluid, or urine. In some embodiments, the biological sample comprises a buccal swab. The biological sample used in the methods disclosed herein can vary based on the assay format, nature of the detection method, and the tissues, cells, or extracts that are used as the sample. A biological sample can be processed differently depending on the assay being employed. For example, when detecting any HAL variant nucleic acid molecule, preliminary processing designed to isolate or enrich the biological sample for the HAL variant nucleic acid molecule can be employed. A variety of techniques may be used for this purpose. When detecting the level of any HAL variant mRNA molecule, different techniques can be used enrich the biological sample with mRNA molecules. Various methods to detect the presence or level of an mRNA molecule or the presence of a particular variant genomic DNA locus can be used.

The present disclosure also provides methods of detecting a HAL variant nucleic acid molecule, or the complement thereof, encoding a HAL predicted gain-of-function polypeptide in a subject. The methods comprise assaying a biological sample obtained from the subject to determine whether a nucleic acid molecule in the biological sample is a HAL variant nucleic acid molecule encoding a HAL predicted gain-of-function polypeptide.

In some embodiments, the HAL variant nucleic acid molecule encoding the HAL predicted gain-of-function polypeptide, or the complement thereof, is a genomic nucleic acid molecule having a nucleotide sequence comprising: an adenine at a position corresponding to position 11,352 according to SEQ ID NO:2, or the complement thereof; or a guanine at a position corresponding to position 14,441 according to SEQ ID NO:3, or the complement thereof. In some embodiments, the HAL variant genomic nucleic acid molecule encoding the HAL predicted gain-of-function polypeptide, or the complement thereof, has a nucleotide sequence comprising an adenine at a position corresponding to position 11,352 according to SEQ ID NO:2, or the complement thereof. In some embodiments, the HAL variant genomic nucleic acid molecule encoding the HAL predicted gain-of-function polypeptide, or the complement thereof, has a nucleotide sequence comprising a guanine at a position corresponding to position 14,441 according to SEQ ID NO:3, or the complement thereof.

In some embodiments, the biological sample comprises a cell or cell lysate. Such methods can further comprise, for example, obtaining a biological sample from the subject comprising a HAL genomic nucleic acid molecule. Such assays can comprise, for example determining the identity of these positions of the particular HAL nucleic acid molecule. In some embodiments, the method is an in vitro method.

In some embodiments, the assay comprises sequencing at least a portion of the nucleotide sequence of the HAL nucleic acid molecule, or the complement thereof, in the biological sample. In some embodiments, the assay comprises sequencing at least a portion of the nucleotide sequence of the HAL genomic nucleic acid molecule in the biological sample, wherein the sequenced portion comprises: a position corresponding to position 11,352 according to SEQ ID NO:2, or the complement thereof, or a position corresponding to position 14,441 according to SEQ ID NO:3, or the complement thereof. When the sequenced portion of the HAL nucleic acid molecule in the biological sample comprises: an adenine at a position corresponding to position 11,352 according to SEQ ID NO:2, or the complement thereof, or a guanine at a position corresponding to position 14,441 according to SEQ ID NO:3, or the complement thereof; then the HAL nucleic acid molecule in the biological sample is a HAL variant nucleic acid molecule encoding a HAL predicted gain-of-function polypeptide.

In some embodiments, the assay comprises: a) contacting the biological sample with a primer hybridizing to a portion of the nucleotide sequence of the HAL genomic nucleic acid molecule, or the complement thereof, that is proximate to a position corresponding to position 11,352 according to SEQ ID NO:2, or the complement thereof, or proximate to a position corresponding to position 14,441 according to SEQ ID NO:3, or the complement thereof; b) extending the primer at least through the position of the nucleotide sequence of the HAL genomic nucleic acid molecule, or the complement thereof, corresponding to position 11,352 according to SEQ ID NO:2, or the complement thereof, or corresponding to position 14,441 according to SEQ ID NO:3, or the complement thereof; and c) determining whether the extension product of the primer comprises: an adenine at a position corresponding to position 11,352 according to SEQ ID NO:2, or the complement thereof, or a guanine at a position corresponding to position 14,441 according to SEQ ID NO:3, or the complement thereof.

In some embodiments, the assay comprises sequencing the entire nucleic acid molecule. In some embodiments, only a HAL genomic nucleic acid molecule is analyzed.

In some embodiments, the assay comprises: a) amplifying at least a portion of the HAL nucleic acid molecule, or the complement thereof, in the biological sample, wherein the amplified portion comprises: an adenine at a position corresponding to position 11,352 according to SEQ ID NO:2, or the complement thereof, or a guanine at a position corresponding to position 14,441 according to SEQ ID NO:3, or the complement thereof; b) labeling the amplified nucleic acid molecule with a detectable label; c) contacting the labeled nucleic acid molecule with a support comprising an alteration-specific probe, wherein the alteration-specific probe comprises a nucleotide sequence which hybridizes under stringent conditions to the nucleotide sequence of the amplified nucleic acid molecule comprising: an adenine at a position corresponding to position 11,352 according to SEQ ID NO:2, or the complement thereof, or a guanine at a position corresponding to position 14,441 according to SEQ ID NO:3, or the complement thereof; and d) detecting the detectable label.

In some embodiments, the assay comprises: a) amplifying at least a portion of the HAL genomic nucleic acid molecule, or the complement thereof, in the biological sample, wherein the portion comprises: an adenine at a position corresponding to position 11,352 according to SEQ ID NO:2, or the complement thereof, or a guanine at a position corresponding to position 14,441 according to SEQ ID NO:3, or the complement thereof; and b) detecting the detectable label.

In some embodiments, the assay comprises: contacting the HAL nucleic acid molecule, or the complement thereof, in the biological sample with an alteration-specific probe comprising a detectable label, wherein the alteration-specific probe comprises a nucleotide sequence which hybridizes under stringent conditions to the nucleotide sequence of the HAL nucleic acid molecule, or the complement thereof, comprising: an adenine at a position corresponding to position 11,352 according to SEQ ID NO:2, or the complement thereof, or a guanine at a position corresponding to position 14,441 according to SEQ ID NO:3, or the complement thereof; and detecting the detectable label.

In some embodiments, the HAL nucleic acid molecule is present within a cell obtained from the subject.

Alteration-specific polymerase chain reaction techniques can be used to detect mutations such as SNPs in a nucleotide sequence. Alteration-specific primers can be used because the DNA polymerase will not extend when a mismatch with the template is present.

In some embodiments, the assay comprises RNA sequencing (RNA-Seq). In some embodiments, the assays also comprise reverse transcribing mRNA into cDNA, such as by the reverse transcriptase polymerase chain reaction (RT-PCR).

In some embodiments, the methods utilize probes and primers of sufficient nucleotide length to bind to the target nucleotide sequence and specifically detect and/or identify a polynucleotide comprising a HAL variant genomic nucleic acid molecule. The hybridization conditions or reaction conditions can be determined by the operator to achieve this result. The nucleotide length may be any length that is sufficient for use in a detection method of choice, including any assay described or exemplified herein. Such probes and primers can hybridize specifically to a target nucleotide sequence under high stringency hybridization conditions. Probes and primers may have complete nucleotide sequence identity of contiguous nucleotides within the target nucleotide sequence, although probes differing from the target nucleotide sequence and that retain the ability to specifically detect and/or identify a target nucleotide sequence may be designed by conventional methods. Probes and primers can have about 80%, about 85%, about 90%, about 91%, about 92%, about 93%, about 94%, about 95%, about 96%, about 97%, about 98%, about 99%, or 100% sequence identity or complementarity with the nucleotide sequence of the target nucleic acid molecule.

In some embodiments, to determine whether a HAL nucleic acid molecule (e.g., genomic nucleic acid molecule), or complement thereof, within a biological sample comprises a nucleotide sequence comprising an adenine at a position corresponding to position 11,352 according to SEQ ID NO:2, or the complement thereof, the biological sample can be subjected to an amplification method using a primer pair that includes a first primer derived from the 5' flanking sequence adjacent to an adenine at a position corresponding to position 11,352 according to SEQ ID NO:2, and a second primer derived from the 3' flanking sequence adjacent to an adenine at a position corresponding to position 11,352 according to SEQ ID NO:2 to produce an amplicon that is indicative of the presence of the SNP at a position encoding an adenine at a position corresponding to position 11,352 according to SEQ ID NO:2. In some embodiments, the amplicon may range in length from the combined length of the primer pairs plus one nucleotide base pair to any length of amplicon producible by a DNA amplification protocol. This distance can range from one nucleotide base pair up to the limits of the amplification reaction, or about twenty thousand nucleotide base pairs. Optionally, the primer pair flanks a region including positions comprising an adenine at a position corresponding to position 11,352 according to SEQ ID NO:2, and at least 1, 2, 3, 4, 5, 6, 7, 8, 9, 10, or more nucleotides on each side of positions comprising an adenine at a position corresponding to position 11,352 according to SEQ ID NO:2.

In some embodiments, to determine whether a HAL nucleic acid molecule (e.g., genomic nucleic acid molecule), or complement thereof, within a biological sample comprises a nucleotide sequence comprising a guanine at a position corresponding to position 14,441 according to SEQ ID NO:3, or the complement thereof, the biological sample can be subjected to an amplification method using a primer pair that includes a first primer derived from the 5' flanking sequence adjacent to a guanine at a position corresponding to position 14,441 according to SEQ ID NO:3, and a second primer derived from the 3' flanking sequence adjacent to a guanine at a position corresponding to position 14,441 according to SEQ ID NO:3 to produce an amplicon that is indicative of the presence of the SNP at a position encoding a guanine at a position corresponding to position 14,441 according to SEQ ID NO:3. In some embodiments, the amplicon may range in length from the combined length of the primer pairs plus one nucleotide base pair to any length of amplicon producible by a DNA amplification protocol. This distance can range from one nucleotide base pair up to the limits of the amplification reaction, or about twenty thousand nucleotide base pairs. Optionally, the primer pair flanks a region including positions comprising a guanine at a position corresponding to position 14,431 according to SEQ ID NO:3, and at least 1, 2, 3, 4, 5, 6, 7, 8, 9, 10, or more nucleotides on each side of positions comprising a guanine at a position corresponding to position 14,441 according to SEQ ID NO:3.

Similar amplicons can be generated from the mRNA and/or cDNA sequences. PCR primer pairs can be derived from a known sequence, for example, by using computer programs intended for that purpose, such as the PCR primer analysis tool in Vector NTI version 10 (Informax Inc., Bethesda Md.); PrimerSelect (DNASTAR Inc., Madison, Wis.); and Primer3 (Version 0.4.0. COPYRGT., 1991, Whitehead Institute for Biomedical Research, Cambridge, Mass.). Additionally, the sequence can be visually scanned and primers manually identified using known guidelines.

Illustrative examples of nucleic acid sequencing techniques include, but are not limited to, chain terminator (Sanger) sequencing and dye terminator sequencing. Other methods involve nucleic acid hybridization methods other than sequencing, including using labeled primers or probes directed against purified DNA, amplified DNA, and fixed cell preparations (fluorescence in situ hybridization (FISH)). In some methods, a target nucleic acid molecule may be amplified prior to or simultaneous with detection. Illustrative examples of nucleic acid amplification techniques include, but are not limited to, polymerase chain reaction (PCR), ligase chain reaction (LCR), strand displacement amplification (SDA), and nucleic acid sequence based amplification (NASBA). Other methods include, but are not limited to, ligase chain reaction, strand displacement amplification, and thermophilic SDA (tSDA).

In hybridization techniques, stringent conditions can be employed such that a probe or primer will specifically hybridize to its target. In some embodiments, a polynucleotide primer or probe under stringent conditions will hybridize to its target sequence to a detectably greater degree than to other non-target sequences, such as, at least 2-fold, at least 3-fold, at least 4-fold, or more over background, including over 10-fold over background. In some embodiments, a polynucleotide primer or probe under stringent conditions will hybridize to its target nucleotide sequence to a detectably greater degree than to other nucleotide sequences by at least 2-fold. In some embodiments, a polynucleotide primer or probe under stringent conditions will hybridize to its target nucleotide sequence to a detectably greater degree than to other nucleotide sequences by at least 3-fold. In some embodiments, a polynucleotide primer or probe under stringent conditions will hybridize to its target nucleotide sequence to a detectably greater degree than to other nucleotide sequences by at least 4-fold. In some embodiments, a polynucleotide primer or probe under stringent conditions will hybridize to its target nucleotide sequence to a detectably greater degree than to other nucleotide sequences by over 10-fold over background. Stringent conditions are sequence-dependent and will be different in different circumstances.

Appropriate stringency conditions which promote DNA hybridization, for example, 6× sodium chloride/sodium citrate (SSC) at about 45° C., followed by a wash of 2X SSC at 50° C., are known or can be found in *Current Protocols in Molecular Biology*, John Wiley & Sons, N.Y. (1989), 6.3.1-6.3.6. Typically, stringent conditions for hybridization and detection will be those in which the salt concentration is less than about 1.5 M $Na^+$ ion, typically about 0.01 to 1.0 M $Na^+$ ion concentration (or other salts) at pH 7.0 to 8.3 and the temperature is at least about 30° C. for short probes (such as, for example, 10 to 50 nucleotides) and at least about 60° C.

for longer probes (such as, for example, greater than 50 nucleotides). Stringent conditions may also be achieved with the addition of destabilizing agents such as formamide. Optionally, wash buffers may comprise about 0.1% to about 1% SDS. Duration of hybridization is generally less than about 24 hours, usually about 4 to about 12 hours. The duration of the wash time will be at least a length of time sufficient to reach equilibrium.

The present disclosure also provides methods of detecting the presence of a HAL predicted gain-of-function polypeptide comprising performing an assay on a biological sample obtained from the subject to determine whether a HAL polypeptide in the biological sample contains one or more variations that causes the polypeptide to have a gain-of-function (partial or complete) or predicted gain-of-function (partial or complete).

In some embodiments, when the subject does not have a HAL predicted gain-of-function polypeptide, the subject has an increased risk of developing skin cancer, such as non-melanoma skin cancer, basal cell carcinoma, squamous cell carcinoma, melanoma, Merkel cell carcinoma, dermatofibrosarcoma protuberans, or sebaceous carcinoma. In some embodiments, when the subject has a HAL predicted gain-of-function polypeptide, the subject has a decreased risk of developing skin cancer, such as non-melanoma skin cancer, basal cell carcinoma, squamous cell carcinoma, melanoma, Merkel cell carcinoma, dermatofibrosarcoma protuberans, or sebaceous carcinoma.

The present disclosure also provides isolated nucleic acid molecules that hybridize to HAL variant genomic nucleic acid molecules. In some embodiments, such isolated nucleic acid molecules hybridize to HAL variant nucleic acid molecules under stringent conditions. Such nucleic acid molecules can be used, for example, as probes, primers, alteration-specific probes, or alteration-specific primers as described or exemplified herein.

In some embodiments, the isolated nucleic acid molecules hybridize to a portion of the HAL variant nucleic acid molecule that includes a position corresponding to position 11,352 according to SEQ ID NO:2, or position 14,441 according to SEQ ID NO:3.

In some embodiments, such isolated nucleic acid molecules comprise or consist of at least about 5, at least about 8, at least about 10, at least about 11, at least about 12, at least about 13, at least about 14, at least about 15, at least about 16, at least about 17, at least about 18, at least about 19, at least about 20, at least about 21, at least about 22, at least about 23, at least about 24, at least about 25, at least about 30, at least about 35, at least about 40, at least about 45, at least about 50, at least about 55, at least about 60, at least about 65, at least about 70, at least about 75, at least about 80, at least about 85, at least about 90, at least about 95, at least about 100, at least about 200, at least about 300, at least about 400, at least about 500, at least about 600, at least about 700, at least about 800, at least about 900, at least about 1000, at least about 2000, at least about 3000, at least about 4000, or at least about 5000 nucleotides. In some embodiments, such isolated nucleic acid molecules comprise or consist of at least about 5, at least about 8, at least about 10, at least about 11, at least about 12, at least about 13, at least about 14, at least about 15, at least about 16, at least about 17, at least about 18, at least about 19, at least about 20, at least about 21, at least about 22, at least about 23, at least about 24, or at least about 25 nucleotides. In some embodiments, the isolated nucleic acid molecules comprise or consist of at least about 18 nucleotides. In some embodiments, the isolated nucleic acid molecules comprise or consists of at least about 15 nucleotides. In some embodiments, the isolated nucleic acid molecules consist of or comprise from about 10 to about 35, from about 10 to about 30, from about 10 to about 25, from about 12 to about 30, from about 12 to about 28, from about 12 to about 24, from about 15 to about 30, from about 15 to about 25, from about 18 to about 30, from about 18 to about 25, from about 18 to about 24, or from about 18 to about 22 nucleotides. In some embodiments, the isolated nucleic acid molecules consist of or comprise from about 18 to about 30 nucleotides. In some embodiments, the isolated nucleic acid molecules comprise or consist of at least about 15 nucleotides to at least about 35 nucleotides.

In some embodiments, the isolated alteration-specific probe or alteration-specific primer comprises at least about 15 nucleotides, wherein the alteration-specific probe or alteration-specific primer comprises a nucleotide sequence which is complementary to the nucleotide sequence of a portion of a HAL variant nucleic acid molecule encoding a HAL predicted gain-of-function polypeptide, or the complement thereof. In some embodiments, the portion comprises a position corresponding to position 11,352 according to SEQ ID NO:2, or the complement thereof, or position 14,441 according to SEQ ID NO:3, or the complement thereof.

In some embodiments, the isolated nucleic acid molecules hybridize to at least about 15 contiguous nucleotides of a nucleic acid molecule that is at least about 70%, at least about 75%, at least about 80%, at least about 85%, at least about 90%, at least about 95%, at least about 96%, at least about 97%, at least about 98%, at least about 99%, or 100% identical to a HAL variant genomic nucleic acid molecule. In some embodiments, the isolated nucleic acid molecules consist of or comprise from about 15 to about 100 nucleotides, or from about 15 to about 35 nucleotides. In some embodiments, the isolated nucleic acid molecules consist of or comprise from about 15 to about 100 nucleotides. In some embodiments, the isolated nucleic acid molecules consist of or comprise from about 15 to about 35 nucleotides.

In some embodiments, the isolated alteration-specific probes or alteration-specific primers comprise at least about 15 nucleotides, wherein the alteration-specific probe or alteration-specific primer comprises a nucleotide sequence which is complementary to a portion of a nucleotide sequence of a HAL variant nucleic acid molecule encoding a HAL predicted gain-of-function polypeptide, wherein the portion comprises a position corresponding to position 11,352 according to SEQ ID NO:2, or the complement thereof, or position 14,441 according to SEQ ID NO:3, or the complement thereof.

In some embodiments, the alteration-specific probes and alteration-specific primers comprise DNA. In some embodiments, the alteration-specific probes and alteration-specific primers comprise RNA.

In some embodiments, the probes and primers described herein (including alteration-specific probes and alteration-specific primers) have a nucleotide sequence that specifically hybridizes to any of the nucleic acid molecules disclosed herein, or the complement thereof. In some embodiments, the probes and primers specifically hybridize to any of the nucleic acid molecules disclosed herein under stringent conditions.

In some embodiments, the primers, including alteration-specific primers, can be used in second generation sequencing or high throughput sequencing. In some instances, the primers, including alteration-specific primers, can be modified. In particular, the primers can comprise various modifications that are used at different steps of, for example, Massive Parallel Signature Sequencing (MPSS), Polony sequencing, and 454 Pyrosequencing. Modified primers can be used at several steps of the process, including biotinylated primers in the cloning step and fluorescently labeled primers used at the bead loading step and detection step. Polony sequencing is generally performed using a paired-end tags library wherein each molecule of DNA template is about 135 bp in length. Biotinylated primers are used at the bead loading step and emulsion PCR. Fluorescently labeled degenerate nonamer oligonucleotides are used at the detection step. An adaptor can contain a 5'-biotin tag for immobilization of the DNA library onto streptavidin-coated beads.

The probes and primers described herein can be used to detect a nucleotide variation within any of the HAL variant genomic nucleic acid molecules disclosed herein. The primers described herein can be used to amplify the HAL variant genomic nucleic acid molecules, or a fragment thereof.

The present disclosure also provides pairs of primers comprising any of the primers described above. For example, if one of the primers' 3'-ends hybridizes to a guanine at a position corresponding to position 11,352 according to SEQ ID NO:1 (rather than an adenine) in a particular HAL nucleic acid molecule, then the presence of the amplified fragment would indicate the presence of a HAL reference genomic nucleic acid molecule. Conversely, if one of the primers' 3'-ends hybridizes to an adenine at a position corresponding to position 11,352 according to SEQ ID NO:2 (rather than a guanine) in a particular HAL nucleic acid molecule, then the presence of the amplified fragment would indicate the presence of the HAL variant genomic nucleic acid molecule. In some embodiments, the nucleotide of the primer complementary to the adenine at a position corresponding to position 11,352 according to SEQ ID NO:2 can be at the 3' end of the primer.

The present disclosure also provides pairs of primers comprising any of the primers described above. For example, if one of the primers' 3'-ends hybridizes to an adenine at a position corresponding to position 14,441 according to SEQ ID NO:1 (rather than a guanine) in a particular HAL nucleic acid molecule, then the presence of the amplified fragment would indicate the presence of a HAL reference genomic nucleic acid molecule. Conversely, if one of the primers' 3'-ends hybridizes to a guanine at a position corresponding to position 14,441 according to SEQ ID NO:3 (rather than an adenine) in a particular HAL nucleic acid molecule, then the presence of the amplified fragment would indicate the presence of the HAL variant genomic nucleic acid molecule. In some embodiments, the nucleotide of the primer complementary to the guanine at a position corresponding to position 14,441 according to SEQ ID NO:3 can be at the 3' end of the primer.

In the context of the present disclosure "specifically hybridizes" means that the probe or primer (such as, for example, the alteration-specific probe or alteration-specific primer) does not hybridize to a nucleotide sequence encoding a HAL reference genomic nucleic acid molecule.

In any of the embodiments described throughout the present disclosure, the probes (such as, for example, an alteration-specific probe) can comprise a label. In some embodiments, the label is a fluorescent label, a radiolabel, or biotin.

The present disclosure also provides supports comprising a substrate to which any one or more of the probes disclosed herein is attached. Solid supports are solid-state substrates or supports with which molecules, such as any of the probes disclosed herein, can be associated. A form of solid support is an array. Another form of solid support is an array detector. An array detector is a solid support to which multiple different probes have been coupled in an array, grid, or other organized pattern. A form for a solid-state substrate is a microtiter dish, such as a standard 96-well type. In some embodiments, a multiwell glass slide can be employed that normally contains one array per well. In some embodiments, the support is a microarray.

The present disclosure also provides molecular complexes comprising or consisting of any of the HAL variant genomic nucleic acid molecules, or complement thereof, described herein and any of the alteration-specific primers or alteration-specific probes described herein. In some embodiments, the HAL variant genomic nucleic acid molecules, or complement thereof, in the molecular complexes are single-stranded. In some embodiments, the molecular complex comprises or consists of any of the HAL variant genomic nucleic acid molecules, or complement thereof, described herein and any of the alteration-specific primers described herein. In some embodiments, the molecular complex comprises or consists of any of the HAL variant genomic nucleic acid molecules, or complement thereof, described herein and any of the alteration-specific probes described herein.

In some embodiments, the molecular complex comprises an alteration-specific primer or an alteration-specific probe hybridized to a HAL genomic nucleic acid molecule encoding a HAL predicted gain-of-function polypeptide, wherein the alteration-specific primer or the alteration-specific probe is hybridized to the HAL genomic nucleic acid molecule at a position corresponding to position 11,352 according to SEQ ID NO:2, or the complement thereof. In some embodiments, the molecular complex comprises an alteration-specific primer or an alteration-specific probe hybridized to a HAL genomic nucleic acid molecule encoding a HAL predicted gain-of-function polypeptide, wherein the alteration-specific primer or the alteration-specific probe is hybridized to the HAL genomic nucleic acid molecule at a position corresponding to position 14,441 according to SEQ ID NO:3, or the complement thereof.

In some embodiments, the genomic nucleic acid molecule in the molecular complex comprises SEQ ID NO:2. In some embodiments, the genomic nucleic acid molecule in the molecular complex comprises SEQ ID NO:3.

In some embodiments, the molecular complex comprises an alteration-specific probe or an alteration-specific primer comprising a label. In some embodiments, the label is a fluorescent label, a radiolabel, or biotin. In some embodiments, the molecular complex further comprises a non-human polymerase.

The nucleotide sequence of a HAL reference genomic nucleic acid molecule is set forth in SEQ ID NO:1 (ENSG00000084110.11 encompassing chr12:95,972,662-95,996,344 in the GRCh38/hg38 human genome assembly). Referring to SEQ ID NO:1, position 11,352 is a guanine. Referring to SEQ ID NO:1, position 14,441 is an adenine.

A HAL variant genomic nucleic acid molecule exists, wherein the guanine at position 11,352 is replaced with an adenine. The nucleotide sequence of this HAL variant genomic nucleic acid molecule is set forth in SEQ ID NO:2 (rs53819817).

Another HAL variant genomic nucleic acid molecule exists, wherein the adenine at position 14,41 is replaced with a guanine. The nucleotide sequence of this HAL variant genomic nucleic acid molecule is set forth in SEQ ID NO:3 (rs10859995).

The nucleotide sequence of a HAL reference mRNA molecule is set forth in SEQ ID NO:4. The nucleotide sequence of another HAL reference mRNA molecule is set forth in SEQ ID NO:5. The nucleotide sequence of another HAL reference mRNA molecule is set forth in SEQ ID NO:6. The nucleotide sequence of another HAL reference mRNA molecule is set forth in SEQ ID NO:7. The nucleotide sequence of another HAL reference mRNA molecule is set forth in SEQ ID NO:8. The nucleotide sequence of another HAL reference mRNA molecule is set forth in SEQ ID NO:9. The nucleotide sequence of another HAL reference mRNA molecule is set forth in SEQ ID NO:10. The nucleotide sequence of another HAL reference mRNA molecule is set forth in SEQ ID NO:11. The nucleotide sequence of another HAL reference mRNA molecule is set forth in SEQ ID NO:12. The nucleotide sequence of another HAL reference mRNA molecule is set forth in SEQ ID NO:13. The nucleotide sequence of another HAL reference mRNA molecule is set forth in SEQ ID NO:14.

The nucleotide sequence of a HAL reference cDNA molecule is set forth in SEQ ID NO:15. The nucleotide sequence of another HAL reference cDNA molecule is set forth in SEQ ID NO:16. The nucleotide sequence of another HAL reference cDNA molecule is set forth in SEQ ID NO:17. The nucleotide sequence of another HAL reference cDNA molecule is set forth in SEQ ID NO:18. The nucleotide sequence of another HAL reference cDNA molecule is set forth in SEQ ID NO:19. The nucleotide sequence of another HAL reference cDNA molecule is set forth in SEQ ID NO:20. The nucleotide sequence of another HAL reference cDNA molecule is set forth in SEQ ID NO:21. The nucleotide sequence of another HAL reference cDNA molecule is set forth in SEQ ID NO:22. The nucleotide sequence of another HAL reference cDNA molecule is set forth in SEQ ID NO:23. The nucleotide sequence of another HAL reference cDNA molecule is set forth in SEQ ID NO:24. The nucleotide sequence of another HAL reference cDNA molecule is set forth in SEQ ID NO:25.

The genomic nucleic acid molecules, mRNA molecules, and cDNA molecules can be from any organism. For example, the genomic nucleic acid molecules, mRNA molecules, and cDNA molecules can be human or an ortholog from another organism, such as a non-human mammal, a rodent, a mouse, or a rat. It is understood that gene sequences within a population can vary due to polymorphisms such as single-nucleotide polymorphisms. The examples provided herein are only exemplary sequences. Other sequences are also possible.

Also provided herein are functional polynucleotides that can interact with the disclosed nucleic acid molecules. Examples of functional polynucleotides include, but are not limited to, antisense molecules, aptamers, ribozymes, triplex forming molecules, and external guide sequences. The functional polynucleotides can act as effectors, agonists, modulators, and stimulators of a specific activity possessed by a target molecule, or the functional polynucleotides can possess a de novo activity independent of any other molecules.

The isolated nucleic acid molecules disclosed herein can comprise RNA, DNA, or both RNA and DNA. The isolated nucleic acid molecules can also be linked or fused to a heterologous nucleic acid sequence, such as in a vector, or a heterologous label. For example, the isolated nucleic acid molecules disclosed herein can be within a vector or as an exogenous donor sequence comprising the isolated nucleic acid molecule and a heterologous nucleic acid sequence. The isolated nucleic acid molecules can also be linked or fused to a heterologous label. The label can be directly detectable (such as, for example, fluorophore) or indirectly detectable (such as, for example, hapten, enzyme, or fluorophore quencher). Such labels can be detectable by spectroscopic, photochemical, biochemical, immunochemical, or chemical means. Such labels include, for example, radiolabels, pigments, dyes, chromogens, spin labels, and fluorescent labels. The label can also be, for example, a chemiluminescent substance; a metal-containing substance; or an enzyme, where there occurs an enzyme-dependent secondary generation of signal. The term "label" can also refer to a "tag" or hapten that can bind selectively to a conjugated molecule such that the conjugated molecule, when added subsequently along with a substrate, is used to generate a detectable signal. For example, biotin can be used as a tag along with an avidin or streptavidin conjugate of horseradish peroxidate (HRP) to bind to the tag, and examined using a calorimetric substrate (such as, for example, tetramethylbenzidine (TMB)) or a fluorogenic substrate to detect the presence of HRP. Exemplary labels that can be used as tags to facilitate purification include, but are not limited to, myc, HA, FLAG or 3XFLAG, 6XHis or polyhistidine, glutathione-S-transferase (GST), maltose binding protein, an epitope tag, or the Fc portion of immunoglobulin. Numerous labels include, for example, particles, fluorophores, haptens, enzymes and their calorimetric, fluorogenic and chemiluminescent substrates and other labels.

The isolated nucleic acid molecules, or the complement thereof, can also be present within a host cell. In some embodiments, the host cell can comprise the vector that comprises any of the nucleic acid molecules described herein, or the complement thereof. In some embodiments, the nucleic acid molecule is operably linked to a promoter active in the host cell. In some embodiments, the promoter is an exogenous promoter. In some embodiments, the promoter is an inducible promoter. In some embodiments, the host cell is a bacterial cell, a yeast cell, an insect cell, or a mammalian cell. In some embodiments, the host cell is a bacterial cell. In some embodiments, the host cell is a yeast cell. In some embodiments, the host cell is an insect cell. In some embodiments, the host cell is a mammalian cell.

The disclosed nucleic acid molecules can comprise, for example, nucleotides or non-natural or modified nucleotides, such as nucleotide analogs or nucleotide substitutes. Such nucleotides include a nucleotide that contains a modified base, sugar, or phosphate group, or that incorporates a non-natural moiety in its structure. Examples of non-natural nucleotides include, but are not limited to, dideoxynucleotides, biotinylated, aminated, deaminated, alkylated, benzylated, and fluorophor-labeled nucleotides.

The nucleic acid molecules disclosed herein can also comprise one or more nucleotide analogs or substitutions. A nucleotide analog is a nucleotide which contains a modification to either the base, sugar, or phosphate moieties. Modifications to the base moiety include, but are not limited to, natural and synthetic modifications of A, C, G, and T/U, as well as different purine or pyrimidine bases such as, for example, pseudouridine, uracil-5-yl, hypoxanthin-9-yl(I), and 2-aminoadenin-9-yl. Modified bases include, but are not limited to, 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo (such as, for example, 5-bromo), 5-trifluoromethyl and other 5-substituted uracils and cytosines, 7-methylguanine, 7-methyladenine, 8-azaguanine, 8-azaadenine, 7-deazaguanine, 7-deazaadenine, 3-deazaguanine, and 3-deazaadenine.

Nucleotide analogs can also include modifications of the sugar moiety. Modifications to the sugar moiety include, but are not limited to, natural modifications of the ribose and deoxy ribose as well as synthetic modifications. Sugar modifications include, but are not limited to, the following modifications at the 2' position: OH; F; O—, S—, or N-alkyl; O—, S—, or N-alkenyl; O—, S— or N-alkynyl; or O-alkyl-O-alkyl, wherein the alkyl, alkenyl, and alkynyl may be substituted or unsubstituted $C_{1-10}$alkyl or $C_{2-10}$alkenyl, and $C_{2-10}$alkynyl. Exemplary 2' sugar modifications also include, but are not limited to, $—O[(CH_2)_nO]_mCH_3$, $—O(CH_2)_nOCH_3$, $—O(CH_2)_nNH_2$, $—O(CH_2)_nCH_3$, $—O(CH_2)_n—ONH_2$, and $—O(CH_2)_nON[(CH_2)_nCH_3)]_2$, where n and m, independently, are from 1 to about 10. Other modifications at the 2' position include, but are not limited to, $C_{1-10}$alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. Similar modifications may also be made at other positions on the sugar, particularly the 3' position of the sugar on the 3' terminal nucleotide or in 2'-5' linked oligonucleotides and the 5' position of 5' terminal nucleotide. Modified sugars can also include those that contain modifications at the bridging ring oxygen, such as $CH_2$ and S. Nucleotide sugar analogs can also have sugar mimetics, such as cyclobutyl moieties in place of the pentofuranosyl sugar.

Nucleotide analogs can also be modified at the phosphate moiety. Modified phosphate moieties include, but are not limited to, those that can be modified so that the linkage between two nucleotides contains a phosphorothioate, chiral phosphorothioate, phosphorodithioate, phosphotriester, aminoalkylphosphotriester, methyl and other alkyl phosphonates including 3'-alkylene phosphonate and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates. These phosphate or modified phosphate linkage between two nucleotides can be through a 3'-5' linkage or a 2'-5' linkage, and the linkage can contain inverted polarity such as 3'-5' to 5'-3' or 2'-5' to 5'-2'. Various salts, mixed salts, and free acid forms are also included. Nucleotide substitutes also include peptide nucleic acids (PNAs).

The present disclosure also provides vectors comprising any one or more of the nucleic acid molecules disclosed herein. In some embodiments, the vectors comprise any one or more of the nucleic acid molecules disclosed herein and a heterologous nucleic acid. The vectors can be viral or nonviral vectors capable of transporting a nucleic acid molecule. In some embodiments, the vector is a plasmid or cosmid (such as, for example, a circular double-stranded DNA into which additional DNA segments can be ligated). In some embodiments, the vector is a viral vector, wherein additional DNA segments can be ligated into the viral genome. Expression vectors include, but are not limited to, plasmids, cosmids, retroviruses, adenoviruses, adeno-associated viruses (AAV), plant viruses such as cauliflower mosaic virus and tobacco mosaic virus, yeast artificial chromosomes (YACs), Epstein-Barr (EBV)-derived episomes, and other expression vectors known in the art.

Desired regulatory sequences for mammalian host cell expression can include, for example, viral elements that direct high levels of polypeptide expression in mammalian cells, such as promoters and/or enhancers derived from retroviral LTRs, cytomegalovirus (CMV) (such as, for example, CMV promoter/enhancer), Simian Virus 40 (SV40) (such as, for example, SV40 promoter/enhancer), adenovirus, (such as, for example, the adenovirus major late promoter (AdMLP)), polyoma and strong mammalian promoters such as native immunoglobulin and actin promoters. Methods of expressing polypeptides in bacterial cells or fungal cells (such as, for example, yeast cells) are also well known. A promoter can be, for example, a constitutively active promoter, a conditional promoter, an inducible promoter, a temporally restricted promoter (such as, for example, a developmentally regulated promoter), or a spatially restricted promoter (such as, for example, a cell-specific or tissue-specific promoter).

Percent identity (or percent complementarity) between particular stretches of nucleotide sequences within nucleic acid molecules or amino acid sequences within polypeptides can be determined routinely using BLAST programs (basic local alignment search tools) and PowerBLAST programs (Altschul et al., J. Mol. Biol., 1990, 215, 403-410; Zhang and Madden, Genome Res., 1997, 7, 649-656) or by using the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489). Herein, if reference is made to percent sequence identity, the higher percentages of sequence identity are preferred over the lower ones.

The present disclosure also provides compositions comprising any one or more of the isolated nucleic acid molecules, genomic nucleic acid molecules, mRNA molecules, and/or cDNA molecules disclosed herein, or vectors comprising the same. In some embodiments, the composition is a pharmaceutical composition. In some embodiments, the compositions comprise a carrier and/or excipient. Examples of carriers include, but are not limited to, poly(lactic acid) (PLA) microspheres, poly(D,L-lactic-coglycolic-acid) (PLGA) microspheres, liposomes, micelles, inverse micelles, lipid cochleates, and lipid microtubules. A carrier may comprise a buffered salt solution such as PBS, HBSS, etc.

As used herein, the phrase "corresponding to" or grammatical variations thereof when used in the context of the numbering of a particular nucleotide or nucleotide sequence or position refers to the numbering of a specified reference sequence when the particular nucleotide or nucleotide sequence is compared to a reference sequence (such as, for example, SEQ ID NO:1, SEQ ID NO:2, or SEQ ID NO:3). In other words, the residue (such as, for example, nucleotide or amino acid) number or residue (such as, for example, nucleotide or amino acid) position of a particular polymer is designated with respect to the reference sequence rather than by the actual numerical position of the residue within the particular nucleotide or nucleotide sequence. For example, a particular nucleotide sequence can be aligned to a reference sequence by introducing gaps to optimize residue matches between the two sequences. In these cases, although the gaps are present, the numbering of the residue in the particular nucleotide or nucleotide sequence is made with respect to the reference sequence to which it has been aligned.

For example, a HAL variant genomic nucleic acid molecule comprising a nucleotide sequence encoding a HAL predicted gain-of-function polypeptide, wherein the nucleotide sequence comprises an adenine at a position corresponding to position 11,352 according to SEQ ID NO:2 means that if the nucleotide sequence of the HAL genomic nucleic acid molecule is aligned to the sequence of SEQ ID NO:2, the HAL sequence has an adenine residue at the position that corresponds to position 11,352 of SEQ ID NO:2. These phrases refer to a HAL variant genomic nucleic acid molecule encoding a HAL predicted gain-of-function polypeptide, wherein the genomic nucleic acid molecule has a nucleotide sequence that comprises an adenine residue that is homologous to the adenine residue at position 11,352 of SEQ ID NO:2.

As described herein, a position within a HAL variant genomic nucleic acid molecule that corresponds to position 11,352 according to SEQ ID NO:2, for example, can be identified by performing a sequence alignment between the nucleotide sequence of a particular HAL genomic nucleic acid molecule and the nucleotide sequence of SEQ ID NO:2. A variety of computational algorithms exist that can be used for performing a sequence alignment to identify a nucleotide position that corresponds to, for example, position 11,352 in SEQ ID NO:2. For example, by using the NCBI BLAST algorithm (Altschul et al., Nucleic Acids Res., 1997, 25, 3389-3402) or CLUSTALW software (Sievers and Higgins, Methods Mol. Biol., 2014, 1079, 105-116) sequence alignments may be performed. However, sequences can also be aligned manually.

The amino acid sequence of a HAL reference polypeptide is set forth in SEQ ID NO:26. Referring to SEQ ID NO:26, the HAL reference polypeptide is 657 amino acids in length.

The amino acid sequence of another HAL reference polypeptide is set forth in SEQ ID NO:27. Referring to SEQ ID NO:27, the HAL reference polypeptide is 449 amino acids in length.

The amino acid sequence of another HAL reference polypeptide is set forth in SEQ ID NO:28. Referring to SEQ ID NO:28, the HAL reference polypeptide is 591 amino acids in length.

The amino acid sequence of another HAL reference polypeptide is set forth in SEQ ID NO:29. Referring to SEQ ID NO:29, the HAL reference polypeptide is 219 amino acids in length.

The amino acid sequence of another HAL reference polypeptide is set forth in SEQ ID NO:30. Referring to SEQ ID NO:30, the HAL reference polypeptide is 167 amino acids in length.

Because the HAL variant nucleic acid molecules described herein comprise variations within the non-coding region of HAL, the HAL predicted gain-of-function polypeptide can be any of the foregoing HAL polypeptides that are encoded by any of the HAL variant nucleic acid molecules described herein.

The nucleotide and amino acid sequences listed in the accompanying sequence listing are shown using standard letter abbreviations for nucleotide bases, and three-letter code for amino acids. The nucleotide sequences follow the standard convention of beginning at the 5' end of the sequence and proceeding forward (i.e., from left to right in each line) to the 3' end. Only one strand of each nucleotide sequence is shown, but the complementary strand is understood to be included by any reference to the displayed strand. The amino acid sequence follows the standard convention of beginning at the amino terminus of the sequence and proceeding forward (i.e., from left to right in each line) to the carboxy terminus.

The present disclosure also provides therapeutic agents that treat or prevent skin cancer for use in the treatment or prevention of skin cancer (or for use in the preparation of a medicament for treating or preventing skin cancer) in a subject, wherein the subject has any of the HAL variant genomic nucleic acid molecules encoding a HAL predicted gain-of-function polypeptide described herein. The therapeutic agents that treat or prevent skin cancer can be any of the therapeutic agents that treat or prevent skin cancer described herein. The skin cancer can be any of non-melanoma skin cancer, basal cell carcinoma, squamous cell carcinoma, melanoma, Merkel cell carcinoma, dermatofibrosarcoma protuberans, and sebaceous carcinoma.

In some embodiments, the subject is identified as having a genomic nucleic acid molecule encoding a HAL predicted gain-of-function polypeptide, or the complement thereof, wherein the genomic nucleic acid molecule has a nucleotide sequence comprising an adenine at a position corresponding to position 11,352 according to SEQ ID NO:2, or the complement thereof.

In some embodiments, the subject is identified as having a genomic nucleic acid molecule encoding a HAL predicted gain-of-function polypeptide, or the complement thereof, wherein the genomic nucleic acid molecule has a nucleotide sequence comprising a guanine at a position corresponding to position 14,441 according to SEQ ID NO:3, or the complement thereof.

The present disclosure also provides HAL agonists for use in the treatment or prevention of skin cancer (or for use in the preparation of a medicament for treating or preventing skin cancer) in a subject, wherein the subject is heterozygous for any of the HAL variant genomic nucleic acid molecules encoding a HAL predicted gain-of-function polypeptides described herein, or wherein the subject is reference for a HAL genomic nucleic acid molecule. The HAL agonists can be any of the HAL agonists described herein. The skin cancer can be any of non-melanoma skin cancer, basal cell carcinoma, squamous cell carcinoma, melanoma, Merkel cell carcinoma, dermatofibrosarcoma protuberans, and sebaceous carcinoma.

In some embodiments, the subject is reference for a HAL genomic nucleic acid molecule.

In some embodiments, the subject is heterozygous for a genomic nucleic acid molecule encoding a HAL predicted gain-of-function polypeptide, or the complement thereof, wherein the genomic nucleic acid molecule has a nucleotide sequence comprising an adenine at a position corresponding to position 11,352 according to SEQ ID NO:2, or the complement thereof.

In some embodiments, the subject is heterozygous for a genomic nucleic acid molecule encoding a HAL predicted gain-of-function polypeptide, or the complement thereof, wherein the genomic nucleic acid molecule has a nucleotide sequence comprising a guanine at a position corresponding to position 14,441 according to SEQ ID NO:3, or the complement thereof.

All patent documents, websites, other publications, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Likewise, if different versions of a publication, website or the like are published at different times, the version most recently published at the effective filing date of the application is meant unless otherwise indicated. Any feature, step, element, embodiment, or aspect of the present disclosure can be used in combination with any other feature, step, element, embodiment, or aspect unless specifically indicated otherwise. Although the present disclosure has been described in some detail by way of illustration and example for purposes of clarity and understanding, it will be apparent that certain changes and modifications may be practiced within the scope of the appended claims.

The following examples are provided to describe the embodiments in greater detail. They are intended to illustrate, not to limit, the claimed embodiments. The following examples provide those of ordinary skill in the art with a disclosure and description of how the compounds, compositions, articles, devices and/or methods described herein are made and evaluated, and are intended to be purely exemplary and are not intended to limit the scope of any claims. Efforts have been made to ensure accuracy with respect to numbers (such as, for example, amounts, temperature, etc.), but some errors and deviations may be accounted for. Unless indicated otherwise, parts are parts by weight, temperature is in ° C. or is at ambient temperature, and pressure is at or near atmospheric.

EXAMPLES

Example 1: Association of Skin Cancer with HAL GOF Variants

The exomes of 454,787 UKB study participants were sequenced, with 95.8% of targeted bases covered at a depth of 20X or greater, as previously described (Szustakowski, Advancing Human Genetics Research and Drug Discovery through Exome Sequencing of the UK Biobank. bioRxiv, 2021; and Van Hout et al., Nature, 2020). Twelve million variants were identified in 39 million base pairs across the coding regions of 18,659 genes (data not shown). Among the variants identified were 3,375,252 (median of 10,260 per individual) synonymous, 7,689,495 (9,284 per individual) missense and 889,957 (212 per individual) putative gain-of-function (pLOF) variants (data not shown), of which about half were observed only once in this dataset (singleton variants; data not shown).

It was discovered that a burden of rare pLOF and deleterious missense variants in HAL was associated with higher vitamin D levels, as well as greater ease of skin tanning and higher risks of actinic keratosis and non-melanoma skin cancer (see, FIG. 2). These findings were independently supported by trait-lowering associations with a common variant (rs10859995: C, 58% frequency) that co-localizes ($r^2$=0.97) with an expression quantitative trait locus (rs3819817: T) that increases HAL expression in skin tissue (G. T. Consortium, Science, 2020, 369, 1318-1330; see, FIG. 1). Altogether, these results implicate HAL in both vitamin D levels and skin cancer and highlight an allelic series that includes common gain-of-function non-coding variants (trait-lowering).

Various modifications of the described subject matter, in addition to those described herein, will be apparent to those skilled in the art from the foregoing description. Such modifications are also intended to fall within the scope of the appended claims. Each reference (including, but not limited to, journal articles, U.S. and non-U.S. patents, patent application publications, international patent application publications, gene bank accession numbers, and the like) cited in the present application is incorporated herein by reference in its entirety and for all purposes.

---

What is claimed is:

1. A method of treating a subject with a therapeutic agent that treats or prevents skin cancer, wherein the subject has skin cancer or is at risk of developing skin cancer, the method comprising:

determining whether the subject has a Histidine Ammonia-Lyase (HAL) variant nucleic acid molecule, wherein the HAL variant nucleic acid molecule is a genomic nucleic acid molecule having a nucleotide sequence comprising an adenine at a position corresponding to position 11,352 according to SEQ ID NO:2, or a guanine at a position corresponding to position 14,441 according to SEQ ID NO:3 encoding a HAL predicted gain-of-function polypeptide by:

obtaining or having obtained a biological sample from the subject; and performing or having performed a sequence analysis on the biological sample to determine if the subject has a genotype comprising the HAL variant nucleic acid molecule encoding the HAL predicted gain-of-function polypeptide; and administering or continuing to administer the therapeutic agent that treats or prevents skin cancer in a standard dosage amount to a subject that is HAL reference, and/or administering a HAL agonist to the subject that is HAL reference; or administering or continuing to administer the therapeutic agent that treats or prevents skin cancer in an amount that is the same as or less than a standard dosage amount to a subject that is heterozygous for the HAL variant nucleic acid molecule, and/or administering a HAL agonist to the subject that is heterozygous for the HAL variant nucleic acid molecule;

wherein the presence of a genotype having the HAL variant nucleic acid molecule encoding the HAL predicted gain-of-function polypeptide indicates the subject has a decreased risk of developing skin cancer compared to a subject that does not have the HAL variant nucleic acid molecule encoding the HAL predicted gain-of-function polypeptide.

2. The method according to claim 1, wherein the subject is HAL reference, and the subject is administered or continued to be administered the therapeutic agent that treats or prevents skin cancer in a standard dosage amount, and is administered a HAL agonist.

3. The method according to claim 1, wherein the subject is heterozygous for a HAL variant nucleic acid molecule, and the subject is administered or continued to be administered the therapeutic agent that treats or prevents skin cancer in an amount that is the same as or less than a standard dosage amount, and is administered a HAL agonist.

4. The method according to claim 1, wherein the sequence analysis comprises sequencing at least a portion of the nucleotide sequence of the HAL genomic nucleic acid molecule, or the complement thereof, in the biological sample, wherein the sequenced portion comprises a position corresponding to position 11,352 according to SEQ ID NO:2, or the complement thereof, or a position corresponding to position 14,441 according to SEQ ID NO:3, or the complement thereof;

wherein when the sequenced portion of the HAL genomic nucleic acid molecule, or the complement thereof, in the biological sample comprises: an adenine at a position corresponding to position 11,352 according to SEQ ID NO:2, or the complement thereof, or a guanine at a position corresponding to position 14,441 according to SEQ ID NO:3, or the complement thereof, then the HAL genomic nucleic acid molecule in the biological sample is a HAL variant genomic nucleic acid molecule encoding a HAL predicted gain-of-function polypeptide.

5. The method according to claim 1, wherein the sequence analysis comprises:

a) contacting the biological sample with a primer hybridizing to a portion of the nucleotide sequence of the HAL genomic nucleic acid molecule, or the complement thereof, that is proximate to a position corresponding to position 11,352 according to SEQ ID NO:2, or the complement thereof, or to a position corresponding to position 14,441 according to SEQ ID NO: 3, or the complement thereof;

b) extending the primer at least through the position of the nucleotide sequence of the HAL genomic nucleic acid molecule, or the complement thereof, corresponding to position 11,352 according to SEQ ID NO:2, or the complement thereof, or to position 14,441 according to SEQ ID NO:3, or the complement thereof; and c) determining whether the extension product of the primer comprises: an adenine at a position corresponding to position 11,352 according to SEQ ID NO:2, or the complement thereof, or a guanine at a position corresponding to position 14,441 according to SEQ ID NO:3, or the complement thereof.

6. The method according to claim 4, wherein the sequence analysis comprises sequencing the entire nucleic acid molecule.

7. The method according to claim 1, wherein the sequence analysis comprises:
  a) amplifying at least a portion of the HAL genomic nucleic acid molecule, or the complement thereof, in the biological sample, wherein the portion comprises an adenine at a position corresponding to position 11,352 according to SEQ ID NO:2, or the complement thereof, or a guanine at a position corresponding to position 14,441 according to SEQ ID NO:3, or the complement thereof;
  b) labeling the amplified nucleic acid molecule with a detectable label;
  c) contacting the labeled nucleic acid molecule with a support comprising an alteration-specific probe, wherein the alteration-specific probe comprises a nucleotide sequence which hybridizes under stringent conditions to the nucleotide sequence of the amplified nucleic acid molecule comprising an adenine at a position corresponding to position 11,352 according to SEQ ID NO: 2, or the complement thereof, or a guanine at a position corresponding to position 14,441 according to SEQ ID NO:3, or the complement thereof; and
  d) detecting the detectable label.

8. The method according to claim 1, wherein the sequence analysis comprises:
  contacting the HAL genomic nucleic acid molecule, or the complement thereof, in the biological sample with an alteration-specific probe comprising a detectable label, wherein the alteration-specific probe comprises a nucleotide sequence which hybridizes under stringent conditions to the nucleotide sequence of the HAL genomic nucleic acid molecule, or the complement thereof, comprising an adenine at a position corresponding to position 11,352 according to SEQ ID NO:2, or the complement thereof, or a guanine at a position corresponding to position 14,441 according to SEQ ID NO:3, or the complement thereof; and
  detecting the detectable label.

9. The method according to claim 1, wherein the nucleic acid molecule is present within a cell in the biological sample obtained from the subject.

10. The method according to claim 1, wherein the HAL agonist comprises HAL protein or thyroid hormone ($T_3$).

* * * * *

SEQUENCE LISTING

```
Sequence total quantity: 30
SEQ ID NO: 1           moltype = DNA  length = 23683
FEATURE                Location/Qualifiers
source                 1..23683
                       mol_type = genomic DNA
                       organism = Homo sapiens
SEQUENCE: 1
agataaagac aggaacatgg tgtttataag ctgcccttaa tggcagagaa cacagacaga   60
aacgagggaa gagagagaaa ttggggaccc tgaagaaagg gggccagcag caggtaggtg  120
ccatcaggga caagaacagc acctcccagg gtgggagacc ccaggccttt ctggcagcag  180
gtctggatgg aaagtggaca ggaggctcac ccgtctgcat cccctgctcc tgcccctgct  240
cggctacaaa aaccaaaggg acagcaggta cctcaataaa tatttgtcca atgcatgaat  300
gagtaaaggt gaaggagggg gagtggtttg aaagtctatt ctcatccttc cagctgacca  360
caccccggta gccactcctg cataaagctc tcccctcctg tgaccagctg aggacctcag  420
gctgcagcgg agccatgccc agatacacgg tgcacgtacg tggggaatgg ctggcagtgc  480
cctgccagga cgcgcagctc actgtgggct ggctgggccg ggaggccgtg aggcgctata  540
tcaagaataa gcccgacaat ggtggcttca cctccgtgga tgacgcgcac ttccttgtgc  600
gccggtgcaa gggcctgggc ctgctggaca acgaggaccg gctcgaggtg gccctagaga  660
acaacgagtt cgtggaagtg ggtgagtggc tgcaggagag ggccgcgaac gggtgcggtt  720
tggcctggct tagtctttgc agcattgaac ccccacctca gggaaaatga tgagcagagg  780
tcaggcttgc cgaggctggc cctgtgcagg cacatgccac gcctctgggg atcttaagtc  840
ctcacacaac cctgtgagat gggtaggatt ctcctccacc tctgatggag gagaaatcag  900
agaggaggta acttacccag actccagcag ctagtaagta acaaagacta gactggtact  960
caaggctgca ggtctgaatc cctttgcagt gactgaatca ttttgaggtt attttgcctt 1020
tcgaaagaat ccaccccac ccccagactg gaggccggca gcatagcatc agttcagatt 1080
ttgaagaaaa taaagctggg aatggggatg gaagtggaat tctgtcttga actttcatct 1140
aaaccctctg tctctgccct gacacctacc tttctgcttt ttgctctcct cctacataaa 1200
gatgctaaga ccacatgaaa ccatctgaag cagttttaaa gcagccattt ctatagaatt 1260
catgggccaa tgatgggccg ttccttggtt taacaggggg aacatggctg tacaatgtga 1320
tctgtaacga gtctcccgtg cattgtttta gttatagagg gtgatgccat gtctcctgac 1380
ttcattccat ctcaaccaga aggagtttat ctgtatcctt tcccacaggc tctttggtct 1440
```

```
gctctggggg tggctcctgc agatggtggg gctgggggtt tttccacacc accctatatg   1500
ttcctttacc tggatacaga tacagcaagt accgggagcc tgaaaaggta agcttcaaac   1560
cactttcttt ttcttcagaa aattaaggcc ccttatttaa gagggaggaa agccaggaaa   1620
acttctgaga aaacactgtc aattagaaca gggctggccg ggagcagtga ctcatgtctg   1680
tagtcccagc actttgggtg gccgaggtgg gcagttcact tgaggtcatc agtttgaaac   1740
cagcctggcc aacatggtga aaccccatct ctactaaaag tacaaaaatt agccaggtat   1800
ggtggcgtgc acctgtaata ccagctactc aggagcctga ggcacgagaa ttgcttgaac   1860
ccaggaggca gaggttgcag tgagccatgt ttgtaccact gcactccagc ctgggctgga   1920
gactctgcct caaaacaaac aaaccaacca accacagggc tttatccagc tctgtagtag   1980
ggaaaggggg cttggaaagg cattatgctt ttgcaccaat aagcctcctc ttatgcaaga   2040
tgcatttta tttagcatat tcatgtttca cgcaatgatc agatctctga aatgtcagtt   2100
tggttctgtt ggaggtgtcc ctactctggt tagaataatc aagctgttca gactcactga   2160
gatcccttc ttttgtgtag tacatcgagt tagatggaga ccgtctgacc acggaggatc   2220
tggtcaactt ggaaaggga cgctacaaaa taaaggtatg gggagggagg ggaaagatgt   2280
cctctggcca tttttgttgc ccgtggaagt ctttaacgtg ctcagttctg atcaacattt   2340
tcctagctca ccccaacagc tgagaagagg gtgcagaaat ccaggaggt catagatagc   2400
atcataaaag agaaacagg tatcttttta tcttatgtt ataaatattt ttataaacaa   2460
acaaaaatcc ctgcatttaa ttgcataatg tctcttttta ttctagttgt ttacggtatt   2520
actacaggtt ttgggaaatt tgccagaact gtaattccta tcaataagct acagtaagtt   2580
taaaacacac atatgttcac gttccaccta ccctcatctt ttaaatattt ttcaacaagg   2640
gaaataattc acatttgccc caatttacag atcagaggat gaggcttggg ttaccttgca   2700
tgtgagttgg tattgaaaac ccaggctggc tggtttctcc cattgcctc cttctgtccc   2760
tccaaggatt tgaccatgat tcccttcatt ttcccagctg agggaacatt ttctcactgc   2820
aatgtatcta agagggtttt taccctttctg ttgcagggag cttcaggtca acttagtacg   2880
ctcacattct tcaggtaagt caaaacgttg ggtgcctcct ggatcttgtg tgattagatg   2940
aataaagcac agcacagtgt gagttatcca gttatagtca caaaaagtca gtttctcaaa   3000
acagcatttc aagaactagg tgccgaggtg agaaggggatg cagaaagaat cagctgagcc   3060
tcagaaaaag aaatgggcca ggtgaggga tggggttggt atgagaacac atgtcccatg   3120
ccatggagac actgttgcat tcaggaagg aaataaagcc tggaactcaa agaatgagtt   3180
aggatgggca tagtgagatg ggaaagactg tcaccaatca gcacccatca gatggtaaag   3240
aagttgtgct aaggactctg gatgctattc taaaggtgag tgggaggtca ggggttcact   3300
gaagcttccc aaaaagggga attgagaagg caaaactggg gtcttaacct ttgtcaggaa   3360
gatgggctc agacaagtca gacaggcagg agggagagta gtccaactac ctgagccgag   3420
aggagaaggt aatagcaggc tgggctacat atgggaaaga ttggagggag ggagggcagt   3480
tgtcaggaga caaaaaggag tttgctttc ttggagaaaa catcaattct gtttttgcagg   3540
tgttgggaaa ccactaagtc ctgagaggtg tcggatgctc ttggctttaa ggatcaatgt   3600
cttagccaaa ggatacagtg gcatttccct ggagaccctc aaacaagtca tagaaatgtt   3660
taatggtaat gcaatggctc cctagacgga acctctgtgg aggctggaca tgtaccacag   3720
ggtagaattg attggccaga tgctgaggaa tcacctgaga agacatgaaa taattgaaat   3780
gagtgggaaa tgccgttggc aaaaagtagg atagttagat gggggaagag gagaaagtcg   3840
atcagagatg cttactccta tgaactttaa cttattctgc aagacccttt ccctagcatt   3900
tgtcatcttc aagactagaa caggactctt aagtctgccc ttacattcaa gcctgcctag   3960
aagaaacttg gattaagtgg tacatgaata tggttagaaa tggcatga tatcaatgtc   4020
catcccaaag gccaattcag tagttctggt tggtgcctgg gaatctgaaa tcgtaatgtc   4080
ccccaggtga tggccagact tgcacactaa atccaacttt cttgcaaggg tagaacagaa   4140
atgcaaagag gttaatgact ccccttgtaat caagaagcca tgtagtggca ggatatgagg   4200
gaactcaact ctggagcttt cttcctggat aggaaaattc taatgtggaa accagatttg   4260
cagtgattgg aggtattgtc ccttctcaca ggtaaggaca agccttctag gtcagtggag   4320
actcagaact ctttgagggg aaggagaggg aggagaagca gtgctgaggc agtcacaaac   4380
agcaaaacac attcttgagt ttccatgtta tggacgcaag tggcacgtga ataggatctg   4440
ccaatgagtg gagagcaatt tcaatgagca gtctattgta tatacagggc tgtgctgaac   4500
agactagtag tgattccaac acctattttt actcctacct tggtctgcca tactatatag   4560
ccctaaaatc ccagatagta gcactccaac cttaaaccca cctgtacttt atgggggagt   4620
ctaaggcacc tctgagaatt ccccagcgtg aactatcagc cagaagttgg tctgtggatg   4680
gcactgccat acccgactga cattatttaa cagttggaaa aaatgctgct gtcaggaatc   4740
tgattttatt tcagaaaaat gaagcctctt ttttggtaac tttttggaa tttcttagaa   4800
aatggcacgt gttcattgat aaggggcagt ggagtgtaga ctgggtgact ggcaaaatga   4860
aaagactcag ttgcctatga cttctcttcc cctgggaaac cttgttaatg ctttggtgca   4920
ccacctcctt ctgaaacatt ttatattact tttccaatgt ttccaaacat tttccaatag   4980
ctgtgaatgg ctaaacttgg tcaaatgaat gtccttaat ttcatattta gataatttct   5040
aactattttt cctataataa acaatgaact gtaaaacaaa aacaaaaaca aaaaaaaaca   5100
gctagttcct gatcacttct tcaagatata ttgctaaaat ttctacaagt ggaagtacta   5160
ggttgaatta gagcacacag attttgaggg ctttgcatcc agaagtgtcc tccttccttc   5220
ttcttattta tttaggagac aggatcctgc tttgtcaccc aggctggagt gcagtggcac   5280
aatctcggct cactgcaacc tccacctcac gggttcaagt gattctccca tctcagcctt   5340
cccagtagtt gggactacag gcatgcacca ccatacttgg ctaattttg tatgttttgc   5400
agagacaggg tttcaccgtg ttgcccaggc tggtcttgaa ctcctgggct caagtgatat   5460
gcccgcctcg gcctcccaaa gtgctgggat tacaggcttg agccactgcg cctgccctt   5520
ctttccttct tgctgacttt ccctccagcc ctctgtctcc tcctgtctcc tcttttacctt   5580
tctctcttct tcctctccac ccccactcct cttttcttt ctataacaat tcatccaggt   5640
cccttacata ttagctgggt ttgaagaatt gtctttcccc aggtatctat gccataaagt   5700
gatagatatt ggaggcaggg tgtttgcggg ggcagtgggg gcactcactg gcaaagcaag   5760
gagagtcaga atgcagtact cttgaactaa ttgctgccta cttctctccc agcctcctgc   5820
ctgccctatg tcccagagaa aggaaccgtt ggtgccagtg gagaccttgc cccactctct   5880
catcttgctc ttgggctagt tggagaaggg aagatggtt ctccgaagag tggctgggct   5940
gatgctaaat acgtaagact cgtagcagct tctatctgca gcaattgccc caggttggac   6000
accaactgtg cttgcatgct tcgtatcacc tagtccttac aacagcccag tgagggagct   6060
cctactatcc ttactttaca gatgagacag cgaaagctta gaagtcagac taggcaagac   6120
tgttgttagc ttctatactc ggctgtcagc cttctgggtt tggtcatcac cttggtgaaa   6180
```

-continued

```
aggcataact gctactgtta atcccaacta tttatcctgc acctacaaca tttccagtgc    6240
ctagcaggga ggtcacacac tctcacaatt ttaattacga gctggtctca caggtgcagt    6300
ggtatggctc atagcactta ctatatggct tctggaaagc aggtttcatt tttccctaag    6360
ctcttaccct agtggctaat caaaaaagcc tgttttgat aaagctttgg tgttttcttc     6420
atctgtgtct gaatttcatt acagcagcat aaagcatcat ttaatgtatc atccctgatg    6480
aactgctggg agcttccctg atagtaagtg aaagggtag agggcccag aagaggaaac      6540
agctaaggaa atagataatc cttttgggga tgcagcttct agatcatctg tcttccgtgc    6600
aggcttgtct ttgattattt cactatggac agcgttttcc tccgaccacc ctcatacagc    6660
aatcaccctg acctttctaa acagcaaatt caagcatgtt ctggtgaaaa cttgtaatgc    6720
ttcccattgt cctcaggata aaggctaaac ttaaagtggc tttcaagggt cttgtttgtc    6780
acattagccc ctaatccctt ctatgtgtgg ttctgcattg cagaaactgg aggttgcttg    6840
gagaaggaat gttctgggca gagggtctgg tacaaatacg ttcttctctc tcctatttct    6900
gcttctgaaa catcttctag ggatcttttg aagccagaag ttcaagacca gcctgggcaa    6960
gaaagcgagg ctccgcctct acataaaata attaaaaaat atcctggca cagtagcatg      7020
tgcctgtagt cccagctact caggaggctg aggatcactt gagcccagga gttcaaggct    7080
gcagtgagct aggattgcac cactgtgctc gctctagcct gggttacaga dacaggtgtc    7140
taaaaaataa aaagaaaaat agaaaagccc tctaagaagc ttccgtctcc gctgctccac    7200
ttcctacctc tcgagttcct tgtgaccctc ctgtatgctc tcctagcaaa tgattgtttt    7260
ccactgcacc ccacccactt cccacatcct caagcactga atgtactatt actcagattg    7320
ccctgagctt gcctgtcttc attttgccta ctccctagacc gaccccaaca cccagaacag    7380
aatcagcct ctagctgata cttgaatctg tgaaattgac gtagtaaatg ggaccagctc      7440
tgtccttctc ttaccttaac ttccccttcc ttctttccta gagagacctt aacttaatga    7500
ctctctactt ctttttcttc aagggaagat tgttctgccc atcgcccct cgggattctg      7560
tctccatcta gtagagggaa ttttataatc ccctcttcat tggtgctcac acatgtgcca    7620
caaaaaccct gctctgaggt tttgccagta tttaaatgaa gcactaatga ggttagagga    7680
cttttaggt caagctctgg aggcaaggga gcgtgaactg ggaggagtcc agcctgagca     7740
caacacagat gcatgtatgt gtgtcagatg cctgcatgtc aggaggcagt ggtaaaaaag     7800
gtgaactgct aaggtagaaa ctgaaacacga aggacgtaga aaccaaaatt tagggtttgat   7860
tctatagaca atggagcccc tgatttcagt acaaaaatta attgaaagat aagtctgctt    7920
tcatgactaa agaacagaac tagagaatag accagagaac atgaatacag ccagttcctg    7980
taggtctcat ttcttataag atggacttt gggcataaag agctattatt ggattccata     8040
tgatattgga aataggctag tatttcattt gatacccatt ttcatatttt taatcattct    8100
ataggtgcta gaagcccatg gattgaaacc agttatttta aaaccaaaag aggtaaggaa    8160
actcaagaaa aatatgttca tagtgcatga gttttttatc atcagtatt ttcagtttta      8220
atctcagcct caatcattcc ttaaatgcaa cttgcatgtt tgcttaaagt tcatccctga    8280
agaagggca actccgtaag aatttaaaag attctttatg ccaggcatgg tggcggatgc     8340
ctgtaatcct agcactttgg gaagccgaga caggtggatt gcctgagctc aggagtttga    8400
gaccagcctg ggcaacatgg tgaaaccat ctctacccgc ccccccgcc ccgccaaaaa       8460
agacaaaaat tagccaggca tggtggcgca cacttgtaat cccagctacc ctggaggcta    8520
aggtgggagg atcacttgag ccctggaggt caaggctgca gggagccatg atcgcaccac    8580
tgcacaccag cctgagcaac acagtaagac cctgtctcaa aaaagaaaaa aagattcttc     8640
atgccacaat gcataggggg tcttcttagga acttaaaaact tcaaatcgag ttctgttagg   8700
atctctgaga gatagatgtt ctcagcccaa attccttaga atgctctaag taagagtcct    8760
tggaccagaa ttgggttttt ttggatgtct catctataac agtaagaatt taaggaagaa    8820
atgcaaccta atgcactaaa gattttatgt gcagtctaca ctccagagct gcattgctgc    8880
tttgggaatg tggatactta atgagtgttt catttgccag atttgtgctt acgagttcac    8940
atatgatagc acttattctt caagggctta aataaacatt actgtcccgc actttagaaa    9000
acataaacat aattttttat gtttatgact ggctaatttt tctcttatga aagcaaaaga    9060
tacaaaatcc acgggtatgt aggttcgtta caataatcac agtaggaaac tttgctctct    9120
cccccgacag ggcctggcac tcatcaatgg gacgcagatg atcacatccc tgggctgtga    9180
agctgtagag cgagccagtg ctattgcacg gcaggctgac attgtggcag ccctgacct    9240
tgaggtgctg aagggcacca ccaaagcctt tgacactgtg cagcagggtt cttccttttg    9300
gttgttattc attcaaccag aggtggtggg gcggggtggc tgagatcttt agacacagaa    9360
gtggtgggg caggtagtag ggaaggagaa aacccaagtg cctgtggcgt acccagtgtg     9420
ctgcctcttc atctaggcta tggcacaact gatctttgaa agaactgcaa tttacagata    9480
cacacagccc ggaagttgag tgacttgcct gagagcaccc agggatctgg gtgtgtcaag    9540
ctctgtgctg tcttaggaat cttttttacag gacttaggag tcctgtaaaa aggagtagga   9600
ttagagttgg tcccgactag aaaattgggg aagaaaaact gtcgaattgg tagcttattt    9660
agaaagtagt gaattttgac gacctcccaa ctataatatg aaaaagggca gaacattgtc    9720
taaaagtgaa tgagttaaat taggccactg tagggctccc tcctgttatt cgccctgttc    9780
ctttaaggta ggcccagtgt cttgagtgga attcccagtg gtctcaacat atagtttgct    9840
ctcagatatt taaagtagaa ggagtcaagt caataaggaa atcgtgcttt tcggagttaa    9900
gtttctaatt ctgagtggtg gctaaggacc cctgggactt tgagggctg tgtcagcacc     9960
gtagatgtc ctgaaccatt gatggtcatt tgttctaata tcagaattac tcgacctgtc     10020
atggtggctc atgcctgtaa tcccagcact tgggaggcc aaggtaggag gatcgctaga     10080
gcccaggagt ttgaaaccag cctggggaac gtagtgagac cccatcttt aaaaaaaata     10140
aataaatgga attattcaga cttttctcc ttcatcaatt ctagacattc atgctcttcg     10200
acctcaccgt gggcaaattg aagttgcttt tcggtttcgg tcactcttgg actcagatca    10260
ccacccatca gaaatagcag gtctgaccat gtttatggga gtgacctatt tggttacgtg    10320
ttttgtgaaa agaattggta acatgatccc tgtctcatcc cctccacctc ttccacagag    10380
agtcacaggt tctgtgatcg cgtccaggat gcatacacct tgcgctgctg tccacaggta    10440
aaataaagaa aaaaaaaag gtcaataaaa aatgccaata aagttttct ttccccaggt      10500
tcaggatgaa aaattttaaa ataggaaagt gttagaaaaa catgtaatgg tcaactatag    10560
tccaaatttc ttactgtctc tatgaaaagt tatgtatatt ttacctttat gtgtgcaatt    10620
gttgaaagt ttctattcta tatggtgaac tatttgtttt cttttgattg ttcaacctac     10680
tttcagagga caacctcttt tttttttttt ttttttttt gagacagaca accaacaaat    10740
aacctctttg atttggagac agagtctcac tctgtcaccc tggctggagt acagtggcat    10800
gatctctgtt cactacaatc ttcacctccc aggttcaagt gattctcctg cctcaacctc    10860
ccgagtagat gggattacag gcatgtgcca ccatgcctaa ttttttgtatt tttagtagag    10920
```

```
atgggtctc accatgttgg ccaagctggt ctcgaacccc tgacctcaaa tgatccacct   10980
gcctcagcct cccaaagtgc tgggattaca ggcgtgagga ccgtcccggg cccagacaac   11040
ctcttatgtt gattcagtgc cctaactttt aaaaattctt agtaataaaa tcataaccag   11100
ttagtagagt tgtactgttt ctccctgtta agatgaaact ttaaccagat agtcagaggt   11160
gtttacagga aagtcttaat tatatcattt tgaaactcag gtgcatagta atggttatac   11220
cttacttgca ttttatgggc aatataaatt attttaaatg aatttgtgat gcttaacttt   11280
aaattaaaaa tgcagatgac ctgggttggc attaggcatc tgtattacag atgtgtaatt   11340
tacatatgac agttagagag ccagtcatct caataaacca tattttggtc tgtgccaaat   11400
ttcagtctat ggtgtaatag agagtcctcc ctagaataaa taccctcatt tcccttagt   11460
cagcaagtta tcttttctag ctagcttatt gagcaataga tcaaacacc tatgggtaag   11520
aattgccaaa ttagatctac aggaagatta agtcctgatg taagacttcc ctgatatttt   11580
aataacgata gcagattcta tgtgacaggc accattatca ctgtctttca tttattaatt   11640
catttaatct tcccaactat aagatactct ttctcccatt ttgcaatggg gaaactgagg   11700
cacagaatta agtatcttgc ccacgatcac acagacagat aattacttcc ttgacttctg   11760
ggagaaacca gagccaggtg ctgctttata gcattgtggc tatttctggg gtttgtacag   11820
cgtagctgcc ttatgtgtga gcatcttcta atgtgatgcc ttcgtgctta atgaacttta   11880
ccgccttgga taatagctac catttgagta atctctgcga gtcacatcta agaatttgtt   11940
tgcattattt tatgtacttc tcaaaagcca taagtgctat tgtctctttt ctaagtcttc   12000
ctatctttta actataaacc taaggaactt gcccaagtcc taccactaac ctgggagtga   12060
atctgcctgt gtctagagtt ggcattcttc ctcccacacc atgctgcttt gtatagattg   12120
atctaatgtg aatatatatg ataatgaatt tattctaatt tgtttcagtg aaaacccaaa   12180
agaattataa caaaattatc ttcagttcaa ataatttcca tggttataac tttaaaataa   12240
gatcttctgt attctttata actttaagat aagatcttct atattctttt aagaatattg   12300
gtactcttca ggtaatcaaa tgggtcatat accttatttt gattgtattt taggtccatg   12360
gtgtggtgaa tgatacaata gcatttgtga agaacatcat taccacagaa ctgaacagcg   12420
caacagataa tcctgtatct tttgattgta tactaacctg caattataga attgcagctg   12480
gtaattttag gatctactga aacaatcatt ttgtgtagct tctcagttcc attgctccat   12540
ttcacagagt aaatgaatca gtacctgagg ctcagaggtt aactgacttt ctccaggtca   12600
gagctggtaa gtggcagagg tgacctgtga acttactctc aggttccaag tctaacatgc   12660
tgtactttca aatggacct attcaagatt taagaagata tttccagcat tggctgacat   12720
gtttcctgaa gacactggcc ctaaaaccca ctgccaaggt tgttggtgga agggtgaaga   12780
cgtgggtcac aaatgtgatt gcagaaatgc tgaacaattt atgcaggcct ctctgctttg   12840
agtgagagca gtttgcatta tgcagaggtc agccttttaa cacttaccaa agtattgatt   12900
aaagagttat ggcttcctca tcctgaggtt tttggcattt tttttttgt ttattttag   12960
acggagtctc actctgtctc ctaggctgga gtgcagtggt gccatctcgg ctctctgcaa   13020
cctctgcctc acgggttcaa gcgattctcc tgcctcagcc tcctgagtag ctggaattac   13080
aggcatgtgc cagcaggcct ggctaatatt tgtatttta gtagacag ggttttgctg   13140
tgttggccag gctggtctca aactcctgac ctcaagtgat ccacctgcct cggcctccca   13200
aagtgccggg attacaggtg tgagcgacta cacccagccc ccatcatgag ttttattttg   13260
tcatgcgcac tttgctcaaa ttagtgcttt tgcgtttgtt caaagaaata gtaaaactga   13320
ttccattct caaggatgga ggtcctctct taatggtgtg gcttatctca gagccatctg   13380
gttttctct ggaatgttcc atgatggctc agttccccag atgttgaggt gatcagtcag   13440
gagtcacact ggcacagttt tcatggagat agcactgcct ctgaagataa tcaaacgact   13500
ttggaatcta ttttttcctat tccacatctg cctcagttct gaatcctaga gaaagtgctg   13560
agtaagcagc cccaaaagca ggtcacaggc tgagttagaa gatggttatg tgatagctcc   13620
ataaggtttc ccatgagatg gcttttgtat gtatgtgttt tttgacaagc ttacttcaga   13680
atgtgtgttt tatgttctct cacattgttt tacactgaag tcaaacccac actaaataag   13740
cctcagaaat tgtgggtctc tccattcacc tcaataccac cccatccccc agatggaata   13800
gtagtttta tgaactctat gtagtcttat ctcacgtacc agtcttttca ctgtagggaa   13860
gaggtatcta ttctacattt acatcattgc tttttaaggg tatctcatag tttttagaaa   13920
ttaccattca attactgaat atggggcagg ggataattaa ttcctcacta aattcttctg   13980
ctaccaattg cctcagcaag aatttcagcc aaaagtctttt tatttttttc aattaaagat   14040
tgctaattat tgataaattt ccaataggct aatatttggg agttctcttg caatactgct   14100
gttacctgaa agaatatgtg tctcaatttt ctgttgcaga tacggagccc catcacacat   14160
gctggatatt atgggagtta aattctaatt gttttaatct aatagccaac aaacaaattt   14220
ggaacaacta gaggacaata aaaacatgtc taagttctaa attgatgcag aattccattg   14280
ctataggggat tcagagaatg gagaagaggc caagaccaag gagctagacc caatgggctc   14340
acagttacac atgcagaaca gagtaatcca cacttgagta ggttaatgta acacatacat   14400
ctctaactct ttcaaagtta gaaactttct tgcacacagc aagttctcag ttaataggta   14460
atgaatattc ttgagcccaa gaggcaaaga ttagctcttt agaaccagga agaaggatct   14520
gttactgcct tttcctgggt gcttgctggt ttaagtaaag tgcatgatgg aatagaatta   14580
tctgaggctg ggtttggtgg ctcacacctg taatcccagc actttgggag gccaaggtgg   14640
gctgatcact tgaggccaag agtccaagac cagcctggcc aacatggcaa aaccctgtct   14700
ctactaaaaa tacaaaattt aactgggtgt gatggtgcat gcctgtaatc ccagctactc   14760
aggaggctga ggcacaagaa atcacttgaa cccgggaggc agaggtcgca gtgagccgag   14820
atggcgcccc tgcactccag cctgggtgac agaatgatac agaaataaa aaaagaatta   14880
cctcagagta ataatattca gcaaatttaa acttgccacc tacttaaaat ggattcatga   14940
ggacatattg gccaccatct gctgttgaac gctgacacca gattactgag taaagaattt   15000
gaaaattttc tcaaaattga ttgttccaga cattttggta gttgctcatc agcagagttt   15060
cccattcaac agattcttct atggaacaca aatttgcagt gcccattgaa gaaacagaag   15120
ttgctttcaa acagatgtgt tggtctctgt ttttagtttc aggctataaa cctttttgagg   15180
gcaggtacta accaccaggt tagtacagtt atggtgcttt agaatctaat ctcaagaaa   15240
aacatcattt caaggttcat gttttttcag cctccaaatt gggtgtacat gatccacctt   15300
taaggctttc tgttttttgc ttttgtgccc ctttatatct cttgcaggaa gacttgctc   15360
tttccctcca ccccacattt gtacacagac tgccacctcc acgttaaaaa agaaggcagg   15420
aaggggttgt acttgaagtg accagcaaac attatcttca agcttaacc tcttttgaaa   15480
gatggtcttt gccaataggg gagagacagt ttctggagga aacttccatg gtgaataccc   15540
agccaaagta agcttttaa aactgctcct gacccagaag gcacatttca atataggctg   15600
actaaatgga gaccctcttt caggccctag actacttggc cattggcatc catgaacttg   15660
```

```
ctgcaatcag tgagagaaga atcgagcggc tctgcaatcc ctccctcagt gagctgcctg   15720
ccttcctggt ggctgaaggt ggtctgaact ctgggttcat gatagctcac tgcacggcag   15780
cagcccttgg taaggacact gccccttttcc cagaacacac gcccgtccat ctaagggtct   15840
ttccatttca cctagaagta tcaaatgtgg tctgtgagtg agatctaact tttcaccact   15900
tttatctgca tcctagttct ctcagtgcaa aggtaacgag ttaactctaa tatttttcag   15960
aaaaaaatag tttaaaaact tcgatactgt tatgctgaaa tataataata caataataag   16020
gctgtaatga acaatttctc tgtggaaagc aatttgacat tgcatatgaa cttcatctct   16080
atagcttttt tccaaatctc catttgaaga ctattggaaa aagactaaga tggttatagt   16140
taatggtgaa acttgaacca acctataatt aaactttgaa cttttaaacc tataattaaa   16200
ctttggattc atttcactag atataacaac cactaaaaac ataaagatgt tattgcaaca   16260
ttaaaaaaat gctataagaa atcaggatac cctctgtgaa gattgagctt caatatagtt   16320
tatttctgac tcaagattgt aagagacaga ttaacacatc agaacagtgc ctggcactaa   16380
gtaagtacta agggcctcat ttatgttcat tcacttaatt gcacaattgt cacctgaggt   16440
aagtgctatt attgttatct atagatgaat atctgaagat ctgagagtta agtgacttgc   16500
ccaatattgc acagctagca agatgtaaag cagaattcaa accctgaatt ttggcatgca   16560
aaaatgtgct tttacttcaa ttaatgagga tctcattta atcaatactt aatcctaaaa   16620
tagggttgtc aaatttaaca aaaacacagg atgactagtt aaatttgaat tatttgggac   16680
atacttgtac tacaaaaatt atttttttaa tctaaaatca aaatttaact gggcatcctt   16740
tactttatct aacaacccta ccctaaaagg caggatagca tgagttatta catgcgtaga   16800
tgctagatca gaagcccagc tctgccattt actagctctg tgagcctctt tatcctgttg   16860
atcctcaatt tacacctgca taaatggag atcagttttac ctaaggggt tgtttggagg   16920
attaaatgaa ttgatgtata taaagcctgg cacatcataa gcactaaaaa aatactagtt   16980
gctattaata ttattcccaa cgaacacaaa taaccaacta agagccactg aattcacctc   17040
ctctgaccgg tatcttctat ttgcttactt gcttattaat aaaataccc tttaacaggt   17100
agaaatttct cacaataacg tagtagtggg ggagtagtca ttgatttcta gagaacagga   17160
tggacattgg gaagcctcat ttgaatatgt tttagtttcc caagctgcct attgaggttg   17220
tttggcttgc tttcattgta gtaaaattag tgttttttctt ttttttggcc ttgtaagtta   17280
tctttccgaa caagccttac cacagtttac ttatctgtat agtccacagt ttagggtcca   17340
aggacttggg acttacagtg ctgaaacctg gaaagtcctt ggccaaccaa catgaccttg   17400
acaaagtagc atgaccctag tttaaagcga gatcatctta ggatgcgatc ccatgcagca   17460
tagaaaacaa ctgaagcctc acccatgacc actcttaaag ccagagaaag aggagaaag   17520
actttgagtc tgacctttcc tgacttctaa gctagggtga gggaacttca taacctaagt   17580
ttttgctact tatagtgtag tcctcagacc aacaatatgg ccatcacctg agagctcgtt   17640
agaacagcag aatttcacgc cccacccaaa gctcagtata tttgttataa caaggtccct   17700
gagtgattca tgtgcactgg aaagcttgag agtcccatgt cttggtcctc cctagaattc   17760
ccccacctcc cagatatttc tggcagtcat cgagcccctg tttacatcca tttatgtcat   17820
ccttgaacac tctgaagtgt taaatcttct tgcccaagat ttatgggtcc agcctcagtc   17880
cccaaatgcc acatcggaat tctggtgtca caaccaaatt gacgtcaagt acctgaaaat   17940
ggccatcatg tctcttttctc ccctagtctc cctggcatgc tatatgcttc ccaggttgtc   18000
atcttggcct tgttatatta gaattcccag ttctcccatc tccgtcttac ctcagaactc   18060
actattgctt tagagtcctc acttggggaa aaaaaatgac ctgcttcctt ttcccaaagc   18120
agctttctac catcaggtgc ttggataatg tccaagatct tctggagagt gtatcccatg   18180
ctgtggagca ctctgctgga gccacgggtc ctttagacag ctcatcctgt gaggagcaat   18240
tcttaactgg cactggtctc ttgcagtttc tgagaacaag gctctgtgcc atccctcgtc   18300
tgttgactcc ctctccacca gcgcagccac ggaggaccac gtctccatgg gaggatgggc   18360
agcaaggaaa gccctcaggg tcatcgagca tgtggagcaa ggtaatgctg atgagttcgg   18420
ggtgggcggg ctgcctgata gaccactgtg cccgtggttc tcaagtggga tctcccacca   18480
gcaacatcag catcacctgg aaacttgtta ggaaggcaga ctctcaggcc tccttgcagg   18540
ctggctaatt cagacactcc aggaggagag cggagcaatc tgtgtttaac gaaccctcca   18600
ggtgattctg atcttcacta aagattaaga accaaggaac catgcagaac taagctggtc   18660
ctttggcggtg cttttttttt ctcttttttt tttttttttt ttgaggcagg atctctatct   18720
gccacccagg ctgagtgca gtgttgcaac aatagctcac tgcagccttg aactcccagg   18780
ctcaagtgat cctccttcct tagtctccta agtaactgac acctcaggca agcaccacca   18840
cacctgggta attttttaaat ttttgtaaa gatggggtct tgctgtgttg ccttggctgg   18900
tctcaaactc ttggcctcaa gcgatcctcc cacctcaccc ccaaagtggt ttttttttta   18960
atgagacttt taaaacatat tcaaagtgga gagaagagta ccatgaactc tcacacccca   19020
ccttgattca acagcacatt caatttatga agtacactat gaactctagt gagtgcagac   19080
aggtcacagt gggagaggat gaagttgtgg aattcacggt ggacctggaa gcaatttctc   19140
atcttctagt ccagtatccc caccccgcaa ttcatatgga attggaaacc acgagatgta   19200
aagcatcttg atgaaatgca tacaattatt taatagaact ggggctcaag atgaggatca   19260
gctcttcttt ctgacttcct tccctaccca catgacccaa acttggccaa caaaccttg   19320
ttagaggatg tgaatggggg acatggcaga ttttgctagt gcagatgaat gggcagcttc   19380
ctgggtaggt gtgcaggtct ggtaattatt caggtaaatg tctcaattct cccctttctca   19440
gcattaaaga tatagtcaag gggttagaaa acaggttaaa atgccaagta aataccaaag   19500
caacttcatt ctaccaatag acagagaaca aaccatctgt tagttgggtg gtgatgggt   19560
tcaactttgg gaaatccaca ttccttaagc atgaagtcag actttcataa gctaccctct   19620
tggaatttct tgtttcagtg ctggccatcg agctccttgc agcctgccag gcatagagt   19680
ttctacgtcc cctgaaaaca accactccgc tggagaaggt ctatgacctg gtgcgctctg   19740
ttgtaaggta agatcaaaca ggtctctgaa aattacatca gttcagcact gtgaaccctg   19800
gcagggtttc atgtttggct gatgggcgga tgtgctctcc ctgtaggccc tggataaaag   19860
atcgcttcat ggccccggac atcgaggcag cccacaggct gctcctggag cagaaggcaa   19920
gctggctcct tggcttgttt cttaatttt aattgttaca ggaaagcaaa gtcggggatg   19980
gagaaacatt gccttattct attgttttct ggccattcct tgggaatgag caaaaaggta   20040
tttgagcaac aacttgcagc accactaaga agccatataa taaacactaa gtgcaccagg   20100
gtgcagccaa cggttgaata tctaaggatt agaaacagaa atggattta aatgagtttt   20160
tgggacaata ttcatgggga aaaaaataag atgtcaggtt cattgatgcc tccccacccc   20220
tgcaagatgt cctctttgat tcaaaagtgc gttcccttct gggtgatgct atcacaacta   20280
ccaccactgg gtgcaatggc tgcgtagacc tggagagaaa accaaggccc gggtgtttac   20340
ttcagaagac tttcggtctg tctagtgctc tggtgagatg cgggttttct tttcttgcat   20400
```

```
atttccactg gttacattga ccgtatactc agctgccagg tacagatgcc cagcatgctg    20460
gcttatcttt taaatatcgt ttttgaagtg ctttaaacct tttgaataac ttgtgggtgt    20520
tatgttccct agaatcgctt gatttcctta aaacagttgc tctgctctgg ggcagtgatt    20580
tttccctgtg attttcacac ccattatttc taagcatgcc ctgcactctg gatggggaag    20640
ctgcttgcct gctgccaact ttggtgctag gagggaggta tacgagaggt tagcctttaa    20700
gagtattcat ttgctaaggt cataaaaaat aataggaaag gctccttggc tgtcagtggc    20760
aatcagttaa aaagcagata taaaccaaaa acagggcctt aatttcattc aatttaaaaa    20820
aaaatttttt tagagatgcg ggtcttgcta tgttgccaag gctggactca aactcctggg    20880
ctcaagtgat cctcccactt tggcttcttg agtagctggg actacaggca catgccacca    20940
tgcccgtcca gggccttact ttgagatgat gttatgctta agaaaaaaaa aaaaaaagaa    21000
aaaagaggtt ggtgggtggg aggcaaaagc taaccaagga tctgaggcag tgcctctcca    21060
acattaaagt ggctatgaat ctgctgggca tcttgttaaa atgcaggtgt ggattcagta    21120
ggtctgggtg aaggccaaga ttctgacttg tcccaggtga tgctgatact gcaggggcac    21180
aggccacgct ttgagtagca gggtcaaagg aacagagcac ctgtggcatg gaaataaggc    21240
aatagggaaa tacaattcac tgccttttac catttaaggc ttgctttaga aaacacacag    21300
gtccaggcca tgtgtggtgg ctcacgcctg taatcccagc actttgggaa gctgtggtgg    21360
gtggatcact tgaggccaga aattcgagac cagcctggcc aacatggtga aaccccatct    21420
ctgctaaaaa tacaaaaatt agctgggcct ggtggcatgc acctgtaatc ccagctactc    21480
aggaggctga ggcacaagaa ttgcttgaac ctggaaggtg gaggttgcag tgagctgaga    21540
tcatgctact gcactccagc ctgggcgaca gagtgagact ctgtctcaca aaaaaagaaa    21600
aaaaacaaaa aaacaagaaa aaaaccacat aggtactgtt aagaccctgg agcaactatc    21660
cttcactcta tccacactga attctctggg ttttgttatt tgcttgcttg ttttgcttag    21720
gaaaagtatg cagcttaaaa tctttatgat gactttagaa agttttggac tttgtatatt    21780
tacagtcttt aatgcaacca aagactaatt gacacaggtc atgtgtcaaa tggcttaaaa    21840
taaaagcaag caaacagcag ctgtgtctgg tcatgtatag agtatgtttt gacttcggat    21900
gaagttgatg tttaatagca tgtggaaaca atgtcgtcaa tatttcaact ttgttttgtc    21960
cttgcttttc aggtttggga agtagctgct ccatacattg aaaaatacag aatggagcat    22020
attccagaat caagacctct ttctccaaca gccttttcac tgcaatttct gcacaagaaa    22080
tccaccaaaa tcccggagtc tgaggacctt taatgggctt tgtcatgaag tagcagatga    22140
gagggcagtc agtttagcac aaagcaatac taggctgaag gagagacctg agaacttttcc   22200
taggtagatc aatccattgt atcattcagt tcttctaaag cctacgttgg ttaagctgat    22260
ggcagtatta tagttgctaa attcagcact gtgttcctgt tgtcgtggtt caagacccac    22320
caggtatttt cagattataa aacttttctt tctttcttaa cagtttcaac aggccactca    22380
ctcttaaggg tgagaagaat aaccacaatt gtatgtgcct gttttttact cttagcatta    22440
gatgaattca aatttggaaa cagattgata gcaattttt ctaaaaacat tagacttttg    22500
ttaaccttttt tttttttttt taaatttgct tcaacaagct ctccaccagt tgactttctt    22560
tggctaattt tactttgcat gatatgcctt aatatgcctt cataaataac cattttaagt    22620
cataatttgt ccttaagctg cttttttctt ctattaaattg gatcatagta aagagtagtc    22680
aatagggtct tcagctatta attgtagagg tgattaaaac caacaaggag tttcatgtgc    22740
aaaggagata aggaatgaat ataaagattg ctatttgggt ggctcttatt aaactgtgta    22800
ttttgtactt atcactacac gtatcccccta aatgcttaca tgggagtttg aggttagtat    22860
tttcactttcc ttggtgttag tactctattc acattcttat tgtaaccttc ctcatttcac    22920
agataaggaa tcttttgggga ttaaccaacc tccttttctgt aatggtaatc attaaaataa    22980
gtcctattga taaaggtcag atggagccct agagtgtatt actgcatcta ttttttttccc    23040
cgagaagata aaggaccttc agggatggct taagtgtatc tgtccagatg aaggatgggt    23100
cacatgacct cttggcttcc caagtctaag ctctgtgact ttgcaccagt gtgtgcatat    23160
atgtgcaagg ccctttcaagt ggtctgaaac cgtggctcta aaaaccacag ctggtggaga    23220
ggaggacaga cacacttgcc accttgccta cctaattgcc atctaaaatg ggccgaacag    23280
tggatttcac aatagagttt tcacccttta gatttacaac ctgtcaggtg gaaactgaag    23340
tgaaaactgc tgcacacagc aattcaggga gcaaaaaatg tgctgaggag actgtttacc    23400
taaaggttgt tcttggtgct attccttgtc aaaatgtgaa cacacacaaa tgaggtttgg    23460
gcattgtcat ccgtgggctg ccattgagcc agtaaccccc agtggtctca tggtgctctt    23520
cgctccagtt tggggaatgc tggattcttt cagcccctgc agccctccag gtcaaaatga    23580
cactttgtca ctgagttttc tacacagctc tattagtaac tgacagcaca cgccttcaag    23640
ggaacttcaa gggaaacatg gaataaacta agtctcaatt gcc                     23683

SEQ ID NO: 2          moltype = DNA   length = 23683
FEATURE               Location/Qualifiers
source                1..23683
                      mol_type = genomic DNA
                      organism = Homo sapiens
SEQUENCE: 2
agataaagac aggaacatgg tgtttataag ctgcccttaa tggcagagaa cacagacaga      60
aacgagggaa gagagagaaa ttggggaccc tgaagaaagg gggccaggag caggtaggtg     120
ccatcaggga caagaacagc acctcccagg gtgggagacc ccaggccttt ctggcagcag     180
gtctggatgg aaagtggaca ggaggctcac ccgtctgcat cccctgctcc tgcccctgct     240
cggctacaaa aaccaagggg acagcaggta cctcaataaa tatttgtcca atgcatgaat     300
gagtaaaggt gaaggagggg gagtggtttg aaagtctatt ctcatccttc cagctgacca     360
caccccggta gccactcctg cataaagctc tccctcctg tgaccagctg aggacctcag     420
gctgcagcgg agccatgccc agatacacgt tgcacgtacg tggggaatgg ctggcagtgc     480
cctgccagga cgcgcagctc actgtgggct ggctgggccg ggaggccgtg aggcgctata     540
tcaagaataa gcccgacaat ggtggcttca cctccgtgga tgacgcgcac ttccttgtgc     600
gccggtgcaa gggcctgggc ctgctggaca acgaggaccg gctcgaggtg gccctagaga     660
acaacaagtt cgtggaagtg ggtgagtggc tgcaggagga ggccgcgaac gggtgcggtt     720
tggcctggct tagtctttgc agcattgaac ccccacctca gggaaaatga tgagcagagg     780
tcaggcttgc cgaggctggc cctgtgcagg cacatgccac gcctctgggg atcttaagtc     840
ctcacacaac cctgtgagat gggtaggatt ctcctccacc tctgatggag gagaaaatcag    900
agaggaggta acttacccag actccagcag ctagtaagta acaaagacta gactggtact     960
caaggctgca ggtctgaatc cctttgcagt gactgaatca ttttgaggtt attttgcctt    1020
```

```
tcgaaagaat ccaccccac ccccagactg gaggccggca gcatagcatc agttcagatt   1080
ttgaagaaaa taaagctggg aatggggatg gaagtggaat tctgtcttga actttcatct   1140
aaaccctgg tctctgccct gacacctacc tttctgcttt ttgctctcct cctacataaa    1200
gatgctaaga ccacatgaaa ccatctgaag cagttttaaa gcagccattt ctatagaatt   1260
catgggccaa tgatgggccg ttccttggtt taacagggga aacatggctg tacaatgtga   1320
tctgtaacga gtctcccgtg cattgtttta gttatagagg gtgatgccat gtctcctgac   1380
ttcattccat ctcaaccaga aggagtttat ctgtatcctt tcccacaggc tctttggtct   1440
gctctggggg tggctcctgc agatggtggg gctgggggtt tttccacacc ccctatatg    1500
ttccttacc tggatacaga tacagcaagt accgggagcc tgaaaaggta agcttcaaac    1560
cactttcttt ttcttcagaa aattaaggcc ccttatttaa gagggaggaa agccaggaaa   1620
acttctgaga aaacactgtc aattagaaca gggctggccg ggagcagtga ctcatgtctg   1680
tagtcccagc actttgggtg gccgaggtgg gcagttcact tgaggtcatc agtttgaaac   1740
cagcctggcc aacatggtga aaccccatct ctactaaaag tacaaaaatt agccaggtat   1800
ggtggcgtgc acctgtaata ccagctactc aggagcctga gcacgagaga ttgcttgaac   1860
ccaggaggca gaggttgcag tgagccatgt tgtaccact gcactccagc ctgggctgga    1920
gactctgcct caaacaaac aaaccaacca accacagggc tttatccagc tctgtagtgg    1980
ggaaagggg cttggaaagg cattatgctt ttgcaccaat aagcctcctc ttatgcaaga    2040
tgcattttta tttagcatat tcatgtttca cgcaatgatc agatctctga aatgtcagtt   2100
tggttctgtt ggaggtgtcc ctactctggt tagaataatc aagctgttca gactcactga   2160
gatcccttc ttttgtgtag tacatcgagt tagatggaga ccgtctgacc acggaggatc    2220
tggtcaactt gggaaaggga cgctacaaaa taaaggtatg gggagggagg ggaaagatgt   2280
cctctggcca tttttgttgc ccgtggaagt cttaacgtg ctcagtttcg atcaacattt    2340
tcctagctca ccccaacagc tgagaagagg gtgcagaaat ccaggaggt catagatagc    2400
atcataaaag agaaaacagg tatctttta tctttatgtt ataaatattt ttataaacaa    2460
acaaaaatcc ctgcatttaa ttgcataatg tctcttttta ttctagttgt ttacggtatt   2520
actacaggtt ttgggaaatt tgccagaact gtaattccta tcaataagct acagtaagtt   2580
taaaacacac atatgttcac gttccaccta ccctcatctt ttaaatattt ttcaacaagg   2640
gaataattc acatttgccc caatttacag atcagaggat gaggcttggg ttaccttgca    2700
tgtgagttgg tattgaaaac ccaggctggc tggtttctcc cattgccttc cttctgtccc   2760
tccaaggatt tgaccatgat tccccttcatt tcccgactg agggaacatt ttctcactgc   2820
aatgtatcta agagggtttt tacctttctg ttgcagggag cttcaggtca acttagtacg   2880
ctcacattct tcaggtaagt caaaacgttg ggtgcctcct ggatcttgtg tgattagatg   2940
aataaagcac agcacagtgt gagttatcca gttatagtca caaaaagcta gtttctcaaa   3000
acagcatttc aagaactagg tgccgaggtg agaagggatg cagaaagaat cagctgagcc   3060
tcagaaaaag aaatgggcca ggtggaggga tggggttggt atgagaacac atgtcccatg   3120
ccatggagac actgttgcat tcagggaagg aaataaagcc tggaactcaa agaatgagtt   3180
aggatgggca tagtgagatg ggaaagactg tcaccaatca gcacccatca gatggtaaag   3240
aagttgtgct aaggactctg gatgctattc taaaggtgag tgggaggtca ggggttcact   3300
gaagcttccc aaaaaggga attgagaagg caaaactggg gtcttaacct ttgtcaggaa   3360
gatgggctc agacaagtca gacaggcagg agggagagta gtccaactac ctgagccgaa    3420
aggagaaggt aatagcaggc tgggctacat atgggaaaga ttggagggag ggaggcaat    3480
tgtcaggaga caaaaaggag tttgctttc ttggagaaaa catcaattct gttttgcagg    3540
tgttgggaaa ccactaagtc ctgagaggtg tcggatgctc ttggcttaa ggatcaatgt    3600
cttagccaaa ggatacagtg gcatttccct ggagaccctc aaacaagtca tagaaatgtt   3660
taatggtaat gcaatggctc cctagacgga acctctgtgg aggctggaca tgtaccacag   3720
ggtagaattg attggccaga tgctgaggaa tcacctgaga agacatgaaa taattgaaat   3780
gagtgggaaa tgccgttggc aaaaagtagg atagttagat gggggaaagg gagaaagtcg   3840
atcagagatg cttactccta tgaactttaa cttattctgc aagacccttt ccctagcatt   3900
tgtcatcttc aagactagaa caggactctt aagtctgccc ttacattcaa gcctgcctag   3960
aagaaacttg gattaagtgg tacatgaata tggttagaaa aattgcatga tatcaatgtc   4020
catcccaaag gccaattcag tagttctggt tggtgcctgg gaatctgaaa tcgtaatgtc   4080
ccccaggtga tggccagact tgcacactaa aatccaactt cttgcaaggg tagaacagaa   4140
atgcaaagag gttaatgact ccccttgtaat caagaagcca tgtagtggca ggatatgagg   4200
gaactcaact ctggagcttt cttcttggat aggaaaattc taatgtggaa accagatttg   4260
cagtgattgg aggtattgtc cccttctcaca ggtaaggaca agccttctag ctcagtggag   4320
actcagaact ctttgagggg aaggagaggg aggagaagca gtgctgaggc agtcacaaac   4380
agcaaaacac attcttgagt ttccatgtta tggacgcaag tggcacgtga ataggatctg   4440
ccaatgagtg gagagcaatt tcaatgagca gtctattgta tatacagggc tgtgctgaac   4500
agactagtag tgattccaac acctattttt actcctacct tggtctgcca tactatatag   4560
ccctaaaatc ccagatagta gcactccaac cttaaaccca cctgtacttt atggggagt    4620
ctaaggcacc tctgagaatt ccccagcgtg aactatcagc cagaagtgg tctgtgggatg    4680
gcactgccat acccgactga cattatttaa cagttgaaaa aaatgctgct gtcaggaatc   4740
tgattttatt tcagaaaaat gaagcctctt ttttggtaac ttttggggaa tttcttagaa   4800
aatggcacgt gttcattgat aagggggcagt ggagtgtaga ctggtgatg ggcaaaatga    4860
aaagactcag ttgcctatga cttctcttcc cctgggaaac cttgttaatg ctttggtgca   4920
ccacctcctt ctggaacatt ttatattact tttccaatgt ttccaaacat tttccaaatag  4980
ctgtgaatgg ctaaacttgg tcaaatgaat gtccttaat ttcatattta gataattct     5040
aactatttt cctataataa acaatgaact gtaaaacaaa aacaaaaaca aaaaaaaca     5100
gctagttcct gatcacttct tcaagatata ttgctaaaat ttctacaagt ggaagtacta   5160
ggttgaatta gagcacacag attttgaggg ctttgcatcc agaagtgtcc tccttcttc    5220
ttcttattta tttaggagac aggatcctgc tttgtcaccc aggctggagt gcagtggcac   5280
aatctcggct cactgcaacc tccacctcac gggttcaagt gattctccca tctcagcctt   5340
cccagtagtt gggactacag gcatgcacca ccatacttgg ctaattttg tatgttttgc    5400
agagacaggg tttcaccgtg ttgcccagtg tggtcttgaa ctcctgggct caagtgatat   5460
gcccgcctcg gcctcccaaa gtgctgggat tacaggcttg agccactgcg cctggccttt   5520
cttttccttct tgctgacttt cccctccagcc ctcctttcct ccctgtctcc tctttaccttt  5580
tctctcttct tcctctccac ccccactcct cttttttcttt ctataacaat tcatccaggt   5640
cccttacata ttagctgggt ttgaagaatt gtctttcccc aggtatctat gccataaagt   5700
gatagatatt ggaggcaggg tgtttgcggg ggcagtgggg gcactcactg gcaaagcaag   5760
```

```
gagagtcaga atgcagtact cttgaactaa ttgctgccta cttctctccc agcctcctgc  5820
ctgccctatg tcccagagaa aggaaccgtt ggtgccagtg gagaccttgc cccactctct  5880
catcttgctc ttgggctagt tggagaaggg aagatgtggt ctccgaagag tggctgggct  5940
gatgctaaat acgtaagact cgtagcagct tctatctgca gcaattgccc caggttggac  6000
accaactgtg cttgcatgct tcgtatcacc tagtccttac aacagcccac tgagggagct  6060
cctactatcc ttactttaca gatgagacag cgaaagctta gaagtcagac taggcaagac  6120
tgttgttagc ttctatactc ggctgtcagc cttctgggtt tggtcatcac cttggtgaaa  6180
aggcataact gctactgtta atcccaacta tttatcctgc acctacaaca tttccagtgc  6240
ctagcaggga ggtcacacac tctcacaatt ttaattacga gctggtctca caggtgcagt  6300
ggtatggctc atagcactta ctatatggct tctggaaagc aggtttcatt tttccctaag  6360
ctcttacccct agtggctaat caaaaaagcc tgttttgat aaagctttgg tgttttcttc  6420
atctgtgtct gaatttcatt acagcagcat aaagcatcat ttaatgtatc atccctgatg  6480
aactgctggg agcttccctg atagtaagtg aaaggggtag agggcccag aagaggaaac  6540
agctaaggaa atagataatc cttttgggga tgcagcttct agatcatctg tcttccgtgc  6600
aggcttgtct ttgattattt cactatggac agcgttttcc tccgaccacc ctcatacagc  6660
aatcaccctg acctttctaa acagcaaatt caagcatgtt ctggtgaaaa cttgtaatgc  6720
ttcccattgt cctcaggata aaggctaaac ttaaagtggc tttcaagggt cttgtttgtc  6780
acattagccc ctaatccctt ctatgtgtgg ttctgcattg cagaaactgg aggttgcttg  6840
gagaaggaat gttctgggca gagggtctgg tacaaatacg ttcttctctc tcctatttct  6900
gcttctgaaa catcttctag ggatcttttg aagccagaag ttcaagacca gcctgggcaa  6960
gaaagcgagg ctccgcctct acataaaata attaaaaaat tatcctggca cagtagcatg  7020
tgcctgtagt cccagctact caggaggctg aggatcactt gagccagga gttcaaggct  7080
gcagtgagct aggattgcac cactgtgctc gctctagcct gggttacaga gacaggtgtc  7140
taaaaaataa aaagaaaaat agaaaagccc tctaagaagc ttccgtctcc gctgctccac  7200
ttcctacctc tcgagttcct tgtgacccte ctgtatgctc tcctagcaaa tgattgtttt  7260
ccactgcacc ccacccactt cccacatcct caagcactga atgtactatt actcagattg  7320
ccctgagcct gcctgtcttc attttgccta ctcctagacc gaccccaaca cccagaacag  7380
aatccagcct ctagctgata cttgaatctg tgaaattgac gtagtaaatg ggaccagctc  7440
tgtccttctc ttaccttaac ttccccttcc ttctttccta gagagacctt aacttaatga  7500
ctctctactt cttttctttc aagggaagat tgttctgcct atcgccccct cgggattctg  7560
tctccatcta gtagagggaa ttttataatc ccctcttcat tggtgctcac acatgtgcca  7620
caaaaaccct gctctgaggt tttgccagta tttaaatgaa gcactaatga ggttagagga  7680
cttttttaggt caagctctgg aggcaaggga gcgtgaactg ggaggagtcc agcctgagca  7740
caacacagat gcatgtatgt gtgtcagatg cctgcatgtc aggaggcagt ggtaaaaaag  7800
gtgaactgct aagtagaaa ctgaacacga aggacgtaga aaccaaaatt tagggttgat  7860
tctatagaca atggagcccc tgatttcagt acaaaaatta attgaaagat aagtctgctt  7920
tcatgactaa agaacagaac tagagaatag accagagaac atgaatacag ccagttcctg  7980
taggtctcat ttcttataag atggactttt gggcataaag agctattatt ggattccata  8040
tgatattgga aataggctag tatttcattt gatacccatt ttcatatttt taatcattct  8100
ataggtgcta gaagcccatg gattgaaacc agttattta aaaccaaaag aggtaaggaa  8160
actcaagaaa aatatgttca tagtgcatga gttttattt atgcagtatt ttcagttta  8220
atctcagcct caatcattcc ttaaatgcaa cttgcatgtt tgcttaaagt tcatccctga  8280
agaagggca actccgtaag aatttaaaag attctttatg ccaggcatgg tggcggatgc  8340
ctgtaatcct agcactttgg gaagccgaga caggtggatt gcctgagctc aggagtttga  8400
gaccagcctg ggcaacatgg tgaaacccat ctctaccgc cccccccgcc ccgccaaaaa  8460
agacaaaaat tagccaggca tggtggcgca cacttgtaat cccagctacc ctggaggcta  8520
aggtggagg atcacttgag ccctggaggt caaggctgga ggttgcagtg agccaccac  8580
tgcacaccag cctgagcaac acagtaagac cctgtctcaa aaaagaaaaa aagattcttc  8640
atgccacaat gcataggggg tctcttagga acttaaaact tcaaatcgag ttctgttagg  8700
atctctgaga gatagatgtt ctcagcccaa attccttaga atgctctaag ctaagagtct  8760
tggaccagaa ttgggttttt ttggatgtct catctataac agtaagaatt taaggaagaa  8820
atgcaaccta atgcactaaa gattttatgt gcagtctaca ctccagagct gcattgctgc  8880
tttgggaatg tggatactta atgagtgttt catttgccag atttgtgctt acgagttcac  8940
atatgatagc acttattctt caagggctta aataaacatt actgtcccgc actttagaaa  9000
acataaacat aatttttttat gtttatgact ggctaatttt tctcttatga aagcaaaaga  9060
tacaaaatcc acgggtatgt aggttcgtta caataatcac agtaggaaac tttgctctct  9120
cccccgacag ggcctggcac tcatcaatgg gacgcagatg atcacatccc tgggctgtga  9180
agctgtagag cgagccagtg ctattgcacg gcaggctgac attgtggcag ccctgacct  9240
tgaggtgctg aagggcacca ccaaagcctt tgacactggt cagcagggtt cttccttttg  9300
gttgttattc attcaaccag aggtggtggg gcggggtggc tgagatcttt agacacagaa  9360
gtggtggggg caggtagtag ggaaggagaa aacccaagtg cctgtggcgt acccagtgtg  9420
ctgcctcttc atctaggcta tggcacaact gatctttgaa agaactgcaa tttacagata  9480
cacacagccc ggaagttgag tgacttgcct gagagcaccc agggatctgg gtgtgtcaag  9540
ctctgtgctg tcttaggaat cttttttacag gacttaggaa tcctgtaaaa aggagtagga  9600
ttagagttgg tcccgactag aaaattgggg aagaaaaact gtcgaattgg tagcttattt  9660
agaaagtagt gaattttgac gacctcccaa ctataatatg aaaaagggca gaacattgtc  9720
taaaagtgaa tgagttaaat taggccactg tagggctccc tcctgttatt cgccctgttc  9780
ctttaaggta ggcccagtgt cttgagtgga attcccagtg gtctcaacat atagtttgct  9840
ctcagatatt taaagtagaa ggagtcaagt caataaggaa aatcgtgctt tcggagttaa  9900
gtttctaatt ctgagtggtg gctaaggacc cctgggactt tgagggctg tgtcagcacc  9960
gtagatggtc ctgaaccatt gatggtcatt tgttctaata tcagaattac tcgacctggc  10020
atggtggctc atgcctgtaa tcccagcact tgggaggcc aagtaggag gatcgctaga  10080
gcccaggagt ttgaaaccag cctgggggac gtagtgagac cccatctttt aaaaaaaata  10140
aataaatgga catattcaga cttttctcc ttcatcaatt ctagacattc atgctcttcg  10200
acctcaccgt gggcaaattg aagttgcttt tcggtttcgg tcactcttgg actcagatca  10260
ccacccatca gaaatagcag gtctgaccat gtttatggga gtgaccatt tggttacgtg  10320
ttttgtgaaa agaattggta acatgatccc tgtctcatcc cctccacctc ttccacagag  10380
agtcacaggt tctgtgatcg cgtccaggat gcatacacct tgcgctgctg tccacaggta  10440
aaataaagaa aaaaaaaag gtcaataaaa aatgccaata aagttttct ttccccaggt  10500
```

```
tcaggatgaa aaattttaaa ataggaaagt gttagaaaaa catgtaatgg tcaactatag    10560
tccaaatttc ttactgtctc tatgaaaagt tatgtatatt ttaccttttat gtgtgcaatt   10620
gttgtaaagt ttctattcta tatggtgaac tatttgtttt cttttgattg ttcaacctac   10680
tttcagagga caacctcttt tttttttttt tttttttttt gagacagaca accaacaaat   10740
aacctctttg atttggagac agagtctcac tctgtcatcc tggctggagt acagtggcat   10800
gatctctgtt cactacaatc ttcacctccc aggttcaagt gattctcctg cctcaacctc   10860
ccgagtagat gggattacag gcatgtgcca ccatgcctaa ttttttgtatt tttagtagag   10920
atggggtctc accatgttgg ccaagctggt ctcgaacccc tgacctcaaa tgatccacct   10980
gcctcagcct cccaaagtgc tgggattaca ggcgtgagga ccgtcccgg cccagacaac    11040
ctcttatgtt gattcagtgc cctaactttt aaaaattctt agtaataaaa tcataaccag   11100
ttagtagagt tgtactgttt ctccctgtta agatgaaact ttaaccagat agtcagaggt   11160
gtttacagga aagtcttaat tatatcattt tgaaactcag gtgcatagta atggttatac   11220
cttacttgca ttttatgggc aatataaatt attttaaatg aatttgtgat gctcaacttt   11280
aaattaaaaa tgcagatgac ctgggttggc attaggcatc tgtattacag atgtgtaatt   11340
tacatatgac aattagagag ccagtcatct caataaacca tatttggtc tgtgccaaat    11400
ttcagtctat ggtgtaatag agagtcctcc ctagaataaa taccctcatt tcccctttagt  11460
cagcaagtta tctttctag ctagcttatt gagcaataga tcaaaacacc tatgggtaag    11520
aattgccaaa ttagatctac aggaagatta agtcctgatg taagacttcc ctgatatttt   11580
aataacgata gcagattcta tgtgacaggc accattatca ctgtctttca tttattaatt   11640
catttaatct tcccaactat aagatactct ttctcccatt ttgcaatggg gaaactgagg   11700
cacagaatta agtatcttgc ccacgatcac acagacagat aattacttcc ttgacttctg   11760
ggagaaaacca gagccaggtg ctgcttttata gcattgtgc tatttctggg tgtttgtacag  11820
cgtagctgcc ttatgtgtga gcatcttcta atgtgatgcc ttcgtgctta atgaacttta   11880
ccgccttgga taatagctac catttgagta atctctgcga gtcacatcta agaatttgtt   11940
tgcattattt tatgtacttc tcaaaagcca taagtgctat tgtctctttt ctaagtcttc   12000
ctatcttta actataaacc taaggaactt gcccaagtcc taccactaac ctggagtga    12060
atctgcctgt gtctagagtt ggcattcttc ctcccacacc atgctgcttt gtatagattg   12120
atctaatgtg aatatatg ataatgaatt tattctaatt tgtttcagtg aaaacccaaa      12180
agaattataa caaaattatc ttcagttcaa ataatttcca tggttataac tttaaaataa   12240
gatcttctgt attctttata actttaagat aagatcttct atattcttt aagaatattg    12300
gtactcttca ggtaatcaaa tgggtcatat acctttatttt gattgtattt taggtccatg  12360
gtgtggtgaa tgatacaata gcatttgtga agaacatcat taccagaa ctgaacagcg     12420
caacagataa tcctgtatct tttgattgta tactaacctg caattataga attgcagctg   12480
gtaattttag gatctactga aacaatcatt ttgtgtagct tctcagttcc attgctccat   12540
ttcacagagt aaatgaatca gtacctgagg gttgaggtt aactgactttt ctccaggtca   12600
gagctggtaa gtggcagagg tgacctgtga acttactctc aggttccaag tctaacatgc   12660
tgtactttca aaatggacct attcaagatt taagaagata tttccagcat ggctgacat    12720
gtttcctgaa gacactggcc ctaaaaccca ctgccaaggt tgttggtgga agggtgaaga   12780
cgtgggtcac aaatgttgatt gcagaaatgc tgaacaattt atgcaggcct ctctgctttg  12840
agtgagagca gtttgcatta tgcagaggtc agccttttaa cacttaccaa agtattgatt   12900
aaaagagttat ggcttcctca tcctgaggtt tttggcattt ttttttttgt ttattttag   12960
acggagtctc actctgtctc ctaggctgga gtgcagtggt gccatctcgg ctctctgcaa   13020
cctctgcctc acgggttcaa gcgattctcc tgcctcagcc tcctgagtag ctggaattac   13080
aggcatgtgc cagcaggcct ggctaatatt tgtatttta gtagagacag gttttgctg     13140
tgttggccag gctggtctca aactcctgac ctcaagtgat ccacctgcct cggcctccca   13200
aagtgccggg attacaggtg tgagcgacta cacccagccc ccatcatgag ttttttatttg  13260
tcatgcgcac tttgctcaaa ttagtgcttt tgcgtttgtt caaagaaata gtaaaactga   13320
ttccatttct caaggatgga ggtcctctct taatgtgtg gcttatctca gagccatctg    13380
gtttttctct ggaatgttcc atgatggctc agttccccag atgttgaggt gatcagtcag   13440
gagtcacact ggcacagttt tcatggagat agcactgcct ctgaagataa tcaaacgcct   13500
ttggaatcta ttttttcctat tccacatctg ctccagttct gaatcctaga gaaagtgctg  13560
agtaagcagc cccaaaagca ggtcacaggc tgagttagaa gatggttatg tgatagctcc   13620
ataaggtttc ccatgagatg gcttttgtat gtatgtgttt tttgacaagc ttacttcaga   13680
atgtgtgttt tatgttctct cacattgttt tacactgaag tcaaacccac actaaataag   13740
cctcagaaat tgtgggtctc tccattcacc tcaataccac cccatccccc agatggaata   13800
gtagtttta tgaactctat gtagtcttat ctcacgtacc agtctttca ctgtagggaa     13860
gaggtatcta ttctacattt acatcattgc ttttaagggg tatctcatag ttttagaaa    13920
ttaccattca attactgaat atggggcagg ggataattaa ttcctcacta aattcttctg   13980
ctaccaattg cctcagcaag aatttcagcc aaaagtcttt tattttttc aattaaagat    14040
tgctaattat tgataaattt ccaataggct aatatttggg agttctcttg caatactgct   14100
gttacctgaa agaatatgtg tctcaatttt ctgttgcaga tacggagccc catcacacat   14160
gctggatatt atgggagtta aattctaatt gttttaatct aatagccaac aaacaaattt   14220
ggaacaacta gaggacaata aaaacatgtc taagttctaa attgatgcag aattccattg   14280
ctatagggat tcagagaatg gagaagaggc caagaccaag gagctgcaac caatgggctc   14340
acagttacac atgcagaaca gagtaatcca cacttgagta ggtaatgta acacatatcat   14400
ctctaactct ttcaaagtta gaaactttct tgcacacagc aagttctcag ttaataggta   14460
atgaatattc ttgagcccaa gaggcaaaga ttagctcttt agaaccagga agaaggatct   14520
gttactgcct tttcctgggt gcttgctggt ttaagtaaag tgcatgatgg aatagaatta   14580
tctgaggctg ggtttggtgg ctcacacctg taatcccagc actttgggag gccaaggtgg   14640
gctgatcact tgaggccaag agtccaagac cagcctggcc aacatggcaa accctgtct    14700
ctactaaaaa tacaaaattt aactgggtgt gatggtgcat gcctgtaatc ccagctactc   14760
aggaggctga ggcacaagaa atcacttgaa cccgggaggc agaggtcgca gtgagccgag   14820
atggcgcccc tgcactccag cctgggtgac agaatgatac agaaaataaa aaaagaatta   14880
cctcagagta ataattca gcaaattaa acttgccacc tacttaaaat ggattcatga     14940
ggacatattg gccaccatct gctgttgaac gctgacacca gattactgag taaagaattt   15000
gaaaattttc tcaaaattga ttgttccaga cattttggta gttgctcatc agcagagttt   15060
cccattcaac agattcttct atggaacaca aatttgcagt gccattgaa gaaacagaag    15120
ttgctttcaa acagatgtgt tggtctctgt ttttagtttt aggctataaa ccttttgagg   15180
gcaggtacta accaccaggt tagtacagtt atggtgcttt agaatctaat ctcaagagaa   15240
```

```
aacatcattt caaggttcat gttttttcag cctccaaatt gggtgtacat gatccacctt   15300
taaggctttt tgtttttgc ttttgtgccc ctttatatct cttgcaggaa gacttgtctc   15360
tttccctcca ccccacattt gtacacagac tgccacctcc acgttaaaaa agaaggcagg   15420
aaggggttgt acttgaagtg accagcaaac attatcttca agccttaacc tcttttgaaa   15480
gatggtcttt gccaataggg gagagacagt ttctggagga aacttccatg gtgaataccc   15540
agccaaagta agcttttaa aactgctcct gacccagaag gcacatttca atataggctg   15600
actaaatgga gaccctcttt caggccctag actacttggc cattggcatc catgaacttg   15660
ctgcaatcag tgagagaaga atcgagcggc tctgcaatcc ctccctcagt gagctgcctg   15720
ccttcctggt ggctgaaggt ggtctgaact ctgggttcat gatagctcac tgcacggcag   15780
cagcccttgg taaggacact gccccttcc cagaacacac gcccgtccat ctaagggtct   15840
ttccatttca cctagaagta tcaaatgtgg tctgtgagtg agatctaact tttcaccact   15900
tttatctgca tcctagttct ctcagtgcaa aggtaacagg ttaactctaa tattttcag    15960
aaaaaaatag tttaaaaact tcgatactgt tatgctgaaa tataataata caataataag   16020
gctgtaatgg acaatttctc tgtggaaagc aatttgacat tgcatatgca cttcatctct   16080
atagctttt tccaaatctc catttgaaga ctattgaaa aagactaaga tggttatagt    16140
taatggtgaa acttgaacca acctataatt aaactttgaa cttttaaacc tataattaaa   16200
ctttggattc atttcactag atataacaac cactaaaaac ataaagatgt tattgcaaca   16260
ttaaaaaaat gctataaga atcaggatac cctctgtgaa gattgagctt caatatagtt   16320
tatttctgac tcaagattgt aagagacaga ttaacacatc agaacagtgc ctggcactaa   16380
gtaagtacta agggcctcat ttatgttcat tcacttaatt gcacaattgt cacctgaggt   16440
aagtgctatt attgttatct atagatgaat atctgaagat ctgagagtta agtgacttgc   16500
ccaatattgc acagctagca agatgtaaag cagaattcaa accctgaatt ttggcatgca   16560
aaaatgtgct tttacttcaa ttaatgagga tctcatttta atcaatactt aatcctaaaa   16620
tagggttgtc aaatttaaca aaaacacagg atgactagtt aaatttgaat tatttgggac   16680
atacttgtac tacaaaaatt atttttttaa tctaaaatca aaatttaact gggcatcctt   16740
tacttatct aacaacccta ccctaaaagg caggatagca tgagttatta tacgtagta    16800
tgctagatca gaagcccagc tctgccattt actagctctg tgagcctctt tatcctgttg   16860
atcctcaatt tacacctgca taaaatggag atcagtttac ctaaggggt tgtttggagg    16920
attaaatgaa ttgatgtata taaagcctgg cacatcataa gcactaaaaa aatactagtt   16980
gctattaata ttattcccaa cgaacacaaa taaccaacta agagccactg aattcacctc   17040
ctctgaccgg tatcttctat ttgcttactt gctattaat aaaataccc tttaacaggt     17100
agaaatttct cacaataacg tagtagtggg ggagtagtca ttgatttcta gagaacagga   17160
tggacattgg gaagcctcat ttgaatatgt tttagtttcc caagctgcct attgaggttg   17220
tttggcttgc tttcattgta gtaaaattag tgttttctt tttttggccc ttgtaagtta    17280
tctttccgaa caagccttac cacagtttac ttatctgtat agtccacagt ttagggtcca   17340
aggacttggg acttacagtg ctgaaacctg gaaagtcctt ggccaaccaa catgaccttg   17400
acaaagtagc atgaccctag tttaaagcga gatcatctta ggatgcgatc ccatgcagca   17460
tagaaaacaa ctgaagcctc acccatgacc actcttaaag ccagagaaag aggagaagag   17520
actttgagtc tgacctttcc tgacttctaa gctagggtga ggaacttca taacctaagt    17580
ttttgctact tatagtgtag tcctcagacc aacaatatgg ccatcacctg agagctcgtt   17640
agaacagcag aatttcacgc cccacccaaa gctcagtata tttgttataa caaggtccct   17700
gagtgattca tgtgcactgg aaagcttgag agtcccatgt cttggtcctc cctagaattc   17760
ccccacctcc cagatatttc tggcagtcat cgagcccctg tttacatcca tttatgtcat   17820
ccttgaacac tctgaagtgt taaatcttct tgcccaagat ttatgggtcc agcctcagtc   17880
cccaaatgcc acatcggaat tctggtgaca caaccaaatt gacgtcaagt acctgaaaat   17940
ggccatcatg tctctttctc ccctagtctc cctggcatgc tatatgcttc ccaggttgtc   18000
atcttggcct tgttatatta gaattcccag ttctcccatc tccgtcttac ctcagaactc   18060
actattgctt tagagtcctc acttgggaa aaaaaatgac ctgcttcctt ttcccaaagc    18120
agctttctac catcaggtgc ttggataatg tccaagatct tctggagagt gtatcccatg   18180
ctgtggagca ctctgtggaa gccacgggtc ctttagacag ctcatcctgt gaggagcact   18240
tcttaactgg cactggtctc ttgcagtttc tgagaacaag gctctgtgcc atccctgtgc   18300
tgttgactcc ctctccacca gcgcagccac ggaggaccac gtctccatgg gaggatgggc   18360
agcaaggaaa gccctcaggg tcatcgagca tgtggagcaa ggtaatgctg atgagttcgg   18420
ggtggcgggc ctgcctgata gaccactgtg cccgtggttc tcaagtggga tctcccacca   18480
gcaacatcag catcacctgg aaacttgtta ggaaggcaga ctctcaggcg tccttgcagg   18540
ctggctaatt cagacactcc aggaggagag cggagcaatc tgtgtttaac gaaccctcca   18600
ggtgattctg atcttcacta aagattaaga accaaggaac catgcagaac taagctggtc   18660
ctttggctgg cttttttttt ctcttttttt tttttttt ttgaggcagg atctctatct     18720
gccacccagg ctggagtgca gtgttgcaac aatgctcac tgcagccttg aactcccagg    18780
ctcaagtgat cctccttcct tagtctccta agtaactgaca acctcaggca agcaccacca   18840
cacctggta atttttaaat tttttgtaaa gatgggtct tgctgtgttg ccttggctgg     18900
tctcaaactc ttggcctcaa gcgatcctcc cacctcaccc ccaaagtggt ttttttttta   18960
atgagacttt taaaacatat tcaaagtgga gagaagagta ccatgaactc tcacaccca    19020
ccttgattca acagcacatt caatttatga agtacactat gactctagt gagtgcagac    19080
aggtcacagt gggagaggat gaagttgtgg aattcacggt ggacctggaa gcaatttctc   19140
atcttctagt ccagtatccc cacccgcaa ttcatatgga attggaaacc acgagatgta    19200
aagcatcttg atgaaatgca tacaattatt aatagaact ggggctcaag atgaggatca    19260
gctcttcttt ctgacttcct tccctaccca catgacccaa acttggccaa caaacctttg   19320
ttagaggatg tgaatggggg acatggcaga ttttgctagt gcagatgaat gggcagcttc   19380
ctgggtaggt gtgcaggtct ggtaattatt caggtaaatg tctcaattct ccccttctca   19440
gcattaaaga tatagtcaag gggttagaaa acaggttaaa atgcaactga ataccaaag    19500
caacttcatt ctaccaatag acagagaaca aaccatctgt tagttgggtg gtgatgggtg   19560
tcaactttgg gaaatccaca ttccttaagc atgaagtcag actttcataa gctaccctct   19620
tttctt tgtttcagtg ctggccatcg agctccttgc agcccgccag ggcatagagt        19680
ttctacgtcc cctgaaaaca accactccgc tggagaaggt ctatgacctg gtgcgctctg   19740
ttgtaaggta agatcaaaca ggtctctgaa aattacatca gttcagcact gtgaaccctg   19800
gcagggtttc atgtttggct gatgggcgga tgtgctctcc ctgtaggccc tggataaaag   19860
atcgcttcat ggccccggac atcgaggcag cccacaggct gctcctggag cagaaggcaa   19920
gctggctcct tggcttgttt cttaatttt aattgttaca ggaaagcaaa gtcggggatg    19980
```

-continued

```
gagaaacatt gccttattct attgttttct ggccattcct tgggaatgag caaaaaggta    20040
tttgagcaac aacttgcagc accactaaga agccatataa taaacactaa gtgcaccagg    20100
gtgcagccaa cggttgaata tctaaggatt agaaacagaa atggatttta aatggagttt    20160
tgggacaata ttcatgggga aaaaataag atgtcaggtt cattgatgcc tccccacccc    20220
tgcaagatgt cctcttttgat tcaaaagtgc gttcccttct gggtgatgct atcacaacta    20280
ccaccactgg gtgcaatggc tgcgtagacc tggagagaaa accaaggccc gggtgtttac    20340
ttcagaagac tttcggtctg tctagtgctc tggtgagatg cgggttttc tttcttgcat    20400
atttccactg gttacattga ccgtatactc agctgccagg tacagatgcc cagcatgctg    20460
gcttatcttt taaatatcgt ttttgaagtg cttttaaacct tttgaataac ttgtgggtgt    20520
tatgttccct agaatcgctt gatttcctta aaacagttgc tctgctctgg ggcagtgatt    20580
tttccctgtg attttcacac ccattattttc taagcatgcc ctgcactctg gatggggaag    20640
ctgcttgcct gctgccaact tggtgctag aggggaggta tacgagaggt tagcctttaa    20700
gagtattcat ttgctaaggt cataaaaaat aataggaaag gctccttggc tgtcagtggc    20760
aatcagttaa aaagcagata taaaccaaga tctgaggcag aatttcattc aatttaaaaa    20820
aaaattttt tagagatgcg ggtcttgcta tgttgccaag gctggactca aactcctggg    20880
ctcaagtgat cctcccactt tggcttcttg agtagctggg actacaggca catgccacca    20940
tgcccgtcca gggccttact tgagatgat gttatgctta agaaaaaaaa aaaaaaagaa    21000
aaaagaggtt ggtgggtggg aggcaaaagc taaccaagga tctgaggcag tgcctctcca    21060
acattaaagt ggctatgaat ctgctgggca tcttgttaaa atgcaggtgt ggattcagta    21120
ggtctgggtg aaggccaaga ttctgacttg tcccaggtga tgctgatact gcaggggcac    21180
aggccacgct ttgagtagca gggtcaaagg aacagagcac ctgtggcatg gaaataaggc    21240
aataggggaaa tacaattcac tgccttttac catttaaggc ttgctttaga aaacacacag    21300
gtccaggcca tgtgtggtgg ctcacgcctg taatcccagc actttgggaa gctgtggtgg    21360
gtggatcact tgaggccaga aattcgagac cagcctggcc aacatggtga aaccccatct    21420
ctgctaaaaa tacaaaaatt agctgggcct ggtggcatgc acctgtaatc ccagctactc    21480
aggaggctga ggcacaagaa ttgcttgaac ctggaaggtg gaggttgcag tgagctgaga    21540
tcatgctact gcactccagc ctgggcgaca gagtgagact ctgtctcaca aaaaaagaaa    21600
aaaaacaaaa aaacaagaaa aaaaccacat aggtactgtt aagaccctgg agcaactatc    21660
cttcactcta tccacactga attctctggg ttttgttatt tgcttgcttg ttttgcttag    21720
gaaaagtatg cagcttaaaa tctttatgat gactttttgga ctcagctgaa tttgtatatt    21780
tacagtcttt aatgcaacca aagactaatt gacacaggtc atgtgtcaaa tggcttaaaa    21840
taaaagcaag caaacagcag ctgtgtctgg tcatgtatag agtatgtttt gacttcggat    21900
gaagttgatg tttaatagca tgtggaaaca atgtcgtcaa tatttcaact ttgttttgtc    21960
cttgctttc aggtttggga agtagctgct ccatacattg aaaaatacag aatggagcat    22020
attccagaat caagacctct ttctccaaca gcctttcac tgcaatttct gcacaagaaa    22080
tccaccaaaa tcccggagtc tgaggaccttt taatgggctt tgtcatgaag tagcagatga    22140
gagggcagtc agtttagcac aaagcaatac taggctgaag gagagacctg agaactttcc    22200
taggtagatc aatccattgt atcattcagt tcttctaaag cctacgttgg ttaggctgat    22260
ggcagtatta tagttgctaa attcagcact gtgttcctgt tgtcgtggtt caagacccac    22320
caggtatttt cagattataa aacttttctt tctttcttaa cagttcaac aggccactca    22380
ctcttaaggg tgagaagaat aaccacaatt gtatgtgcct gttttttact cttagcatta    22440
gatgaattca aatttggaaa cagattgata gcaatttttt ctaaaaacat tagacttttg    22500
ttaaccttt ttttttttt taaattgct tcaacaagct ctccaccagt tgacttttctt    22560
tggctaatttt tactttgcat gatatgcctt aatatgcctt cataaataac cattttaagt    22620
cataatttgt ccttaagctg ctttttttctt ctattaattg gatcatagta aagagtagtc    22680
aatagggtct tcagctatta attgtagagg tgattaaaac caacaaggag tttcatgtgc    22740
aaaggagata aggaatgaat ataaagattg ctatttgggt ggctcttatt aaactgtgta    22800
ttttgtactt atcactacac gtatccccca aatgcttaca tgggagtttg aggttagtat    22860
tttcacttcc ttggtgttag tactctattc acattcttat tgtaaccttc ctcatttcac    22920
agataaggaa tctttgggga ttaaccaacc tcctttctgt aatggtaatc attaaaataa    22980
gtcctattga taaaggtcag atggagccct agagtgtatt atgcatcta ttttttttcc    23040
cgagaagata aaggaccttc agggatggct taagtgtatc tgtccagatg aaggatgggt    23100
cacatgacct cttggcttcc caagtctaag ctctgtgact ttgcaccagt gtgtgcatat    23160
atgtgcaagg cccttcaagt ggtctgaaac cgtggctcta aaaccacag ctggtggaga    23220
ggaggacaga cacacttgcc accttgccta cctaatttgcc atctaaaatg ggccgaacag    23280
tggatttcac aatagagttt tcacccttta gatttacaac ctgtcaggtg gaaactgaag    23340
tgaaaactgc tgcacacagc aattcaggga gcaaaaaatg tgctgaggag actgtttacc    23400
taaaggttgt tcttggtgct attccttgtc aaaatgtgaa cacacacaaa tgaggtttgt    23460
gcattgtcat ccgtgggctg ccattgagcc agtaaccccc agtggtctca tggtgctctt    23520
cgctccagtt tggggaatgc tggattcttt cagccctgc agccctccag gtcaaaatga    23580
cactttgtca ctgagttttc tacacagctc tattagtaac tgacagcaca cgccttcaag    23640
ggaacttcaa gggaaacatg gaataaacta agtctcaatt gcc                      23683

SEQ ID NO: 3              moltype = DNA   length = 23683
FEATURE                   Location/Qualifiers
source                    1..23683
                          mol_type = genomic DNA
                          organism = Homo sapiens
SEQUENCE: 3
agataaagac aggaacatgg tgtttataag ctgcccttaa tggcagagaa cacagacaga     60
aacgagggaa gagagagaaa ttggggaccc tgaagaaagg gggccagcag caggtaggtg    120
ccatcaggga caagaacagc acctcccagg gtggagacc ccaggccttt ctggcagcag     180
gtctggatgg aaagtggaca ggaggctcac ccgtctgcat cccctgctcc tgcccctgct    240
cggctacaaa aaccaaaggg acagcaggta cctcaataaa tatttgtcca atgcatgaat    300
gagtaaaggt gaaggagggg gagtggtttg aaagtctatt ctcatccttc cagctgacca    360
caccccggta gccactcctg cataaaagctc tcccctcctg tgaccagctg aggacctcag    420
gctgcagcga agccatgccc agatacacgt gcacgtacg tggggaatgg ctggcagtgc    480
cctgccagga cgcgcagctc actgtgggct ggctgggccg ggaggccgtg aggcgctata    540
tcaagaataa gcccgacaat ggtggcttca cctccgtgga tgacgcgcac ttccttgtgc    600
```

```
gccggtgcaa gggcctgggc ctgctggaca acgaggaccg gctcgaggtg ccctagaga   660
acaacgagtt cgtggaagtg ggtgagtggc tgcaggagag ggccgcgaac gggtgcggtt   720
tggcctggct tagtctttgc agcattgaac ccccacctca gggaaaatga tgagcagagg   780
tcaggcttgc cgaggctggc cctgtgcagg cacatgccac gcctctgggg atcttaagtc   840
ctcacacaac cctgtgagat gggtaggatt ctcctccacc tctgatggag gagaaatcag   900
agaggaggta acttacccag actccagcag ctagtaagta acaaagacta gactggtact   960
caaggctgca ggtctgaatc cctttgcagt gactgaatca ttttgaggtt attttgcctt  1020
tcgaaagaat ccacccccac ccccagactg gaggccggca gcatagcatc agttcagatt  1080
ttgaagaaaa taaagctggg aatgggatgg gaagtggaat tctgtcttga actttcatct  1140
aaaccctgg tctctgccct gacacctacc tttctgcttt ttgctctcct cctacataaa  1200
gatgctaaga ccacatgaaa ccatctgaag cagttttaaa gcagccattt ctatagaatt  1260
catgggccaa tgatgggccg ttccttggtt taacagggg aacatggctg tacaatgtga  1320
tctgtaacga gtctcccgtg cattgtttta gttatagagg gtgatgccat gtctcctgac  1380
ttcattccat ctcaaccaga aggagtttat ctgtatcctt tcccacaggc tctttggctt  1440
gctctggggg tggctcctgc agatggtggg gctgggggtt tttccacacc ccctatatg  1500
ttcctttacc tggatacaga tacagcaagt accgggagcc tgaaaaggta agcttcaaac  1560
cacttttcttt ttcttcagaa aattaaggcc ccttatttaa gagggaggaa agccaggaaa  1620
acttctgaga aaacactgtc aattagaaca gggctggccg ggacagtga ctcatgtctg  1680
tagtcccagc actttgggtg gccgaggtgg gcagttcact tgaggtcatc agtttgaaac  1740
cagcctggcc aacatggtga aaccccatct ctactaaaag tacaaaaatt agccaggtat  1800
ggtggcgtgc acctgtaata ccagctactc aggagcctga ggcacgagaa ttgcttgaac  1860
ccaggaggca gaggttgcag tgagccatgt tgtaccact gcactccagc ctgggctgga  1920
gactctgcct caaacaaac aaaccaacca accacagggc tttatccagc tctgtagtgg  1980
ggaaagggg cttggaaagg cattatgctt ttgcaccaat aagcctcctc ttatgcaaga  2040
tgcattttta tttagcatat tcatgtttca cgcaatgatc agatctctga aatgtcagtt  2100
tggttctgtt ggaggtgtcc ctactctggt tagaataatc aagctgttca gactcactga  2160
gatcccctc ttttgtgtag tacatcgagt tagatgagaa ccgtctgacc acgaggatc  2220
tggtcaactt gggaaaggga cgctacaaaa taaaggtatg ggagggagg ggaaagatgt  2280
cctctggcca ttttttgttgc ccgtggaagt ctttaacgtg ctcagttctg atcaacatttt  2340
tcctagctca ccccaacagc tgagaagagg gtgcagaaat ccagggaggt catagatagc  2400
atcataaag agaaaacagg tatcttttta tctttatgtt ataaatattt ttataaacaa  2460
acaaaaatcc ctgcatttaa ttgcataatg tctcttttta ttctagttgt ttacggtatt  2520
actacaggtt ttgggaaatt tgccagaact gtaattccta tcaataagct acagtaagtt  2580
taaacacac atatgttcac gttccaccta ccctcatctt ttaaatattt ttcaacaagg  2640
gaaataattc acatttgccc caatttacag atcagaggat gaggcttggg ttaccttgca  2700
tgtgagttgg tattgaaaac ccaggctggc tggtttctcc cattgccttc cttctgtccc  2760
tccaaggatt tgaccatgat tcccttcatt ttcccagctg agggaacatt ttctcactgc  2820
aatgtatcta agagggtttt tacctttctg ttgcaggag cttcaggtca acttagtacg  2880
ctcacattct tcaggtaagt caaaacgttg ggtgcctcct gatccttgtg tgattagatg  2940
aataaagcac agcacagtgt gagttatcca gttatagtca caaaaagcta gtttctcaaa  3000
acagcatttc aagaactagg tgccgaggtg agaaggatg cagaaagaat cagctgagcc  3060
tcagaaaaag aaatgggcca ggtggaggga tggggttggt atgagaacac atgtcccatg  3120
ccatggagac actgttgcat tcagggaagg aaataaagcc tggaactcaa agaatgagtt  3180
aggatgggca tagtgagatg ggaaagactg tcaccaatca gcacccatca gatggtaaag  3240
aagttgtgct aaggactctg gatgctattc taaaggtgag tgggaggtca ggggttcact  3300
gaagcttccc aaaaagggga attgagaagg caaaactggg gtcttaacct tgtcaggaa  3360
gatggggctc agacaagtca gacaggcagg agggagagta gtccaactac ctgagccgag  3420
aggagaaggt aatagcaggc tgggctacat atgggaaaga ttggaggag ggagggcaat  3480
tgtcaggaga caaaaggag tttgcttttc ttggagaaaa catcaattct gttttgcagg  3540
tgttgggaaa ccactaagtc ctgagaggtg tcggatgctc ttggctttaa ggatcaatgt  3600
cttagccaaa ggatacagtg gcatttccct ggagaccctc aaacaagtca tagaaatgtt  3660
taatggtaat gcaatggctc cctagacgga acctctgtgg aggctggaca tgtaccacag  3720
ggtagaattg attggccaga tgctgaggaa tcacctgaga agacatgaaa taattgaaat  3780
gagtgggaaa tgccgttggc aaaaagtagg atagttagat ggggaagag gagaaagtcg  3840
atcagagtg cttactccta tgaactttaa cttattctgc aagaccccttt ccctagcatt  3900
tgtcatcttc aagactagaa caggactctt aagtctgccc ttacattcaa gcctgcctag  3960
aagaaacttg gattaagtgg tacatgaata tggttagaaa aattgcatga tatcaatgtc  4020
catcccaaag gccaattcag tagttctggt tggtgcctgg gaatctgaaa tcgtaatgtc  4080
ccccaggtga tggccagact tgcacactaa aatccaactt cttgcaaggg tagaacagaa  4140
atgcaaagag gttaatgact cccttgtaat caagaagcca tgtagtggca ggatatgagg  4200
gaactcaact ctggagcttt cttcttggat aggaaaattc taatgtggaa accagatttg  4260
cagtgattgg aggtattgtc ccttctcaca ggtaaggaca agcttctag gtcagtggag  4320
actcagaact ctttgagggg aaggagaggg aggaagca gtgctgaggc agtcacaaac  4380
agcaaaacac attcttgagt ttccatgtta tggacgcaag tggcacgtga ataggatctg  4440
ccaatgagtg gagagcaatt tcaatgagca gtctattgta tatacagggc tgtgctgaac  4500
agactagtag tgattccaac acctattttt actcctacct tggtctgcca tactatatag  4560
ccctaaaatc ccagatagta gcactccaac cttaaaccca cctgtacttt atgggggagt  4620
ctaaggcacc tctgagaatt ccccagcgtg aactatcagc cagaagttgg tctgtggatg  4680
gcactgccat acccgactga cattatttaa cagttggaaa aaatgctgct gtcaggaatc  4740
tgattttatt tcagaaaat gaagcctctt ttttggtaac tttttgggaa tttcttagaa  4800
aatggcacgt gttcattgat aaggggcagt ggagtgtaga ctgggtgact ggcaaaatga  4860
aaagactcag ttgcctatga cttctcttcc cctgggaaac cttgttaatg ctttggtgca  4920
ccacctcctt ctggaacatt ttatattact tttccaatgt ttccaaacat tttccaatag  4980
ctgtgaatgg ctaaacttgg tcaaatgaat gtcctttaat ttcatattta gataatttct  5040
aactattttt cctataataa acaatgaact gtaaaacaaa aacaaaaaca aaaaaaaaca  5100
gctagttcct gatcacttct tcaagatata ttgctaaaat ttctacaagt ggaagtacta  5160
ggttgaatta gagcacacag attttgaggg ctttgcatcc agaagtgtcc tccttccttc  5220
ttcttatta tttaggagac aggatcctgc tttgtcaccc aggctggagt gcagtggcac  5280
aatctcggct cactgcaacc tccacctcac gggttcaagt gattctccca tctcagcctt  5340
```

```
cccagtagtt gggactacag gcatgcacca ccatacttgg ctaattttg tatgttttgc    5400
agagacaggg tttcaccgtg ttgcccaggc tggtcttgaa ctcctgggct caagtgatat    5460
gcccgcctcg gcctcccaaa gtgctgggat tacaggcttg agccactgcg cctgcccttt    5520
cttctcttct tgctgacttt ccctccagcc ctcctttcct ccctgtctcc tctttaccttt   5580
tctctcttct tcctctccac ccccactcct cttttctct ctataacaat tcatccaggt    5640
cccttacata ttagctgggt ttgaagaatt gtctttcccc aggtatctat gccataaagt    5700
gatagatatt ggaggcaggg tgtttgcggg ggcagtgggg gcactcactg gcaaagcaag    5760
gagagtcaga atgcagtact cttgaactaa ttgctgccta cttctctccc agcctcctgc    5820
ctgccctatg tcccagagaa aggaaccgtt ggtgccagtg gagaccttgc cccactctgt    5880
catcttgctc ttgggctagt tggagaaggg aagatgtggt ctccgaagag tggctgggct    5940
gatgctaaat acgtaagact cgtagcagct tctatctgca gcaattgccc caggttggac    6000
accaactgtg cttgcatgct tcgtatcacc tagtccttac aacagcccag tgagggagct    6060
cctactatcc ttactttaca gatgagacag cgaaagctta gaagtcagac taggcaagac    6120
tgttgttagc ttctatactc ggctgtcagc cttctgggtt tggtcatcac cttggtgaaa    6180
aggcataact gctactgtta atcccaacta tttatcctgc acctacaaca tttccagtgc    6240
ctagcaggga ggtcacacac tctcacaatt ttaattacga gctggtctca caggtgcagt    6300
ggtatggctc atagcactta ctatatggct tctggaaagc aggtttcatt ttttccctaag   6360
ctcttaccct agtggctaat caaaaaaagcc tgttttgat aaagcttttgg tgttttcttc    6420
atctgtgtct gaatttcatt acagcagcat aaagcatcat ttaatgtatc atccctgatg    6480
aactgctggg agcttccctg atagtaagtg aaagggtag agggcccag aagaggaaac    6540
agctaaggaa atagataatc cttttgggga tgcagcttct agatcatctg tcttccgtgc    6600
aggcttgtct ttgattattt cactatgac agcgttttcc tccgaccacc ctcatacagc    6660
aatcaccctg acctttctaa acagcaaatt caagcatgtt ctggtgaaaa cttgtaatgc    6720
ttcccattgt cctcaggata aaggctaaac ttaaagtggc tttcaagggt cttgtttgtc    6780
acattagccc ctaatccctt ctatgtgtgg ttctgcattg cagaaactgg aggttgcttg    6840
gagaaggaat gttctgggca gagggtctgg tacaaatacg ttcttctctc tcctatttct    6900
gcttctgaaa catcttctag ggatctttttg aagccagaag ttcaagacca gcctgggcaa    6960
gaaagcgagg ctccgcctct acataaaata attaaaaaat tatcctggca cagtagcatg    7020
tgcctgtagt cccagctact caggaggctg aggatcactt gagcccagga gttcaaggct    7080
gcagtgagct aggattgcac cactgtgctc gctctagcct gggttacaga gacaggtgtc    7140
taaaaaataa aaagaaaaat agaaaagccc tctaagaagc ttccgtctcc gctgctccac    7200
ttcctacctc tcgagttcct tgtgacccctc ctgtatgctc tcctagcaaa tgattgttttt   7260
ccactgcacc ccacccactt cccacatcct caagcactga atgtactatt actcagattg    7320
ccctgagctt gcctgtcttc attttgccta ctcctagacc gacccccaaca cccagaacag   7380
aatccagcct ctagctgata cttgaatctg tgaaattgac gtagtaaatg ggaccagctc    7440
tgtcctttctc ttaccttaac ttccccttcc ttctttccta gagagacctt aacttaatga    7500
ctctctactt cttttctttc aagggaagat tgttctgccc atcgcccct cgggattctg    7560
tctccatcta gtagagggaa ttttataatc ccctcttcat tggtgctcac acatgtgcca    7620
caaaaacct gctctgaggt tttgccagta tttaaatgaa gcactaatga ggttagagga    7680
cttttaggt caagctctgg aggcaaggga gcgtgaactg ggaggagtcc agcctgagca    7740
caacacagat gcatgtatgt gtgtcagatg cctgcatgtc aggaggcagt ggtaaaaaag    7800
gtgaactgct aaggtagaaa ctgaacacga aggacgtaga aaccaaaatt tagggttgat    7860
tctatagaca atggagcccc tgatttcagt acaaaaatta attgaaagat aagtctgctt    7920
tcatgactaa agaacagaac tagagaatag accagagaac atgaatacag ccagttcctg    7980
taggtctcat ttcttataag atggactttt gggcataaag agctattatt ggattccata    8040
tgatattgga aataggctag tatttcattt gatacccatt ttcatatttt taatcattct    8100
ataggtgcta gaagcccatg gattgaaacc agttattta aaaccaaaag aggtaaggaa    8160
actcaagaaa aatatgttca tagtgcatga gttttattt atgcagtatt ttcagttta    8220
atctcagcct caatcattcc ttaaatgcaa cttgcatgtt tgcttaaagt tcatccctga    8280
agaagggca actccgtaag aatttaaaag attctttatg ccaggcatgg tggcggatgc    8340
ctgtaatcct agcactttgg gaagccgaga caggtggatt gcctgagctc aggagtttga    8400
gaccagcctg ggcaacatgg tgaaacccat ctctacccgc cccccccgcc ccgcaaaaa    8460
agacaaaaat tagccaggca tggtggcgca cacctgtaat cccagctacc ctggaggcta    8520
aggtgggagg atcacttgag ccctggaggt caaggctgca gggagccatg atcgcaccac    8580
tgcacaccag cctgagcaac acagtaagac cctgtctcaa aaaagaaaaa aagattcttc    8640
atgccacaat gcatagggg tctcttagga acttaaaact tcaaatcgag ttctgttagg    8700
atctctgaga gatagatgtt ctcagcccaa attccttaga atgctctaag ctaagagtct    8760
tggaccagaa ttgggttttt ttggatgtct catctataac agtaagaatt taaggaagaa    8820
atgcaaccta atgcactaaa gatttttatgt gcagtctaca ctccagagct gcattgctgc    8880
tttgggaatg tggatactta atgagtgttt catttgccag attttgtgctt acgagttcac    8940
atatgatagc acttattctt caagggctta aataaacatt actgtcccgc actttagaaa    9000
acataaacat aattttttat gtttatgact ggctaatttt tctcttatga aagcaaaaga    9060
tacaaaatcc acgggtatgt aggttcgtta caataatcac agtaggaaac tttgctctct    9120
cccccgacag ggcctggcac tcatcaatgg gacgcagatg atcacatccc tgggctgtga    9180
agctgtagag cgagccagtg ctattgcacg gcaggctgac attgctggcag ccctgaccct    9240
tgaggtgctg aagggcacca ccaaagcctt tgacactggt cagcagggtt cttccttttg    9300
gttgttattc attcaaccag aggtggtggg gcggggtggc tgagatcttt agacacagaa    9360
gtggtgggg caggtagtag ggaaggagaa acccaagtg cctgtggcgt acccagtgtg    9420
ctgcctcttc atctaggcta tggcacaact gatcttttgaa agaactgcaa tttacagata    9480
cacacagccc ggaagttgag tgacttgcct gagagcaccc agggatctgg gtgtgtcaag    9540
ctctgtgctg tcttaggaat cttttttacag gacttaggag tcctgtaaaa aggagtagga    9600
ttagagttgg tcccgactag aaaattgggg aagaaaaact gtcgaattgg tagcttattt    9660
agaaagtagt gaatttgac gacctccaa ctataatatg aaaagggca gaacattgtc    9720
taaaagtgaa tgagttaaat taggccactg tagggctcc tcctgttatt cgccctgtga    9780
ctttaaggta ggcccagtgt cttgagtgga attccagtg gtctcaacat atagtttgct    9840
ctcagatatt taaagtagaa ggagtcaagt caataaggaa aatcgtgctt tcggagttaa    9900
gtttctaatt ctgagtggtg gctaaggacc cctgggactt tgagggctg tgtcagcacc    9960
gtagatggtc ctgaaccatt gatggtcatt tgttctaata tcagaattac tcgacctggc   10020
atggtggctc atgcctgtaa tcccagcact tgggaggcc aaggtaggag gatcgctaga   10080
```

-continued

```
gcccaggagt tgaaaccag cctggggaac gtagtgagac ccccatcttt aaaaaaaata  10140
aataaatgga attattcaga ctttttctcc ttcatcaatt ctagacattc atgctcttcg  10200
acctcaccgt gggcaaattg aagttgcttt tcggtttcgg tcactcttgg actcagatca  10260
ccacccatca gaaatagcag gtctgaccat gtttatggga gtgacctatt tggttacgtg  10320
ttttgtgaaa agaattggta acatgatccc tgtctcatcc cctccacctc ttccacagag  10380
agtcacaggt tctgtgatcg cgtccaggat gcatacacct tgcgctgctg tccacaggta  10440
aaataaagaa aaaaaaaaag gtcaataaaa aatgccaata aagttttctt ttccccaggt  10500
tcaggatgaa aaattttaaa ataggaaagt gttagaaaaa catgtaatgg tcaactatag  10560
tccaaatttc ttactgtctc tatgaaaagt tatgtatatt ttacctttat gtgtgcaatt  10620
gttgtaaagt ttctattcta tatggtgaac tatttgtttt cttttgattg ttcaacctac  10680
tttcagagga caacctcttt tttttttttt ttttttttt gagacagaca accaacaaat  10740
aacctctttg atttggagac agagtctcac tctgtcaccc tggctggagt acagtggcat  10800
gatctctgtt cactacaatc ttcacctccc aggttcaagt gattctcctg cctcaacctc  10860
ccgagtagat gggattacag gcatgccaa ccatgcctaa tttttgtatt tttagtagag  10920
atggggtctc accatgttgg ccaagctggt ctcgaacccc tgacctcaaa tgatccacct  10980
gcctcagcct cccaaagtgc tgggattaca ggcgtgagga ccgtcccgg cccagacaac  11040
ctcttatgtt gattcagtgc cctaactttt aaaaattctt agtaataaaa tcataaccag  11100
ttagtagagt tgtactgttt ctccctgtta agatgaaact ttaaccagat agtcagaggt  11160
gtttacagga aagtcttaat tatatcattt tgaaactcag gtgcatagta atggttatac  11220
cttacttgca ttttatgggc aatataaatt attttaaatg aatttgtgat gcttaacttt  11280
aaaattaaaaa tgcagatgac ctgggttggc attaggcatc tgtattacag atgtgtaatt  11340
tacatatgac agttagagag ccagtcatct caataaacca tattttggtc tgtgccaaat  11400
ttcagtctat ggtgtaatag agagtcctcc ctagaataaa taccctcatt tccctttagt  11460
cagcaagtta tcttttctag ctagcttatt gagcaataga tcaaaacacc tatgggtaag  11520
aattgccaaa ttagatctac aggaagatta agtcctgatg taagacttcc ctgatatttt  11580
aataacgata gcagattcta tgtgacaggc accattatca ctgtctttca tttattaatt  11640
catttaatct tcccaactat aagatactct ttctcccatt ttgcaatggg gaaactgagg  11700
cacagaatta agtatcttgc ccacgatcac acagacagat aattacttcc ttgacttctg  11760
ggagaaacca gagccaggtg ctgctttata gcattgtggc tatttctggg gtttgtacag  11820
cgtagctgcc ttatgtgtga gcatcttcta atgtgatgcc ttcgtgctta atgaacttta  11880
ccgccttgga taatagctac catttgagta atctctgcga gtcacatcta agaatttgtt  11940
tgcattattt tatgtacttc tcaaaagcca taagtgctat tgtctctttt ctaagtcttc  12000
ctatcttta actataaacc taaggaactt gcccaagtcc taccactaac ctgggagtga  12060
atctgcctgt gtctagagtt ggcattcttc ctcccacacc atgctgcttt gtatagattg  12120
atctaatgtg aatatatatg ataatgaatt tattctaatt tgtttcagtg aaaacccaaa  12180
agaattataa caaaattatc ttcagttcaa ataatttcca tggttataac tttaaaataa  12240
gatcttctgt attctttata actttaagat aagatcttct atattctttt aagaatattg  12300
gtactcttca ggtaatcaaa tgggtcatat accttatttt gattgtattt taggtccatg  12360
gtgtggtgaa tgatacaata gcatttgtga agaacatcat taccacagaa ctgaacagcg  12420
caacagataa tcctgtatct tttgattgta tactaacctg caattataga attgcagctg  12480
gtaattttag gatctactga aacaatcatt ttgtgtagct tctcagttcc attgctccat  12540
ttcacagagt aaatgaatca gtacctgagg ctcagaggtt aactgacttt ctccaggtca  12600
gagctgtaa gtggcagagg tgacctgtga acttactctg aggttccaag tctaacatgc  12660
tgtactttca aaatgaccct attcaagatt taagaagata tttccagcat ggctgacat  12720
gtttcctgaa gacactggcc ctaaaaccca ctgccaaggt tgttggtgga agggtgaaga  12780
cgtgggtcac aaatgtgatt gcagaaatgc tgaacaattt atgcaggcct ctctgctttg  12840
agtgagagca gtttgcatta tgcagaggtc agccttttaa cacttaccaa agtattgatt  12900
aaagagttat ggcttcctca tcctgaggtt tttggcattt tttttttttgt ttatttttag  12960
acggagtctc actctgtctc ctaggctgga gtgcagtggt gccatctcgg ctctctgcaa  13020
cctctgcctc acgggttcaa gcgattctcc tgcctcagcc tcctgagtag ctggaattac  13080
aggcatgtgc cagcaggcct ggctaatatt tgtattttta gtagagacag gttttgctg  13140
tgttggccag gctggtctca aactcctgac ctcaagtgat ccacctgcct cggcctccca  13200
aagtgccggg attacaggtg tgagcgacta cacccagccc ccatcatgag ttttatttg  13260
tcatgcgcac tttgctcaaa ttagtgcttt tgcgtttgtt caaagaaata gtaaaactga  13320
ttccatttct caaggatgga ggtcctctct taatggtgtg gcttatctca gagccatctg  13380
gtttttctct ggaatgttcc atgatgctc agttccccag atgttgaggt gatcagtcag  13440
gagtcacact ggcacagttt tcatggagat agcactgcc ctgaagataa tcaaacgcct  13500
ttggaatcta ttttttcctat tccacatctg cctcagttct gaatcctaga gaaagtgctg  13560
agtaagcagc cccaaaagca ggtcacaggc tgagttagaa gatggttatg tgatagctcc  13620
ataaggtttc ccatgagatg gcttttgtat gtatgtgttt tttgacaagc ttacttcaga  13680
atgtgtgttt tatgttctct cacattgttt tacactgaag tcaaacccac actaaataag  13740
cctcagaaat tgtgggtctc tccattcacc tcaataccac cccatccccc agatggaata  13800
gtagttttta tgaactctat gtagtcttat ctcacgtacc agtctttttca ctgtaggaa  13860
gaggtatcta ttctacattt acatcattgc ttttaaaggg tatctcatag tttttagaaa  13920
ttaccattca attactgaat atggggcagg ggataattaa ttcctcacta aattcttctg  13980
ctaccaattg cctcagcaag aatttcagcc aaaagtcttt tattttttc aattaaagat  14040
tgctaattat tgataaattt ccataggct aatatttggg agttctcttg caatactgct  14100
gttacctgaa agaatatgtg tctcaatttt ctgttgcaga tacggagccc catcacacat  14160
gctggatatt atgggagtta aattctaatt aatagccaac aaacaaattt  14220
ggaacaacta gaggacaata aaaacatgtc taagttctaa attgatgcag aattccattg  14280
ctataggat tcagagaatg gagaagaggc caagaccaag gagctagacc caatgggctc  14340
acagttacac atgcagaaca gagtaatcca cacttgagta ggttaatgta acacatacat  14400
ctctaactct ttcaaagtta gaaactttct tgcacacagc gagtctcag ttaataggta  14460
atgaatattc tgagcccaa gaggcaaaga ttagctcttt agaaccagga agaaggatct  14520
gttactgcct tttcctgggt gcttgctggt ttaagtaaag tgcatgatgg aatagaatta  14580
tctgaggctg ggtttggtgg ctcacacctg taatcccagc actttgggag gccaaggtgg  14640
gctgatcact tgaggccaag agtccaagac cagcctggcc aacatggcaa accctgtct  14700
ctactaaaaa tacaaaattt aactgggtgt gatggtgcat gcctgtaatc ccagctactc  14760
aggaggctga ggcacaagaa atcacttgaa cccgggaggc agaggtcgca gtgagccgag  14820
```

```
atggcgcccc tgcactccag cctgggtgac agaatgatac agaaaataaa aaaagaatta   14880
cctcagagta ataatattca gcaaatttaa acttgccacc tacttaaaat ggattcatga   14940
ggacatattg gccaccatct gctgttgaac gctgacacca gattactgag taaagaattt   15000
gaaaattttc tcaaaattga ttgttccaga cattttggta gttgctcatc agcagagttc   15060
cccattcaac agattcttct atggaacaca aatttgcagt gcccattgaa gaaacagaag   15120
ttgcttttcaa acagatgtgt tggtctctgt ttttagtttc aggctataaa ccttttgagg   15180
gcaggtacta accaccaggt tagtacagtt atggtgcttt agaatctaat ctcaagagaa   15240
aacatcattt caaggttcat gttttttcag cctccaaatt gggtgtacat gatccacctt   15300
taaggctttt tgttttttgc ttttgtgccc ctttatatct cttgcaggaa gacttgtctc   15360
tttccctcca ccccacattt gtacacagac tgccacctcc acgttaaaaa agaaggcagg   15420
aagggggttgt acttgaagtg accagcaaac attatcttca agccttaacc tcttttgaaa   15480
gatggtcttt gccaataggg gagagacagt ttctggagga aacttccatg gtgaataccc   15540
agccaaagta agctttttaa aactgctcct gacccagaag gcacatttca atataggctg   15600
actaaatgga gaccctcttt caggccctag actacttggg cattggcatc catgaacttg   15660
ctgcaatcag tgagagaaga atcgagcggc tctgcaatcc ctccctcagt gagctgcctg   15720
ccttcctggt ggctgaaggt ggtctgaact ctgggttcat gatagctcac tgcacggcag   15780
cagcccttgg taaggacact gccccttctc cagaacacac gcccgtccat ctaagggtct   15840
ttccatttca cctagaagta tcaaatgtgg tctgtgagtg agatctaact tttcaccact   15900
tttatctgca tcctagttct ctcagtgcaa aggtaacagg ttaactctaa tattttttcag   15960
aaaaaaaatag tttaaaaact tcgatactgt tatgctgaaa tataataata caataataag   16020
gctgtaatgg acaatttctc tgtggaaagc aatttgacat tgcatatgaa cttcatctct   16080
atagctttt tccaaatctc catttgaaga ctattggaaa aagactaagta tggttatagt   16140
taatggtgaa acttgaacca acctataatt aaactttgaa cttttaaacc tataattaaa   16200
ctttggattc atttcactag atataacaac cactaaaaac ataaagatgt tattgcaaca   16260
ttaaaaaaat gctataaga atcaggatac cctctgtgaa gattgagctt caatatagtt   16320
tatttctgac tcaagattgt aagagacaga taaacacatc agaacagtgc ctgacactaa   16380
gtaagtacta agggcctcat ttatgttcat tcacttaatt gcacaattgt cacctgaggt   16440
aagtgctatt attgttatct atagatgaat atctgaagat ctgagagtta agtgacttgc   16500
ccaatattgc acagctagca agatgtaaag cagaattcaa accctgaatt ttggcatgca   16560
aaaatgtgct tttacttcaa ttaatgagga tctcatttta atcaatactt aatcctaaaa   16620
tagggttgtc aaatttaaca aaaacacagg atgactagtt aaatttgaat tatttgggac   16680
atacttgtac tacaaaaatt atttttttaa tctaaaatca aaatttaact gggcatcctt   16740
tactttatct aacaaaccta ccctaaaagg caggatagca tgagttatta catgcgtaga   16800
tgctagatca gaagcccagc tctgccattt actagcctctg tgagcctctt tatcctgttg   16860
atcctcaatt tacacctgca taaaatggag atcagtttac ctaagggggt tgtttggagg   16920
attaaatgaa ttgatgtata taaagcctgg cacatcataa gcactaaaaa atactagtt   16980
gctattaata ttattcccaa cgaacacaaa taaccaacta agagccactg aattcacctc   17040
ctctgaccgg tatcttctat ttgcttactt gcttattaat aaaataccc tttaacaggt   17100
agaaatttct cacaataacg tagtagtggg ggagtagtca ttgatttcta gagaacagga   17160
tggacattgg gaagcctcat ttgaatatgt tttagtttcc caagctgcct attgaggttg   17220
tttggcttgc tttcattgta gtaaaattag tgttttttctt ttttttggccc ttgtaagtta   17280
tctttccgaa caagccttac cacagtttac ttatctgtat agtccacagt ttagggtcca   17340
aggacttggg acttacagtg ctgaaacctg gaaagtcctt ggccaaccaa catgaccttg   17400
acaaagtagc atgacccctag tttaaagcga gatcatctta ggatgcgatc ccatgcagca   17460
tagaaaacaa ctgaagcctc acccatgacc actcttaaag ccagaaaag aggagaagag   17520
actttgagtc tgaccttttcc tgacttctaa gctagggtga gggaacttca taacctaagt   17580
ttttgctact tatagtgtag tcctcagacc aacaatatgg cattcacctg agagctcgtt   17640
agaacagcag aatttcacgc cccacccaaa gctcagtata tttgttataa caaggtccct   17700
gagtgattca tgtgcactgg aaagcttgag agtcccatgt cttggtcctc cctagaattc   17760
ccccacctcc cagatatttc tggcagtcat cgagcccctg tttacatcca tttatgtcat   17820
ccttgaacac tctgaagtgt taaatcttct tgcccaagat ttatgggtcc agcctcagtc   17880
cccaaatgcc acatcggaat tctggtgaca caaccaaatt gacgtcaagt acctgaaaat   17940
ggccatcatg tctcttttctc ccctagtctc cctggcatgc tatatgcttc ccaggttgtc   18000
atcttggcct tgttatatta gaattcccag ttctcccatc tccgtcttac ctcagaactc   18060
actattgctt tagagtcctc acttgggaaa aaaaaatgac ctgcttcctt ttcccaaagc   18120
agctttctac catcaggtgc ttggataatg tccaagatct tctggagagt gtatcccatg   18180
ctgtggagca ctctgtggaa gccacgggtc ctttagacag ctcatcctgt gaggagcact   18240
tcttaactgg cactggtctc ttgcagtttc tgagaacaag gctctgtgcc atccctcgtc   18300
tgttgactcc ctctccacca gcgcagccac ggaggaccac gtctccatgg gaggatgggc   18360
agcaaggaaa gccctcaggg tcatcgagca tgtggagcaa ggtaatgctg atgagttcgg   18420
ggtggcgggc ctgcctgata gaccactgtg cccgtggttc tcaagtggga tctcccacca   18480
gcaacatcag catcacctgg aaacttgtta ggaaggcaga ctctcaggcc tccttgcagg   18540
ctggctaatt cagacactcc aggaggagag cggagcaatc tgtgtttaac gaaccctcca   18600
ggtgattctg atcttcacta aagattaaga accaaggaac catgcagaac taagctggtc   18660
ctttggctgg ctttttttttt ctcttttttt ttttttttttt ttgaggcagg atctctatct   18720
gccacccagg ctggagtgca gtgttgcaac aatagctcac tgcagcctg aactcccagg   18780
ctcaagtgat cctccttcct tagtctccta agtaactgac acctcaggca agcaccacca   18840
cacctgggta attttttaaat ttttgtaaa gatggggtct tgctgtgttg ccttggctgg   18900
tcaaactc ttggcctcaa gcgatcctcc cacctcaccc ccaaagtgtt ttttttttta   18960
atgagacttt taaacatat tcaaagtgga gagaagagta ccatgaactc tcacaccca   19020
ccttgattca acagcacatt caattttatga agtacactat gaactctagt gagtgcagac   19080
aggtcacagt gggagaggat gaagttgtgg aattcacggt ggacctggaa gcaatttctc   19140
atcttctagt ccagtatccc caccccgcaa ttcatatgga attggaaacc acgagatgta   19200
aagcatcttg atgaaatgca tacaattatt taatagaacc gggctcaag atgaggatca   19260
gctcttcttt ctgacttcct tccctaccca catgacccaa acttggccaa caaacctttg   19320
ttagaggatg tgaatggggg acatggcaga ttttgctagt gcagatgaat gggcagcttc   19380
ctgggtaggt gtgcaggtct ggtaattatt caggtaaatg tctcaattct cccccttctca   19440
gcattaaaga tatagtcaag gggttagaaa acaggttaaa atggcaacta aataccaaag   19500
caacttcatt ctaccaatag acagagaaca aaccatctgt tagttgggtg gtgatgggtg   19560
```

```
tcaactttgg gaaatccaca ttccttaagc atgaagtcag actttcataa gctaccctct    19620
tggaatttct tgtttcagtg ctggccatcg agctccttgc agcctgccag ggcatagagt    19680
ttctacgtcc cctgaaaaca accactccgc tggagaaggt ctatgacctg gtgcgctctg    19740
ttgtaaggta agatcaaaca ggtctctgaa aattacatca gttcagcact gtgaaccctg    19800
gcagggtttc atgtttggct gatgggcgga tgtgctctcc ctgtaggccg tggataaaag    19860
atcgcttcat ggccccggac atcgaggcag cccacaggct gctcctggag cagaaggcaa    19920
gctggctcct tggcttgttt cttaattttt aattgttaca ggaaagcaaa gtcggggatg    19980
gagaaacatt gccttattct attgttttct ggccattcct tgggaatgag caaaaaggta    20040
tttgagcaac aacttgcagc accactaaga agccatataa taaacactaa gtgcaccagg    20100
gtgcagccaa cggttgaata tctaaggatt agaaacagaa atggatttta aatggagttt    20160
tgggacaata ttcatgggga aaaaaataag atgtcaggtt cattgatgcc tcccccaccc    20220
tgcaagatgc cctctttgat tcaaaagtgc gttcccttct gggtgatgct atcacaacta    20280
ccaccactgg gtgcaatggc tgcgtagacc tggagagaaa accaaggccc gggtgtttac    20340
ttcagaagac tttcggtctg tctagtgctc tggtgagatg cgggttttc tttcttgcat    20400
atttccactg gttacattga ccgtatactc agctgccagg tacagatgcc cagcatgctg    20460
gcttatcttt taaatatcgt ttttgaagtg ctttaaacct tttgaataac ttgtgggtgt    20520
tatgttccct agaatcgctt gatttcctta aaacagttgc tctgctctgg ggcagtgatt    20580
tttccctgtg attttcacac ccattatttc taagcatgcc ctgcactctg gatggggaag    20640
ctgcttgcct gctgccaact ttggctag gagggaggta tacgagaggt tagcctttaa    20700
gagtattcat ttgctaaggt cataaaaaat aataggaaag gctccttggc tgtcagtggc    20760
aatcagttaa aaagcagata taaaccaaaa acagggcctt aatttcattc aatttaaaaa    20820
aaaattttt tagagatgcg ggtcttgcta tgttgccaag gctggactca aactcctggg    20880
ctcaagtgat cctcccactt ggcttcttg agtagctggg actacaggca catgccacca    20940
tgcccgtcca gggccttact ttgagatgat gttatgctta agaaaaaaaa aaaaaagaa    21000
aaaagaggtt ggtgggtggg aggcaaaagc taaccaagga tctgaggcag tgcctctcca    21060
acattaaagt tgctatgaat ctgctgggca tcttgttaaa atgcaggtgt ggattcagta    21120
ggtctgggtg aaggccaaga ttctgacttg tcccaggtga tgctgatact gcaggggcac    21180
aggccacgct ttgagtagca gggtcaaagg aacagagcac ctgtggcatg gaaataaggc    21240
aataggggaa tacaattcac tgccttttac catttaaggc ttgctttaga aaacacacag    21300
gtccagccca tgtgtggtgg ctcacgcctg taatcccagc actttgggaa gctgtggtgg    21360
gtggatcact tgaggccaga aattcgagac cagcctggcc aacatggtga accccatct    21420
ctgctaaaaa tacaaaaatt agctgggcct ggtggcatgc acctgtaatc ccagctactc    21480
aggaggctga ggcacaagaa ttgcttgaac ctggaaggtg gaggttgcag tgagctgaga    21540
tcatgctact gcactccagc ctgggcgaca gagtgagact ctgtctcaca aaaaaagaaa    21600
aaaaacaaaa aaacaagaaa aaaaccacat aggtactgtt aagaccctgg agcaactatc    21660
cttcactcta tccacactga attctctggg ttttgttatt tgcttgcttg ttttgcttag    21720
gaaaagtatg cagcttaaaa tctttatgat gactttagaa agttttggac tttgtatatt    21780
tacagtcttt aatgcaacca aagactaatt gacacaggtc atgtgtcaaa tggcttaaaa    21840
taaaagcaag caaacagcag ctgtgtctgg tcatgtatag agtatgtttt gacttcggat    21900
gaagttgatg tttaatagca tgtggaaaca atgtcgtcaa tatttcaact ttgttttgtc    21960
cttgcttttc aggtttggga agtagctgct ccatacattg aaaaatacag aatggagcat    22020
attccagaat caagacctct ttctccaaca gccttttcac tgcaatttct gcacaagaaa    22080
tccaccaaaa tcccggagtc tgaggacctt taatgggctt tgtcatgaag tagcagatga    22140
gagggcagtc agtttagcac aaagcaatac taggctgaag gagagacctg agaactttcc    22200
taggtagatc aatccattgt atcattcagt tcttctaaag cctacgttgg ttaggctgat    22260
ggcagtatta tagttgctaa attcagcact gtgttcctgt tgtcgtggtt caagacccac    22320
caggtatttt cagattataa aacttttctt tcttcttcaa cagtttcaac aggccactca    22380
ctcttaaggg tgagaagaat aaccacaatt gtatgtgcct gttttttact cttagcatta    22440
gatgaattca aatttggaaa cagattgata gcaattttt ctaaaaacat tagacttttg    22500
ttaacctttt tttttttt taaatttgct tcaacaagct ctccaccagt tgactttctt    22560
tggctaattt tactttgcat gatatgcctt aatatgcctt cataaataac cattttaagt    22620
cataatttgt ccttaagctg ctttttttctt ctattaattg gatcatagta aagagtagtc    22680
aataggggtct tcagctatta attgtagagg tgattaaaac caacaaggag tttcatgtgc    22740
aaaggagata aggaatgaat ataaagattg ctatttgggt ggctcttatt aaactgtgta    22800
ttttgtactt atcactacac gtatccccca aatgcttaca tgggagtttg aggttagtat    22860
tttcacttcc ttggtgttag tactctattc acattcttat tgtaaccttc ctcatttcac    22920
agataaggaa tctttgggga ttaaccaacc tcctttctgt aatggtaatc attaaaataa    22980
gtcctattga taaaggtcag atggagccct agagtgtatt actgcatcta tttttttccc    23040
cgagaagata aaggaccttc agggatggct taagtgtatc tgtccagatg aaggatggt    23100
cacatgacct cttggcttcc caagtctaag ctctgtgact ttgcaccagt gtgtgcatat    23160
atgtgcaagg cccttcaagt ggtctgaaac cgtggctcta aaaaccacag ctggtggaga    23220
ggaggacaga cacacttgcc accttgccta cctaattgcc atctaaaatg ggccgaacag    23280
tggatttcac aatagagttt tcacccttta gatttacaac ctgtcaggtg gaaactgaag    23340
tgaaaactgc tgcacacagc aattcaggga gcaaaaaatg tgctgaggag actgtttacc    23400
taaaggttgt tcttggtgct attccttgtc aaaatgtgaa cacacacaaa tgaggtttgt    23460
gcattgtcat ccgtgggctg ccattgagcc agtaacccc agtggtctca tggtgctctt    23520
cgctccagtt tggggaatgc tggattcttt cagcccctgc agccctccag gtcaaaatga    23580
cactttgtca ctgagttttc tacacagctc tattagtaac tgacagcaca cgccttcaag    23640
ggaacttcaa gggaaacatg gaataaacta agtctcaatt gcc                     23683
```

SEQ ID NO: 4        moltype = RNA   length = 3892
FEATURE             Location/Qualifiers
source              1..3892
                      mol_type = genomic RNA
                      organism = Homo sapiens
SEQUENCE: 4

```
agataaagac aggaacatgg tgtttataag ctgcccttaa tggcagagaa cacagacaga    60
aacgagggaa gagagagaaa ttggggaccc tgaagaaagg gggccagcag caggtaggtg    120
ccatcaggga caagaacagc acctcccagg gtgggagacc ccaggccttt ctggcagcag    180
```

```
gtctggatgg aaagtggaca ggaggctcac ccgtctgcat cccctgctcc tgccctgct    240
cggctacaaa aaccaaaggg acagcagctg accacacccc ggtagccact cctgcataaa   300
gctctcccct cctgtgacca gctgaggacc tcaggctgca gcggagccat gcccagatac   360
acggtgcacg tacgtgggga atggctggca gtgccctgcc aggacgcgca gctcactgtg   420
ggctggctgg gccgggaggc cgtgaggcgc tatatcaaga ataagcccga caatggtggc   480
ttcacctccg tggatgacgc gcacttcctt gtgcgccggt gcaagggcct gggcctgctg   540
gacaacgagg accggctcga ggtgccccta gagaacaacg agttcgtgga agtggttata   600
gagggtgatg ccatgtctcc tgacttcatt ccatctcaac cagaaggagt ttatctatac   660
agcaagtacc gggagcctga aaagtacatc gagttagatg gagacgtct gaccacggag   720
gatctggtca acttgggaaa gggacgctac aaaataaagc tcacccccaac agctgagaag  780
agggtgcaga aatccaggga ggtcatagat agcatcataa aagagaaaac agttgtttac   840
ggtattacta caggttttgg gaaatttgcc agaactgtaa ttcctatcaa taagctacag   900
gagcttcagg tcaacttagt acgctcacat tcttcaggtg ttgggaaaacc actaagtcct   960
gagaggtgtc ggatgctctt ggctttaagg atcaatgtct tagccaaagg atacagtgct   1020
atttccctgg agaccctcaa acaagtcata gaaatgttta atgcctcctg cctgccctat   1080
gtcccagaga aaggaaccgt tggtgccagt ggagaccttg ccccactctc tcatcttgct   1140
cttgggctag ttggagaagg gaagatgtgg tctccgaaga gtggctgggc tgatgctaaa   1200
tacgtgctag aagcccatgg attgaaacca gttattttaa aaccaaaaga gggcctggca   1260
ctcatcaatg ggacgcagat gatcacatcc ctgggctgtg aagctgtaga gcgagccagt   1320
gctattgcac ggcaggctga cattgtggca gccctgaccc ttgaggtgct gaagggcacc   1380
accaaagcct ttgacactga cattcatgct cttcgacctc accgtgggca aattgaagtt   1440
gcttttcggt ttcggtcact cttggactca gatcaccacc catcagaaat agcagagagt   1500
cacaggttct gtgatcgcgt ccaggatgca tacaccttgc gctgctgtcc acaggtccat   1560
ggtgtggtga atgatacaat agcatttgtg aagaacatca ttaccacaga actgaacagc   1620
gcaacagata atcctatggt ctttgccaat aggggagaga cagtttctgg aggaaacttc   1680
catggtgaat acccagccaa agccctagac tacttgtcca ttggcatcca tgaacttgct   1740
gcaatcagtg agagaagaat cgagcggctc tgcaatcccct ccctcagtga gctgcctgcc   1800
ttcctggtgg ctgaaggtgg tctgaactct gggttcatga tagctcactg cacggcagca   1860
gcccttgttt ctgagaacaa ggctctgtgc catcccctcgt ctgttgactc cctctccacc   1920
agcgcagcca cggaggacca cgtctccatg ggaggatgga gcaaggaa agccctcagg   1980
gtcatcgagc atgtggagca agtgctggcc atcgagctcc ttgcagcctg ccagggcata   2040
gagtttctac gtccctgaa aacaaccact ccgctggaga aggtctatga cctggtgcgc   2100
tctgttgtaa ggccctggat aaaagatcgc ttcatggccc cggacatcga ggcagcccac   2160
aggctgctcc tggagcagaa ggtttgggaa gtagctgctc catacattga aaaatacaga   2220
atggagcata ttccagaatc aagacctctt tctccaacag cctttttcact gcaatttctg   2280
cacaagaaat ccaccaaaat cccggagtct gaggacctttt aatgggcttt gtcatgaagt   2340
agcagatgag agggcagtca gtttagcaca aagcaatact aggctgaagg agagacctga   2400
gaactttcct aggtagatca atccattgta tcattcagtt cttctaaagc ctacgttggt   2460
taggctgatg gcagtattat agttgctaaa ttcagcactg tgttcctgtt gtcgtcgttc   2520
aagacccacc aggtatttc agattataaa acttttcttt ctttcttaac agtttcaaca   2580
ggccactcac tcttaagggt gagaagaata accacaattg tatgtgcctg ttttttactc   2640
ttagcattag atgaattcaa atttggaaac agattgtgatg caattttttc taaaaacatt   2700
agactttttgt taaccttttt tttttttttt aaatttgctt caacaagctc tccaccagtt   2760
gactttcttt ggctaatttt actttgcatg atatgcctta atatgccttc ataaataacc   2820
attttaagtc ataatttgtc cttaagctgc tttttttcttc tattaattgg atcatagtaa   2880
agagtagtca atagggtctt cagctattaa ttgtagaggt gattaaaacc aacaaggagt   2940
ttcatgtgca aaggagataa ggaatgaata taaagattgc tatttgggtg gctcttatta   3000
aactgtgtat tttgtactta tcactacacg tatcccccaa atgcttacat gggagtttga   3060
ggttagtatt ttcacttcct tggtgttagt actctattca cattcttatt gtaaccttcc   3120
tcatttcaca gataaggaat cttttgggat taaccaacct cctttctgta atggtaatca   3180
ttaaaataag tcctattgat aaaggtcaga tggagcccta gagtgtatta ctgcatctat   3240
ttttttcccc gagaagataa aggaccttca gggatggctt aagtgtatct gtccagatga   3300
aggatgggtc acatgacctc ttggcttccc aagtctaagc tctgtgactt tgcaccagtg   3360
tgtgcatata tgtgcaaggc ccttcaagtg gtctgaaacc gtggctctaa aaaccacagc   3420
tggtggagag gaggacagac acacttgcca ccttgcctac ctaattgcca tctaaaatgg   3480
gccgaacagt ggatttcaca atagagtttt cacccttag attacaacc tgtcaggtgg    3540
aaactgaagt gaaaactgct gcacacagca attcagggag caaaaatgt gctgaggaga   3600
ctgtttacct aaaggttgtt cttggtgcta ttccttgtca aaatgtgaac acacacaaat   3660
gaggttttgtg cattgtcatc cgtgggctgc cattgagcca gtaaccccca gtggtctcat   3720
ggtgctcttc gctccagttt ggggaatgct ggattctttc agccctgca ccctccagg    3780
tcaaaatgac actttgtcac tgagtttct acacagctct attagtaact gacagcacac   3840
gccttcaagg gaacttcaag ggaaacatgg aataaactaa gtctcaattg cc           3892
```

```
SEQ ID NO: 5              moltype = RNA    length = 3846
FEATURE                   Location/Qualifiers
source                    1..3846
                          mol_type = genomic RNA
                          organism = Homo sapiens
SEQUENCE: 5
gttttacagt tgagtaatct cagataaaga caggaacatg gtgtttataa gctgccctta    60
atggcagaga acacagacag aaacgaggga agagagagaa attggggacc ctgaagaaag   120
ggggccagca gcaggtaggt gccatcaggg acaagaacag cacctcccag ggtgggagac   180
cccaggcctt tctggcagca ggtctggatg aaagtggaca aggaggctca cccgtctgca   240
tcccctgctc tcggctacaa aaaccaaagg acagcagct gaccacaccc ggtagccac    300
cctgcataaa gctctcccc cctgtgacc agctgaggac ctcaggctgc agcggagcca   360
tgcccagata cacggtgcac gtacgtgggg aatggctggc agtgccctgc caggacgcgc   420
agctcactgt gggctggctg gccggggagg ccgtgaggcg ctatatcaag             480
aataagcccg acaatggtgg cttcacctcc gtggatgacg cgcacttcct tgtgcgccgg   540
tgcaagggcc tgggcctgct ggacaacgag gaccggctcg aggtggcccct agagaacaac  600
```

```
gagttcgtgg aagtggttat agagggtgat gccatgtctc ctgacttcat tccatctcaa    660
ccagaaggag tttatctata cagcaagtac cgggagcctg aaaagtacat cgagttagat    720
ggagaccgtc tgaccacgga ggatctggtc aacttgggaa agggacgcta caaaataaag    780
ctcacccccaa cagctgagaa gagggtgcag aaatccaggg aggtcataga tagcatcata   840
aaagagaaaa cagggagctt caggtcaact tagtacgacc acattcttca ggtgttggga    900
aaccactaag tcctgagagg tgtcggatgc tcttggcttt aaggatcaat gtcttagcca    960
aaggatacag tggcatttcc ctggagaccc tcaaacaagt catagaaatg tttaatgcct   1020
cctgcctgcc ctatgtccca gagaaaggaa ccgttggtgc cagtggagac cttgccccac   1080
tctctcatct tgctcttggg ctagttggag aagggaagat gtggtctccg aagagtgcat   1140
gggctgatgc taaatacgtg ctagaagccc atggattgaa accagttatt ttaaaaccaa   1200
aagagggcct ggcactcatc aatgggacgc agatgatcac atccctgggc tgtgaagctg   1260
tagagcgagc cagtgctatt gcacggcagg ctgacattgt ggcagcctg accttgagg     1320
tgctgaaggg caccaccaaa gcctttgaca ctgcattca tgctcttcga cctccaccgtg   1380
ggcaaattga agttgctttt cggttcggt cactcttgga ctcagatcac cacccatcag   1440
aaatagcaga gagtcacagg ttctgtgatc gcgtccagga tgcatacacc ttgcgctgct   1500
gtccacaggt ccatggtgtg gtgaatgata caatagcatt tgtgaagaac atcattacca   1560
cagaactgaa cagcgcaaca gataatccta tggtctttgc caatagggga gagacagttt   1620
ctggaggaaa cttccatggt gaatacccag ccaaagcct agactacttg gccattgcca    1680
tccatgaact tgctgcaatc agtgagagaa gaatcgagcg gctctgcaat ccctccctca   1740
gtgagctgcc tgccttcctg gtggctgaag gtggtctgaa ctctgggttc atgatagctc   1800
actgcacggc agcagccctt gtttctgaga caaggctct gtgccatccc tcgtctgttg    1860
actccctctc caccagcgca gccacgagg accacgtcc catgggagga tgggcagcaa    1920
ggaaagccct cagggtcatc gagcatgtgg agcaagtgct ggccatcgag ctccttgcag   1980
cctgccaggg catagagttt ctacgtcccc tgaaaacaac cactccgctg gagaaggtct   2040
atgacctggt gcgctctgtt gtaaggccct ggataaaaga tcgcttcatg gccccggaca   2100
tcgaaggcagc ccacaggctg ctcctggagc agaaggtttg ggaagtagct gctccataca  2160
ttgaaaaata cagaatggag catattccag aatcaagacc tctttctcca acagcctttt   2220
cactgcaatt tctgcacaag aaatccacca aaatcccgga gtctgaggac ctttaatggg   2280
ctttgtcatg aagtagcaga tgagagggca gtcagtttag cacaaagcaa tactaggctg   2340
aaggagagac ctgagaactt tcctaggtag atcaatccat tgtatcattc agttcttcta   2400
aagcctacgt tggttaggct gatggcagta ttatagttgc taaattcagc actgtgttcc   2460
tgttgtcgtg gttcaagacc caccaggtat tttcagatta taaaacttt ctttctttct    2520
taacagtttc aacaggccac tcactcttaa gggtgagaag aataaccaca attgtatgtg   2580
cctgttttttt actcttagca ttagatgaat tcaaatttgg aaacagattg atagcaattt   2640
tttctaaaaa cattagactt ttgttaacct ttttttttt ttttaaattt gcttcaacaa    2700
gctctccacc agttgacttt ctttggctaa ttttactttg catgatatgc cttaatatgc   2760
cttcataaat aaccatttta agtcataatt tgtccttaag ctgcttttt cttctattaa    2820
ttggatcata gtaaagagta gtcaatrggg tcttcagcta ttaattgtag aggtgattaa   2880
aaccaacaag gagtttcatg tgcaaaggag ataaggaatg aatataaaga ttgctatttg   2940
ggtggctctt attaaactgt gtatttgta cttatcacta cacgtatccc ccaaatgctt    3000
acatgggagt ttgaggttag tatttcact tccttggtgt tagtactcta ttcacattct    3060
tattgtaacc ttcctcattt cacagataag gaatctttgg ggattaacca acctcctttc   3120
tgtaatggta atcattaaaa taagtcctat tgataaaggt cagatggagc cctagagtgt   3180
attactgcat ctatttttt ccccgagaag ataaaggacc ttcagggatg gcttaagtgt    3240
atctgtccag atgaaggatg ggtcacatga cctcttggct tcccaagtct aagctctgtg   3300
actttgcacc agtgtgtgca tatatgtgca aggcccttca agtggtctga aaccgtggct   3360
ctaaaaacca cagctggtgg agaggaggac agacacactt gccacccttgc ctacctaatt   3420
gccatctaaa atgggccgaa cagtggattt cacaatagag ttttcacccct ttagatttac   3480
aacctgtcag gtgaaactg aagtgaaaac tgctgcacac agcaattcag ggagcaaaaa   3540
atgtgctgag gagactgttt acctaaaggt tgttcttggt gctattcctt gtcaaaatgt   3600
gaacacacac aaatgaggtt tgtgcattgt catccgtgcg ctgccattga gccagtaaca   3660
cccagtggtc tcatggtgct cttcgctcca gtttggggaa tgctggattc tttcagcccc   3720
tgcagccctc caggtcaaaa tgacactttg tcactgagtt ttctacacag ctctattagt   3780
aactgacagc acacgccttc aagggaactt caagggaaac atggaataaa ctaagtctca   3840
attgcc                                                              3846

SEQ ID NO: 6           moltype = RNA  length = 2637
FEATURE                Location/Qualifiers
source                 1..2637
                       mol_type = genomic RNA
                       organism = Homo sapiens
SEQUENCE: 6
agataaagac aggaacatgg tgtttataag ctgcccttaa tggcagagaa cacagacaga     60
aacgagggaa gagagagaaa ttgggaccc tgaagaaagg gggccagcag caggtaggtg    120
ccatcaggga caagaacagc acctcccagg gtgggagacc ccaggccttt ctggcagcag   180
gtctggatga aaagtggaca ggaggctcac ccgtctgcat ccctgctcc tgcccctgct    240
cggctacaaa aaccaagggg acagcagctg accacacccc ggtagccact cctgcataaa   300
gctctcccct cctgtgacca gctgaggacc tcaggctgca gcggagccat gcccagatac   360
acggtgcaca tacgtgggga atggctggca gtgccctgcc aggacgcgca gctcactgtg   420
ggctggctgg gccgggaggc cgtgaggcgc tatatcaaga ataagcccga caatggtggc   480
ttcacctccg tggatgacgc gcacttcctt gtgcgccggt gcaagggcct gggcctgctg   540
gacaacgagg accggctcga ggtggcccta gagaacaacg agttcgtgga agtggttata   600
gagggtgatg ccatgtctcc tgacttcatt ccatctcaac cagaaggagt ttatctatac   660
agcaagtacc gggagcctga aaagtacatc gagttagatg gagaccgtct gaccacggag   720
gatctggtca acttgggaaa gggacgctac aaaataaagc tcacccccaa cagctgagaag  780
agggtgcaga aatccaggga ggtcatagat agcatcataa aagagaaaac agttgtttac   840
ggtattacta caggttttgg gaaatttgcc agaactgaaa ttcctatcaa taagctcag    900
gagcttcagg tcaacttagt acgctcacat tcttcaggtt tgggaaacc actaagtcct    960
gagaggtgtc ggatgctctt ggctttaagg atcaatgtct tagccaaagg atacagtggc   1020
```

```
atttccctgg agaccctcaa acaagtcata gaaatgttta atgcctcctg cctgccctat   1080
gtcccagaga aaggaaccgt tggtgccagt ggagaccttg ccccactctc tcatcttgct   1140
cttgggctag ttggagaagg gaagatgtgg tctccgaaga gtggctgggc tgatgctaaa   1200
tacgtgctag aagcccatgg attgaaacca gttattttaa aaccaaaaga gggcctggca   1260
ctcatcaatg ggacgcagat gatcacatcc ctgggctgtg aagctgtaga gcgagccagt   1320
gctattgcac ggcaggctga cattgtggca gccctgaccc ttgaggtgct gaagggcacc   1380
accaaagcct ttgacactga cattcatgct cttcgacctc accgtgggca aattgaagtt   1440
gcttttcggt ttcggtcact cttggactca gatcaccacc catcagaaat agcagagagt   1500
cacaggttct gtgatcgcgt ccaggatgca tacaccttgc gctgctgtcc acaggtccat   1560
ggtgtggtga atgatacaat agcatttgtg aagaacatca ttaccacaga actgaacagc   1620
gcaacagata atcctatggt ctttgccaat aggggagaga cagttctggg aggaaacttc   1680
catggtgaat acccagccaa agccctagac tacttggcca ttggcatcca tgaacttgct   1740
gcaatcagtg agagaagaat cgagcggctc tgcaatccct ccctcagtga gctgcctgcc   1800
ttcctggtgg ctgaaggtgg tctgaactct gggttcatga tagctcactg cacggcagca   1860
gcccttgttt ctgagaacaa ggctctgtgc catccctcgt ctgttgactc cctctccacc   1920
agcgcagcca cggaggacca cgtctccatg ggaggatggg cagcaaggaa agccctcagg   1980
gtcatcgagc atgtggagca agtgctggcc atcgagctcc ttgcagcctg ccagggcata   2040
gagtttctac gtccctgaa aacaaccact ccgctggaga aggtctatga cctggtgcgc   2100
tctgttgtaa ggtttgggaa gtagctgctc catacattga aaaatacaga atggagcata   2160
ttccagaatc aagaccttct tctccaacag cctttttcact gcaatttctg cacaagaaat   2220
ccaccaaaat cccggagtct gaggaccttt aatgggcttt gtcatgaagt agcagatgag   2280
agggcagtca gtttagcaca aagcaatact aggctgaagg agaacctga gaactttcct   2340
aggtagatca atccattgta tcattcagtt cttctaaagc ctacgttggt taggctgatg   2400
gcagtattat agttgctaaa ttcagcactg tgttcctgtt gtcgtggttc aagacccacc   2460
aggtattttc agattataaa acttttcttt ctttcttaac agtttcaaca ggccactcac   2520
tcttaagggt gagaagaata accacaattg tatgtgcctg tttttactc ttagcattag   2580
atgaattcaa atttggaaac agattgatag caatttttc taaaaacatt agactttt    2637
SEQ ID NO: 7             moltype = RNA   length = 3822
FEATURE                  Location/Qualifiers
source                   1..3822
                         mol_type = genomic RNA
                         organism = Homo sapiens
SEQUENCE: 7
agataaagac aggaacatgg tgtttataag ctgcccttaa tggcagagaa cacagacaga   60
aacgagggaa gagagagaaa ttggggaccc tgaagaaagg gggccagcag caggtaggtg   120
ccatcaggga caagaacagc acctcccagg gtgggagacc ccaggccttt ctggcagcag   180
gtctggatgg aaagtggaca ggaggctcac ccgtctgcat cccctgctcc tgcccctgct   240
cggctacaaa aaccaaaggg acagcagctg accacacccc ggtagccact cctgcataaa   300
gctctcccct cctgtgacca gctgaggacc tcaggctgca gcgagccat gcccagatac   360
acggtgcacg tacgtgggga atgctggca gtgcctgcc aggacgcgca gctcactgtg   420
ggctggctgg gccgggaggc cgtgaggcgc tatatcaaga ataagcccga caatggtggc   480
ttcacctccg tggatgacgc gcacttcctt gtgcgccggt gcaagggcct gggcctgctc   540
gacaacgagg accggctcga ggtgcccta gagaacaacg agttcgtgga agtggttata   600
gagggtgatg ccatgtctcc tgacttcatt ccatctcaac cagaaggagt ttatcttatac   660
agcaagtacc gggagcctga aaagtacatc gagttagatg agaccgtct gaccacggag   720
gatctggtca acttgggaaa gggacgctac aaaaataagc tcaccccaac agctgagaag   780
agggtgcaga aatccaggga ggtcatagat agcatcataa aagagaaaac agttgtttac   840
ggtattacta caggttttgg gaaatttgcc agaactgtaa ttcctatcaa taagctacag   900
gagcttcagg tcaacttagt acgctcacat tcttcaggtg ttgggaaacc actaagtcct   960
gagaggtgtc ggatgctctt ggctttaagg atcaatgtct tagccaaagg atacagttgg   1020
atttccctgg agaccctcaa acaagtcata gaaatgttta atgcctcctg cctgccctat   1080
gtcccagaga aaggaaccgt tggtgccagt ggagaccttg ccccactctc tcatcttgct   1140
cttgggctag ttggagaagg gaagatgtgg tctccgaaga gtggctgggc tgatgctaaa   1200
tacgtgctag aagcccatgg attgaaacca gttattttaa aaccaaaaga gggcctggca   1260
ctcatcaatg ggacgcagat gatcacatcc ctgggctgtg aagctgtaga gcgagccagt   1320
gctattgcac ggcaggctga cattgtggca gccctgaccc ttgaggtgct gaagggcacc   1380
accaaagcct ttgacactga cattcatgct cttcgacctc accgtgggca aattgaagtt   1440
gcttttcggt ttcggtcact cttggactca gatcaccacc catcagaaat agcagagagt   1500
cacaggttct gtgatcgcgt ccaggatgca tacaccttgc gctgctgtcc acaggtccat   1560
ggtgtggtga atgatacaat agcatttgtg aagaacatca ttaccacaga actgaacagc   1620
gcaacagata atcctatggt ctttgccaat aggggagaga cagttctggg aggaaacttc   1680
catggtgaat acccagccaa agccctagac tacttggcca ttggcatcca tgaacttgct   1740
gcaatcagtg agagaagaat cgagcggctc tgcaatccct ccctcagtga gctgcctgcc   1800
ttcctggtgg ctgaaggtgg tctgaactct gggttcatga tagctcactg cacggcagca   1860
gcccttgttt ctgagaacaa ggctctgtgc catccctcgt ctgttgactc cctctccacc   1920
agcgcagcca cggaggacca cgtctccatg ggaggatggg cagcaaggaa agccctcagg   1980
gtcatcgagc atgtggagca agtgctggcc atcgagctcc ttgcagcctg ccagggcata   2040
gagtttctac gtccctgaa aacaaccact ccgctggaga aggtctatga cctggtgcgc   2100
tctgttgtaa ggtttgggaa gtagctgctc catacattga aaaatacaga atggagcata   2160
ttccagaatc aagaccttct tctccaacag cctttttcact gcaatttctg cacaagaaat   2220
ccaccaaaat cccggagtct gaggaccttt aatgggcttt gtcatgaagt agcagatgag   2280
agggcagtca gtttagcaca aagcaatact aggctgaagg agaacctga gaactttcct   2340
aggtagatca atccattgta tcattcagtt cttctaaagc ctacgttggt taggctgatg   2400
gcagtattat agttgctaaa ttcagcactg tgttcctgtt gtcgtggttc aagacccacc   2460
aggtattttc agattataaa acttttcttt ctttcttaac agtttcaaca ggccactcac   2520
tcttaagggt gagaagaata accacaattg tatgtgcctg tttttactc ttagcattag   2580
atgaattcaa atttggaaac agattgatag caatttttc taaaaacatt agacttttgt   2640
taacctttt tttttttttt aaatttgctt caacaagctc tccaccagtt gactttcttt   2700
```

-continued

```
ggctaatttt actttgcatg atatgcctta atatgcctte ataaataacc attttaagtc    2760
ataatttgtc cttaagctgc tttttttctt cattaattgg atcatagtaa agagtagtca    2820
ataggggtctt cagctattaa ttgtagaggt gattaaaacc aacaaggagt ttcatgtgca   2880
aaggagataa ggaatgaata taaagattgc tatttgggtg gctcttatta aactgtgtat   2940
tttgtactta tcactacacg tatccccccaa atgcttaact gggagtttga ggttagtatt  3000
ttcacttcct tggtgttagt actctattca cattcttatt gtaaccttcc tcatttcaca   3060
gataaggaat ctttggggat taaccaacct ccttttctgta atggtaatca ttaaaataag  3120
tcctattgat aaaggtcaga tggagccccta gagtgtatta ctgcatctat tttttttcccc 3180
gagaagataa aggaccttca gggatggctt aagtgtatct gtccagatga aggatgggtg  3240
acatgacctc ttggcttccc aagtctaagc tctgtgactt tgcaccagtg tgtgcatata   3300
tgtgcaaggc ccttcaagtg gtctgaaacc gtggctctaa aaaccacagc tggtggagag  3360
gaggacagac acacttgcca ccttgcctac ctaattgcca tctaaaatgg gccgaacagt   3420
ggatttcaca atagagtttt cacccttag atttacaact tgtcaggtgg aaactgaagt   3480
gaaaactgct gcacacagca attcaggggag caaaaaatgt gctgaggaga ctgtttacct  3540
aaaggttgtt cttggtgcta ttccttgtca aatgtgaac acacacaaat gagggtttgtg 3600
cattgtcatc cgtgggctgc cattgagcca gtaaccccca gtggtctcat ggtgctcttc  3660
gctccagttt ggggaatgct ggatctttc agcccctgca gccctccagg tcaaaatgac  3720
actttgtcac tgagttttct acacagctct attagtaact gacagcacac gccttcaagg  3780
gaacttcaag ggaaacatgg aataaactaa gtctcaattg cc                      3822
```

SEQ ID NO: 8        moltype = RNA  length = 3825
FEATURE                Location/Qualifiers
source                 1..3825
                          mol_type = genomic RNA
                          organism = Homo sapiens
SEQUENCE: 8

```
agataaagac aggaacatgg tgtttataag ctgcccttaa tggcagagaa cacagacaga    60
aacgagggaa gagagagaaa ttggggaccc tgaagaaagg gggccagcag caggtaggtg    120
ccatcaggga caagaacagc acctcccagg gtggagacc ccaggccttt ctggcagcag    180
gtctggatgg aaagtggaca ggaggctcac ccgtctgcat ccccctgctc tgccctgct    240
cggctacaaa aaccaaaggg acagcagctg accacacccc ggtagccact cctgcataaa   300
gctctcccct cctgtgacca gctgaggacc tcaggctgca gcggagccat gcccagatac   360
acggtgcacg tacgtgggga atggctggca gtgccctgcc aggacgcgca gctcactgtg   420
ggctggctgg gcgggaggc cgtgaggcgc tatatcaaga ataagcccga caatggtggc   480
ttcacctccg tggatgacgc gcacttcctt gtgcgccggt gcaagggcct gggcctgctg   540
gacaacgagg accggctcga ggtggcccta gagaacaacg agttcgtgga agtggttata   600
gagggtgatg ccatgtctcc tgacttcatt ccatctcaac cagaaggagt ttatctatac   660
agcaagtacc gggagcctga aaagtacatc gagttagatg gagaccgtct gaccacggag   720
gatctgatca acttgggaaa gggacgctac aaaataaagc tcaccccaac agctgagaag   780
agggtgcaga aatccaggga ggtcatagat agcatcataa aagagaaaac agggagcttc   840
aggtcaactt agtacgctca cattcttcag gtgttgggaa accactaagt cctgagaggt   900
gtcggatgct cttggcttta aggatcaatg tcttagccaa aggatacagt ggcattcc    960
tggagaccct caaacaagtc atagaaatgt taatgcctc ctgcctgccc tatgtcccag   1020
agaaaggaac cgttggtgcc agtggagacc ttgcccccact ctctcatctt gctcttgggc  1080
tagttggaga agggaagatg tggtctccga agagtggctg ggctgatgct aaatacgtgc   1140
tagaagccca tggattgaaa ccagttattt taaaccaaa agagggcctg gcactcatca    1200
atggggacgca gatgatcaca tccctgggct gtgaagctgt agagcgaggc agtgctattg  1260
cacggcaggc tgacattgtg gcagcccctga cccttgaggt gctgaaggg accaccaaag  1320
cctttgacac tgacattcat gctcttcgac ctcaccgtgg gcaaattgaa gttgcttttc  1380
ggtttcggtc actcttggac tcagatcacc acccatcaga aatagcagag agtcacaggt   1440
tctgtgatcg cgtccaggat gcatacacct tgcgctgctg tccacaggtc catgtgtgg    1500
tgaatgatac aatagcattt gtgaagaaca tcattaccac agaactgaac agcgcaacag  1560
ataatcctat ggtctttgcc aatagggggag agacagtttc tggaggaaac ttccatggtg 1620
aatacccagc caaagcccta gactacttgg ccattggcat ccatgaactt gctgcaatca  1680
gtgagagaag aatcgagcgg ctctgcaatc cctccctcag tggctgcct gccttcctgg   1740
tggctgaagg tggtctgaac tctgggttca tgatagctca ctgcacggca gcagcccttg  1800
tttctgagaa caaggctctg tgccatccct cgtctgttga ctccctctcc accagcgcag  1860
ccacggagga ccacgtctcc atgggaggat gggcagcaag gaaaagccctc agggtcatcg  1920
agcatgtgga gcaagtgctg gccatcgagc tccttgcagc ctgccagggc ataagagtttc  1980
tacgtcccct gaaaacaacc actccgctgg agaaggtcta tgacctggtg cgctctgttg  2040
taaggccctg gataaaagat cgcttcatgg ccccggacat cgaggcagcc cacaggctgc  2100
tcctggagca aaggtttgg gaagtagctg ctccatacat tgaaaaatac agaatggagc   2160
atattccaga atcaagacct ctttctccaa cagccttttc actgcaattt ctgcacaaga  2220
aatccaccaa aatcccggag tctgaggacc tttaatggcg tttgtcatga agtagcaagat 2280
gagagggcag tcagtttagc acaaagcaat actaggctga aggagagacc tgagaacttt  2340
cctaggtaga tcaatccatt gtatcattca gttcttctaa agcctacgtt ggttaggctg  2400
atggcagtat tatagttgct aaattcagca ctgtgttcct gttgtcgtgg ttcaagaccc  2460
accaggtatt ttcagattat aaaacttttc tttctttctt aacagtttca acaggccact  2520
cactcttaag ggtgagaaga ataaccacaa ttgtatgtgc ctgttttta ctcttagcat   2580
tagatgaatt caaatttgga aacagattga tagcaatttt ttctaaaaac attgacttt    2640
tgttaacctt ttttttttttt tttaaattg ctcaacaag ctctccacca gttgactttc   2700
tttggctaat tttactttgc atgatatgcc ttaatatgcc ttcataaata accatttta    2760
gtcataattt gtccttaagc tgcttttttc ttctattaat tggatcatag taagagtag    2820
tcaataggt cttcagctat taattgtaga ggtgattaaa accaacaagg agtttcatgt    2880
gcaaggagga taaggaatga atataaagat tgctatttgg gtggctctta ttaaactgtg    2940
tattttgtac ttatcactac acgtatcccc caaatgctta catgggagtt tgaggttagt    3000
attttcactt ccttggtgtt agtactctat tcacattctt attgtaacct tcctcatttc    3060
acagataagg aatctttggg gattaaccaa cctcctttct gtaatggtaa tcattaaaat   3120
aagtcctatt gataaaggtc agatggagcc ctagagtgta ttactgcatc tatttttttc   3180
```

```
cccgagaaga taaaggacct tcagggatgg cttaagtgta tctgtccaga tgaaggatgg    3240
gtcacatgac ctcttggctt cccaagtcta agctctgtga ctttgcacca gtgtgtgcat    3300
atatgtgcaa ggcccttcaa gtggtctgaa accgtggctc taaaaaccac agctggtgga    3360
gaggaggaca gacacacttg ccaccttgcc tacctaattg ccatctaaaa tgggccgaac    3420
agtggatttc acaatagagt tttcaccctt tagatttaca gctgtcagg tggaaactga    3480
agtgaaaact gctgcacaca gcaattcagg gagcaaaaaa tgtgctgagg agactgttta    3540
cctaaaggtt gttcttggtg ctattccttg tcaaaatgtg aacacacaca aatgaggttt    3600
gtgcattgtc atccgtgggc tgccattgag ccagtaaccc ccagtggtct catggtgctc    3660
ttcgctccag tttggggaat gctggattct ttcagccctt gcagccctcc aggtcaaaat    3720
gacactttgt cactgagttt tctacacagc tctattagta actgacagca cacgccttca    3780
agggaacttc aagggaaaca tggaataaac taagtctcaa ttgcc                     3825

SEQ ID NO: 9             moltype = RNA   length = 3085
FEATURE                  Location/Qualifiers
source                   1..3085
                         mol_type = genomic RNA
                         organism = Homo sapiens
SEQUENCE: 9
agcagcaggt aggtgccatc agggacaaga acagcacctc ccagggtggg agacccagg     60
cctttctggc agcaggtctg gatgaaagt ggacaggagg ctcaccgtc tgcatccct      120
gctcctgccc ctgctcggct acaaaaacca aagggacagc agctgaccac accccggtag    180
ccactcctgc ataaagctct cccctcctgt gaccagctga ggacctcagg ctgcagcgga    240
gccatgccca gatacacggt gcacgtacgt ggggaatggc tggcagtgcc ctgccaggac    300
gcgcagctca ctgtgggctg gctgggccgg gaggccgtga ggcgctatat caagaataag    360
cccgacaatg gtgcttcac ctccgtggat gacgcgcact tccttgtgcg ccggtgcaag    420
ggcctgggcc tgctggacaa cgaggaccgg ctcgaggtgg ccctagagaa caacgagttc    480
gtggaagtgg ttatagaggg tgatgccatg tctcctgact tcattccatc tcaaccagaa    540
ggagtttatc tatacagcaa gtaccggag cctgaaaagt acatcgagtt agatggagac     600
cgtctgacca cggaggatct ggtcaacttg gaaaagggac gctacaaaat aaagctcacc    660
ccaacagctg agaagagggt gcagaaatcc agggaggtca tagatgcat cataaaagag    720
aaaacagttg tttacggtat tactacaggt tttgggaaat tgccagaac tgtaattcct    780
atcaataagc tacaggagct tcaggtcaac ttagtacgct cacattcttc aggtgttggg    840
aaaccactaa gtcctgagag gtgtcggatg ctcttggctt taaggatcaa tgtcttagcc    900
aaaggataca gtggcatttc cctggagacc ctcaaacaag tcatagaaat gtttaatgcc    960
tcctgcctgc cctatgtccc agagaaagga accgttggtg ccagtggaga ccttgcccca   1020
ctctctcatc ttgctcttgg gctagttgga aagggaaga tgtggtctcc gaagagtggc    1080
tgggctgatg ctaaatacgt gctagaagcc catggattga aaccagttat tttaaaacca    1140
aaagagggcc tggcactcat caatgggacg cagatgatca catccctggg ctgtgaagct    1200
gtagagcgag ccagtgctat tgcacggcag gctgacattg tggcagccct gaccttgag    1260
gtgctgaagg gcaccaccaa agcctttgac actgacattc atgctcttcg acctcaccgt    1320
gggcaaattg aagttgcttt tcggtttcgg tcactcttgg actcagatca ccacccatca    1380
gaaatagcag agagtcacag gttctgtgat cgcgtcagg atgcatacac cttgcgctgc    1440
tgtccacagg tccatggtgt ggtgaatgat acaaatgcat ttgtgaagaa catcattacc    1500
acagaactga acagcgcaac agataatcct atggtctttg ccaatagggg agagacagtt    1560
tctgaggaa acttccatgg tgaatacca gccaaagccc tagactactt ggccattggc    1620
atccatgaac ttgctgcaat cagtgagaga agaatcgagc ggctctgcaa tcctcccctc    1680
agtgagctgc ctgccttcct ggtggctgaa ggtggtctga actctgggtt catgatagct    1740
cactgcacgg cagcagccct tgtttctgag aacaaggctc tgtgccatcc ctcgtctgtt    1800
gactccctct ccaccagcgc agccacggag gaccacgtct ccatgggagg atgggcagca    1860
aggaaagccc tcagggtcat cgagcatgtg gagcaagtgc tggccatcga gctccttgca    1920
gcctgccagg gcatagagtt tctacgtccc ctgaaaacaa ccactccgct ggagaaggtc    1980
tatgacctgg tgcgctctgt tgtaaggcc tggataaaag atcgcttcat ggccccggac    2040
atcgaggcag cccacaggct gctcctggag cagaaggttt gggaagtagc tgctccatac    2100
attgaaaaat acagaatgga gcatattcca gaatcaagac ctctttctcc aacagccttt    2160
tcactgcaat ttctgcacaa gaaatccacc aaaatcccgg agtctgagga cctttaatag    2220
gctttgtcat gaagtagcag atgagagggc agtcagttta gcacaaagca atactaggct    2280
gaaggagaga cctgagaact ttcctaggta gatcaatcca ttgtatcatt cagttcttct    2340
aaagcctacg ttggttaggc tgatggcagt attatagttg ctaaattcag cactgtgttc    2400
ctgttgtcgt ggttcaagac ccaccaggta ttttcagatt ataaaactt tcttttcttc    2460
ttaacagttt caacaggcca ctcactctta agggtgagaa gaataaccac aattgtatgt    2520
gcctgttttt tactccttag cattagatgaa ttcaaatttg gaaacagatt gatagcaatt    2580
ttttctaaaa acattagact tttgttaacc tttttttttt ttttaaatt tgcttcaaca    2640
agctctccac cagttgactt tctttggcta atttactttt gcatgatatg ccttaatatg    2700
ccttcataaa taaccatttt aagtcataat ttgtccttaa gctgctttt tcttctatta    2760
attggatcat agtaaagagt agtcaatagg gtcttcagct attaattgta gaggtgatta    2820
aaaccaacaa ggagtttcat gtgcaaagga gataaggaat gaatataaag attgctattt    2880
gggtggctct tattaaactg tgtatttgt acttatcact acacgtatcc cccaaatgct    2940
tacatgggag tttgaggtta gtattttcac ttccttggtg ttagtactct attcacattc    3000
ttattgtaac cttcctcatt tcacagataa ggaatctttg gggattaacc aacctccttt    3060
ctgtaatggt aatcattaaa ataag                                          3085

SEQ ID NO: 10            moltype = RNA   length = 2804
FEATURE                  Location/Qualifiers
source                   1..2804
                         mol_type = genomic RNA
                         organism = Homo sapiens
SEQUENCE: 10
agacagaaac gagggaagag agagaaattg gggaccctga agaaggggg ccagcagcag     60
gtaggtgcca tcagggacaa gaacagcacc tcccagggtg ggagacccca ggcctttctg    120
```

```
gcagcaggtc tggatggaaa gtggacagga ggctcacccg tctgcatccc ctgctcctgc    180
ccctgctcgg ctacaaaaac caaagggaca gcagctgacc acaccccggt agccactcct    240
gcataaagct ctcccctcct gtgaccagct gaggacctca ggctgcagcg gagccatgcc    300
cagatacacg gtgcacgtac gtggggaatg gctggcagtg ccctgccagg acgcgcagct    360
cactgtgggc tggctgggcc gggaggccgt gaggcgctat atcaagaata agcccgacaa    420
tggtggcttc acctccgtgg atgacgcgca cttccttgtg cgccggtgca agggcctggg    480
cctgctggac aacgaggacc ggctcgaggt ggccctagag aacaacgagt tcgtggaagt    540
ggttatagag ggtgatgcca tgtctcctga cttcattcca tctcaaccag aaggagttta    600
tctatacagc aagtaccggg agcctgaaaa gtacatcgag ttagatggag accgtctgac    660
cacggaggat ctggtcaact tgggaaaggg acgctacaaa ataaagctca cccccaacagc    720
tgagaagagg gtgcagaaat ccagggaggt catagatagc atcataaaag agaaaacagg    780
gagcttcagg tcaacttagt acgctcacat tcttcaggtg ttgggaaacc actaagtcct    840
gagaggtgtc ggatgctctt ggctttaagg atcaatgtct tagccaaagg atacagtggc    900
atttccctgg agaccctcaa acaagtcata gaaatgttta atgcctcctg cctgccctat    960
gtcccagaga aaggaaccgt tggtgccagt ggagaccttg ccccactctc tcatcttgct   1020
cttgggctag ttgagaagg gaagatgtgg tctccgaaga gtggctgggc tgatgctaaa   1080
tacgtgctag aagcccatgg attgaaacca gttattttaa aaccaaaga gggcctggca   1140
ctcatcaatg ggacgcagat gatccatatc ctgggctgtg aagctgtaga gcgagccagt   1200
gctattgcac ggcaggctga cattgtggca gccctgaccc ttgaggtgct gaagggcacc   1260
accaaagcct ttgacactga cattcatgct cttgacctc accgtgggca aattgaagtt   1320
gcttttcggt ttcggtcact cttggactca gatcaccacc catcagaaat agcagagagt   1380
cacaggttct gtgatcgcgt ccaggatgca tacaccttgc gctgctgtcc acaggtccat   1440
ggtgtggtga atgatacaat agcatttgtg aagaacatca ttaccacaga actgaacagc   1500
gcaacagata atcctatggt ctttgccaat aggggagaga caatttctgg aggaaacttc   1560
catggtgaat acccagccaa agcctagac tacttggcca ttggcatcca tgaacttgct   1620
gcaatcagtg agagaagaat cgagcggctc tgcaatccc ccctcagtga gctgcctgca   1680
ttcctggtgg ctgaaggtgg tctgaactct gggttcatga tagctcactg cacggcagca   1740
gcccttgttt ctgagaacaa ggctctgtgc catccctcgt ctgttgactc cctctccacc   1800
agcgcggcca cggaggacca cgtctccatg ggaggatggg cagcaaggaa agccctcagg   1860
gtcatcgagc atatggagca agtgctggcc atcgagctcc ttgcagcctg ccagggcata   1920
gagtttctac gtcccctgaa aacaaccact ccgctggaga aggtctatga cctggtgcgc   1980
tctgttgtaa ggcccctggat aaaagatcgc ttcatggccc cggacatcga ggcagcccac   2040
aggctgctcc tggagcagaa ggtttgggaa gtagctgctc catacattga aaaatacaga   2100
atggagcata ttccagaatc aagacctctt tctccaacag cctttcact gcaatttctg   2160
cacaagaaat ccaccaaaat cccggatgtc gaggacctt aatgggcttt gtcatgaagt   2220
agcagatgag agggcagtca gtttagcaca aagcaatact aggctgaagg agagacctga   2280
gaactttcct aggtagatca atccattgta tcattcagtt cttctaaagc ctacgttggt   2340
taggctgatg gcagtattat agttgctaaa ttcagcactg tgttcctgtt gtcgtggttc   2400
aagacccacc aggtattttc agattataaa acttttcttt ctttcttaac agtttcaaca   2460
ggccactcac tcttaagggt gagaagaata accacaattg tatgtgcctg tttttttactc   2520
ttagcattag atgaattcaa atttggaaac agattgatag caatttttc taaaaacatt   2580
agacttttgt taacctttttt tttttttttt aaatttgctt caacaagctc tccaccagtt   2640
gacttttcttt ggctaatttt actttgcatg atatgcctta atatgccttc ataaataacc   2700
atttttaagtc ataatttgtc cttaagctgc ttttttcttc tattaattgg atcatagtaa   2760
agagtagtca ataggggtctt cagctattaa ttgtagaggt gatt                  2804

SEQ ID NO: 11         moltype = RNA   length = 1474
FEATURE               Location/Qualifiers
source                1..1474
                      mol_type = genomic RNA
                      organism = Homo sapiens
SEQUENCE: 11
gagtaatctc agataaagac aggaacatgg tgtttataag ctgcccttaa tggcagagaa     60
cacagacaga aacgagggaa gagagagaaa ttggggaccc tgaagaaagg gggccagcag    120
caggtaggtg ccatcaggga caagaacagc acctcccagg gtgggagacc ccaggccttt    180
ctggcagcag gtctggatgg aaagtggaca ggaggcctcac ccgtctgcat cccctgctgc    240
tgccccctgct cgcctacaaa aaccaaaggg acagcagctg accacacccc ggtagccact    300
cctgcataaa gctctccctc ctgtgaccag ctgaggaccc tcaggctgca gcggagccat    360
gcccagatac acggtgcacg tacgtgggga atggctggag gaaacttcca tggtgaatac    420
ccagccaaag ccctagacta cttggccatt ggcatccatg aacttgctgc aatcagtgag    480
agaagaatcg agcggctctg caatccctcc tcagtgagc tgcctgcctt cctggtggtc    540
gaaggtggtc tgaactctgg gttcatgata gctcactgcg gcagcagc ccttgtttct    600
gagaacaagg ctctgtgcca tcccctcgtct gttgactccc ctccaccag cgcagccacg    660
gaggaccacg tctccatggg aggatgggca gcaaggaag ccctcaggt catcgagcat    720
gtggagcaag tgctggccat cgagctcctt gcagcctgcc agggcataga gtttctacgt    780
ccctgaaaa caaccactcc gctggagaag gtctatgacc tggtgcgctc tgttgtaagg    840
ccctggataa aagatcgctt catgccccg gacatcgagg cagcccacag gctgctccca    900
gagcagaagg tttgggaagt agctgctcca tacattgaaa atacagaat ggagcatatt    960
ccagaatcaa gacctctttc tccaacagct tttcactgc aatttctgca caagaaatcc    1020
accaaaatcc cggagtctga ggaccttta atgggctttgt catgaagtag cagatgagag    1080
ggcagtcagt ttagcacaaa gcaatactag gctgaaggag agacctgaga acttttcctag    1140
gtagatcaat ccattgtata attcagttct tctaaagcct acgttggtta ggccgatgc    1200
agtattatag ttgctaaatt cagcactgtg ttcctgttgt cgtggttcaa gacccaccag    1260
gtattttcag attataaac ttttcttct tccttaacag tttcaacagg ccactcactc    1320
ttaagggtga agaataac cacaattgta tgtgcctgtt tttactctt agcattagac    1380
gaattcaaat tggaaacag attgatagca atttttctta aaaacattag acttttgtta    1440
acctttttttt tttttttt tttaaatttg cttc                                1474
```

```
SEQ ID NO: 12         moltype = RNA  length = 2271
FEATURE               Location/Qualifiers
source                1..2271
                      mol_type = genomic RNA
                      organism = Homo sapiens
SEQUENCE: 12
gccatcaggg acaagaacag cacctcccag ggtgggagac cccaggcctt tctggcagca  60
ggtctggatg gaaagtggac aggaggctca cccgtctgca tccctgctc ctgcccctgc  120
tcggctacaa aaaccaaagg gacagcagct gaccacaccc cggtagccac tcctgcataa  180
agctctcccc tcctgtgacc agctgaggac ctcaggctgc agcggagcca tgcccagata  240
cacggtgcac gtacgtgggg aatggctggc agtgccctgc caggacgcgc agctcactgt  300
gggctggctg ggccgggagg ccgtgaggcg ctatatcaag aataagcccg acaatggtgg  360
cttcacctcc gtggatgacg cgcacttcct tgtgcgccgg tgcaagggcc tgggcctgct  420
ggacaacgag gaccggctcg aggtggccct agagaacaac gagttcgtgg aagtggttat  480
agagggtgat gccatgtctc ctgacttcat tccatctcaa ccagaaggag tttatctata  540
cagcaagtac cgggagcctg aaaagtacat cgagttagat ggagaccgtc tgaccacgga  600
ggatctggtc aacttgggaa agggacgcta caaaataaag ctcacccca cagctgagaa  660
gagggtgcag aaatccaggg aggtcataga tagcatcata aaagagaaaa cagggagctt  720
caggtcaact tagtacgctc acattcttca ggtgttggga aaccactaag tcctgagagg  780
tgtcggatgc tcttggcttt aaggatcaat gtcttagcca aaggatacag tggcatttcc  840
ctggagaccc tcaaacaagt catagaaatg tttaatgcct cctgcctgcc ctatgtccca  900
gagaaaggaa ccgttggtgc cagtggagac cttgccccgc tctctcatct tgctcttggg  960
ctagttggag aagggaagat gtggtctccg aagagtggct gggctgatgc taaatacgtg  1020
ctagaagccc atgattgaa accagttatt ttaaaaccaa agagggcct ggcactcatc  1080
aatggagacc agatgatcac atccctgggc tgtgaagctg tagagcgagc cagtgctatt  1140
gcacggcagg ctgacattgt ggcagccctg acccttgagg tgctgaaggg caccaccaaa  1200
gcctttgaca ctgacattca tgctcttcga cctcaccgtg gcaaattga agttgctttt  1260
cggtttcggt cactcttgga ctcagatcac cacccatcag aaatagcaga gagtcacagg  1320
ttctgtgatc gcgtccagga tgcatacacc ttgcgctgct gtccacaggt ccatggtgtg  1380
gtgaatgata caatagcatt tgtgaagaac atcattacca cagaactgaa cagcgcaaca  1440
gataatccta tggtctttgc caataggga gagacaattt ctggaggaaa cttccatggc  1500
cctagactac ttgccattg gcatccatga acttgctgca atcagtgaga aagaatcga  1560
gcggctctgc aatccctccc tcagtgagct gcctgcctc tcggtggctg aaggtggtct  1620
gaactctggg ttcatgatag ctcactgcac ggcagcagcc cttgttttcg agaacaaggc  1680
tctgtgccat ccctcgtctg ttgactccct ctccaccagc gcagccacgg aggaccacgt  1740
ctccatggga ggatgggcag caaggaaagc cctcagggtc atcgagcatg tggagcaagt  1800
gctggccatc gagctccttg cagcctgcca gggcatagag tttctacgtc ccctgaaaac  1860
aaccactccg ctggagaagg tctatgacct ggtgcgctct gtttgtaagg ccctggataa  1920
agatcgcttc atggccccgg acatcgaggc agcccacagg ctgctcctgg agcagaaggt  1980
ttgggaagta gctgctccat acattgaaaa atacagaatg gagcatattc cagaatcaag  2040
acctcttttct ccaacagcct tttcactgca atttctgcac aagaaatcca ccaaaatccc  2100
ggagtctgag gacctttaat gggctttgtc atgaagtagc agatgagagg gcagtcagtt  2160
tagcacaaag caatactagg ctgaaggaga gacctgagaa cttcctagg tagatcaatc  2220
cattgtatca ttcagttctt ctaaagccta cgttggttag gctgatggca g            2271

SEQ ID NO: 13         moltype = RNA  length = 2355
FEATURE               Location/Qualifiers
source                1..2355
                      mol_type = genomic RNA
                      organism = Homo sapiens
SEQUENCE: 13
gccatcaggg acaagaacag cacctcccag ggtgggagac cccaggcctt tctggcagca  60
ggtctggatg gaaagtggac aggaggctca cccgtctgca tccctgctc ctgcccctgc  120
tcggctacaa aaaccaaagg gacagcagct gaccacaccc cggtagccac tcctgcataa  180
agctctcccc tcctgtgacc agctgaggac ctcaggctgc agcggagcca tgcccagata  240
cacggtgcac gtacgtgggg aatggctggc agtgccctgc caggacgcgc agctcactgt  300
gggctggctg ggccgggagg ccgtgaggcg ctatatcaag aataagcccg acaatggtgg  360
cttcacctcc gtggatgacg cgcacttcct tgtgcgccgg tgcaagggcc tgggcctgct  420
ggacaacgag gaccggctcg aggtggccct agagaacaac gagttcgtgg aagtggttat  480
agagggtgat gccatgtctc ctgacttcat tccatctcaa ccagaaggag tttatctata  540
cagcaagtac cgggagcctg aaaagtacat cgagttagat ggagaccgtc tgaccacgga  600
ggatctggtc aacttgggaa agggacgcta caaaataaag ctcacccca cagctgagaa  660
gagggtgcag aaatccaggg aggtcataga tagcatcata aaagagaaaa cagttgttta  720
cggtattact acaggttttg ggaaatttgc cagaactgta attcctatca ataagctaca  780
ggagcttcag gtcaacttag tacgctcaca ttcttcaggt gttgggaaac cactaagtcc  840
tgagaggtgt cggatgctct tggctttaag gatcaatgtc ttagccaaag gatacagtgg  900
catttccctg gagaccctca aacaagtcat agaaatgttt aatgcctcct gcctgcccta  960
tgtcccagag aaaggaaccg ttggtgccag tggagacctt gccccactct ctcatcttgc  1020
tcttgggcta gttggagaag ggaagatgtg gtctccgaag agtggctggg ctgatgctaa  1080
atacgtgcta gaagcccatg gattgaaacc agttatttta aaaccaaaag agggcctggc  1140
actcatcaat gggacgcaga tgatcacatc cctgggctgt gaagctgtag agcgagccag  1200
tgctattgca cggcaggctg acattgtggc agccctgacc cttgaggtgc tgaagggcac  1260
caccaaagcc tttgacactg acattcatgc tcttcgacct caccgtgggc aaattgaagt  1320
tgcttttcgg tttcggtcac tcttggactc agatcaccac ccatcagaaa tagcagagag  1380
tcacaggttc tgtgatcgcg tccaggatgc atacaccttg cgctgctgtc cacaggtcca  1440
tggtgtggtg aatgatacaa tagcatttgt gaagaacatc attaccacag aactgaacag  1500
cgcaacagat aatcctatgg tctttgccaa taggggagag acaatttctg gaggaaactt  1560
ccatggtgaa tacccagcca aagccctaga ctacttggcc attggcatcc atgaacttgc  1620
```

```
tgcaatcagt gagagaagaa tcgagcggct ctgcaatccc tccctcagtg agctgcctgc   1680
cttcctggtg gctgaaggtg gtctgaactc tgggttcatg atagctcact gcacggcagc   1740
agcccttgtt tctgagaaca aggctctgtg ccatccctcg tctgttgact ccctctccac   1800
cagcgcagcc acgaggacc acgtctccat gggaggatgg gcagcaagga aagccctcag    1860
ggtcatcgag catgtggagc aagtgctggc catcgagctc cttgcagcct gccagggcat   1920
agagtttcta cgtcccctga aaacaaccac tccgctggag aaggtctatg acctggtgcg   1980
ctctgttgta aggccctgga taaaagatcg cttcatggcc ccggacatcg aggcagccca   2040
caggctgctc ctggagcaga aggtttggga agtagctgct ccatacattg aaaaatacag   2100
aatggagcat attccagaat caagacctct ttctccaaca gccttttcac tgcaatttct   2160
gcacaagaaa tccaccaaaa tcccggagtc tgaggacctt taatgggctt tgtcatgaag   2220
tagcagatga gagggcagtc agtttagcac aaagcaatac taggctgaag gagagacctg   2280
agaactttcc taggtagatc aatccattgt atcattcagt tcttctaaag cctacgttgg   2340
ttaggctgat ggcag                                                    2355

SEQ ID NO: 14          moltype = RNA   length = 3913
FEATURE                Location/Qualifiers
source                 1..3913
                       mol_type = genomic RNA
                       organism = Homo sapiens
SEQUENCE: 14
gttttacagt tgagtaatct cagataaaga caggaacatg gtgtttataa gctgccctta     60
atggcagaga acacagacag aaacgaggga agagagagaa attggggaac ctgaagaaag    120
ggggccagca gcaggtaggt gccatcaggg acaagaacag cacctcccag ggtgggagac    180
cccaggcctt tctggcagca ggtctggatg gaaagtggac aggaggctca cccgtctgca    240
tccccctgct ctgcccctgc tcggctacaa aaaccaaagg gacagcagct gaccacaccc    300
cggtagccac tcctgcataa agctctcccc tcctgtgacg agtgctgagg ctcaggctgg    360
agcggagcca tgcccagata cacggtgcac gtacgtgggg aatggctggc agtgccctgc    420
caggacgcgc agctcactgt gggctggctg ggcggagg ccgtgaggcg ctatatcaag       480
aataagcccg acaatggtgg cttcacctcc gtggatgacg cgcacttcct tgtgcgccgg    540
tgcaaggggcc tgggcctgct ggacaacgag gaccggctcg aggtggccct agagaacaac   600
gagttcgtgg aagtggttat agagggtgat gccatgtctc ctgacttcat tccatctcaa    660
ccagaaggag tttatctata cagcaagtac cgggagcctg aaaagtacat cgagttagat    720
ggagaccgtc tgaccacgga ggatctggtc aacttgggaa agggacgcta caaaataaag    780
ctcaccccaa cagctgagaa gagggtgcag aaatccaggg aggtcagtag tagcatcata    840
aaagagaaaa cagttgttta cggtattact acaggttttg ggaaatttgc cagaactgta    900
attcctatca ataagctaca ggagcttcag gtcaacttag tacgctcaca ttcttcaggt    960
gttgggaaac cactaagtcc tgagaggtgt cggatgctct tggcttttaag gatcaatgtc   1020
ttagccaaag gatacagtgg catttccctg gagaccctca aacaagtcat agaaatgttt   1080
aatgcctcct gcctgcccta tgtcccagag aaaggaaccg ttgtgccag tggagaccct   1140
gccccactct ctcatcttgc tcttgggcta gttggaaag ggagatgtgt gtctccgaag     1200
agtggctggg ctgatgctaa atacgtgcta gaagcccatg gattgaaacc agttatttta   1260
aaaccaaaag agggcctggc actcatcaat gggacgagaa tgatcacatc cctgggctgt   1320
gaagctgtag agcgagccag tgctattgca cggcaggctg acattgtgcc agcccctgtc   1380
cttgaggtgc tgaagggcac caccaaagcc tttgacactg acattcatgc tcttcgacct   1440
caccgtgggc aaaattgaagt tgcttttcgg tttcggtcac tcttggactc agatcaccac   1500
ccatcagaaa tagcagagag tcacaggttc tgtgatcgcg tccaggatgc atacaccttg   1560
cgctgctgtc cacaggtcca tggtgtggtg aatgatacaa tagcatttgt gaagaacatc   1620
attaccacag aactgaacag cgcaacagat aatcctatgg tctttgccaa taggggagag   1680
acagtttctg gaggaaactt ccatggtgaa taccagcca aagccctaga ctacttggcc     1740
attggcatcc atgaacttgc tgcaatcagt gagagaagaa tcgagcggct ctgcaatccc   1800
tccctcagtg agctgcctgc cttcctggtg gctgaaggtg gtctgaactc tgggttcatg    1860
atagctcact gcacggcagc agcccttgtt tctgagaaca aggctctgtg ccatccctcg   1920
tctgttgact ccctctccac cagcgcagcc acgaggacc acgtctccat gggaggatgg    1980
gcagcaagga aagccctcag ggtcatcgag catgtggagc aagtgctggc catcgagctc   2040
cttgcagcct gccagggcat agagtttcta cgtcccctga aaacaaccac tccgctggag   2100
aaggtctatg acctggtgcg ctctgttgta aggccctgga taaaagatcg cttcatggcc   2160
ccggacatcg aggcagccca caggctgctc ctggagcaga aggtttggga agtagctgct   2220
ccatacattg aaaaatacag aatggagcat attccagaat caagacctct ttctccaaca   2280
gccttttcac tgcaatttct gcacaagaaa tccaccaaaa tcccggagtc tgaggacctt   2340
taatgggctt tgtcatgaag tagcagatga gagggcagtc agtttagcac aaagcaatac   2400
taggctgaag gagagacctg agaactttcc taggtagatc aatccattgt atcattcagt   2460
tcttctaaag cctacgttgg ttaggctgat ggcagtatta tagttgctaa attcagcact   2520
gtgttcctgt tgtcgtggtt caagacccac caggtatttt cagattataa acttttcttt   2580
tcttcttaa cagtttcaac aggccactca tcttaaggg tggaagaat aaccacaatt      2640
gtatgtgcct gttttttact cttagcatta tgaattcaa aatttggaaa cagattgata    2700
gcaatttttt ctaaaaacat tagactttg ttaaccttt tttttttttt taaatttgct     2760
tcaacaagct ctccaccagt tgactttctt ggctaattt tactttgcat gatatgcctt    2820
aatatgcctt cataaataac cattttaagt cataatttgt cctaagctg cttttttttt    2880
ctattaattg gatcatagta aagagtagtc aatagggtct tcagtctatta attgtagagg   2940
tgattaaaac caacaaggag tttcatgtgc aaaggagata aggaatgaat ataaagattg    3000
ctatttgggt ggctcttatt aaactgtgta ttttgtactt atcactacac gtatccccca    3060
aatgcttaca tgggagttg aggttagtat tttcacttcc ttggtgttag tactctattc      3120
acattcttat tgtaaccttc tcatttcac agataaggaa tctttgggga ttaaccaacc     3180
tccttttcgt aatggtaatc attaaaataa gtcctattga taaaggtcag atggagccct    3240
agagtgtatt actgcatcta tttttttccc cgagaagata aaggaccttc agggatggct    3300
taagtgtatc tgtccagatg aaggatgggt cacatgacct cttggcttcc caagtctaag    3360
ctctgtgact ttgcaccagt gtgtgcatat atgtgcaagg cccttcaagt ggtctgaaac    3420
cgtggctcta aaaccacag ctggtggaga ggaggacaga cacacttgcc accttggcta     3480
cctaattgcc atctaaaatg ggccgaacag tggatttcac aatagagttt tcacccttta   3540
```

```
gatttacaac ctgtcaggtg gaaactgaag tgaaaactgc tgcacacagc aattcaggga   3600
gcaaaaaatg tgctgaggag actgtttacc taaaggttgt tcttggtgct attccttgtc   3660
aaaatgtgaa cacacacaaa tgaggtttgt gcattgtcat ccgtgggctg ccattgagcc   3720
agtaaccccc agtggtctca tggtgctctt cgctccagtt tggggaatgc tggattcttt   3780
cagcccctgc agccctccag gtcaaaatga cactttgtca ctgagttttc tacacagctc   3840
tattagtaac tgacagcaca cgccttcaag ggaacttcaa gggaaacatg gaataaacta   3900
agtctcaatt gcc                                                      3913

SEQ ID NO: 15           moltype = DNA    length = 3892
FEATURE                 Location/Qualifiers
source                  1..3892
                        mol_type = genomic DNA
                        organism = Homo sapiens
SEQUENCE: 15
agataaagac aggaacatgg tgtttataag ctgcccttaa tggcagagaa cacagacaga     60
aacgagggaa gagagagaaa ttggggaccc tgaagaaagg gggccagcag caggtaggtg    120
ccatcaggga caagaacagc acctcccagg gtgggagacc ccaggccttt ctggcagcag    180
gtctggatgg aaagtggaca ggaggctcac ccgtctgcct ccccctgctc tgccctgct    240
cggctacaaa aaccaaaggg acagcagctg accacacccc ggtagccact cctgcataaa    300
gctctcccct cctgtgacca gctgaggacc tcaggctgca gcggagccat gcccagatac    360
acggtgcacg tacgtgggga atggctggca gtgccctgcc aggacgcgca gctcactgtg    420
ggctggctgg gccgggaggc cgtgaggcgc tatatcaaga ataagcccga caatggtagc    480
ttcacctccg tggatgacgc gcacttcctt gtgcgccggt gcaagggcct gggcctgctg    540
gacaacgagg accggctcga ggtggcccta gagaacaacg agtcgtggaa gtggttata    600
gagggtgatg ccatgtctcc tgacttcatt ccatctcaac cagaaggagt ttatctatac    660
agcaagtacc gggagcctga aaagtacatc gagttagatg gagaccgtct gaccacggag    720
gatctggtca acttgggaaa gggacgctac aaaaataaag ctcaccccaa agctgagaag    780
agggtgcaga atccaggga ggtcatagat agcatcataa agagaaaac agttgtttac    840
ggtattacta caggttttgg gaaatttgcc agaactgaa ttcctatcaa taagctacag    900
gagcttcagg tcaacttagt acgctcacat tcttcaggtg ttgggaaacc actaagtcgt    960
gagaggtgtc ggatgctctt ggctttaagg atcaatgtct tagccaaagg atacagtggc   1020
atttccctgg agaccctcaa acaagtcata gaaatgttta atgcctcctg cctgccctat   1080
gtcccagaga aggaaccgt tggtgccagt ggagaccttg ccccactctc tcatcttgct   1140
cttgggctag ttggagaagg gaagatgtgg tctccgaaga gtggctgggc tgatgctaaa   1200
tacgtgctag aagccctatg attgaaacca gttatttaa aaccaaaaga gggcctggca   1260
ctcatcaatg ggacgcagat gatcacatcc ctgggctgtg aagctgtaga ggcgagccagt   1320
gctattgcac ggcaggctga cattgtgcca gccctgaccc ttgaggtgct gaagggcacc   1380
accaaagcct ttgacactga cattcatgct cttcgacctc accgtgggca aattgaagtt   1440
gcttttcggt ttcggtcact cttggactca gatcaccacc catcagaaat agcagagagt   1500
cacaggttct gtgatcgcgt ccaggatgca tacaccttgc gctgctgtcc acaggtccat   1560
ggtgtggtga atgatacaat agcatttgtg aagaacatca ttaccacaga actgaacagc   1620
gcaacagata atcctatggt ctttgccaat aggggagaga cagtttctgg aggaaacttc   1680
catggtgaat acccagccaa agccctagac tacttggtca ttggcatcca tgaacttgct   1740
gcaatcagtg agagaagaat cgagcggctc tgcaatccct ccctcagtga gctgcctgcc   1800
ttcctggtgg ctgaaggtgg tctgaactct gggttcatga tagctcactg cacggcagca   1860
gcccttgttt ctgagaacaa ggctctgtgc catccctcgt ctgttgactc cctctccacc   1920
agcgcagcca cggaggacca cgtctccatg ggaggatggg cacaaggaa agccctcagg   1980
gtcatcgagc atgtggagca agtgctggcc atcgagtcc ttgcagcctg cagggcata   2040
gagtttctac gtcccctgaa aacaaccact ccgctggaga aggtctatga cctggtgcgc   2100
tctgttgtaa ggccctggat aaaagatcgc ttcatggccc cggacatcga ggcagcccac   2160
aggctgctcc tggagcagaa ggtttgggaa gtagctgctc catacattga aaatacagga   2220
atggagcata ttccagaatc aagacctctt tctccaacag cctttcact gcaatttctg   2280
cacaagaaat ccaccaaaat cccggagtct gaggaccttt aatgggcttt gtcatgaagt   2340
agcagatgag agggcagtca gtttagcaca aagcaatact aggctgaagg agagacctga   2400
gaacttttcct aggtagatca atccattgta tcattcagtc cttctaaagc ctacgttggt   2460
taggctgatg gcagtattat agttgctaaa ttcagcactg tgttcctgtt gtcgtggttc   2520
aagacccacc aggtatttc agattataaa acttttcttt cttcttaac agtttcaaca   2580
ggccactcac tcttaagggt gagaagaata accacaattg tatgtgcctg ttttttactc   2640
ttagcattag atgaattcaa aatttggaaac agattgatag caatttttc taaaaacatt   2700
agacttttgt taacctttt tttttttt aaatttgctt caacaagctc tccaccagtt   2760
gactttcttt ggctaatttt actttgcatg atatgcctta atatgccttc ataaataacc   2820
atttttaagtc ataatttgtc cttaagctgc ttttttcttc tattaattgg atcatagtaa   2880
agagtagtca atagggtctt cagctattaa ttgtagaggt gattaaaacc aacaaggagt   2940
ttcatgtgca aaggagataa ggaatgaata taaagattgc tatttgggtg gctcttatta   3000
aactgtgtat tttgtactta tcactacacg tatccccca atgcttacat gggagttga   3060
ggttagtatt ttcacttcct tggtgttagt actctattca cattcttatt gtaaccttcc   3120
tcatttcaca gataaggaat ctttgggat taaccaacct cctttctgta atggtaatca   3180
ttaaaataag tcctattgat aaaggtcaga tggagcccta gagtgtatta ctgcatctat   3240
ttttttcccc gagaagataa aggacctca gggatggctt aagtgtatct gtccagatga   3300
aggatgggtc acatgacctc ttggcttccc aagtctaagc tctgtgactt tgcaccagtg   3360
tgtgcatata tgtgcaaggc ccttcaagtg tctgaaacc gtggctctaa aaaccacagc   3420
tggtggagag gaggacagac acacttgcca ccttgcctac ctaattgcca tctaaaatgg   3480
gccgaacagt ggattcaca atagagtttt cacccttag atttacaacc tgtcaggtgg   3540
aaactgaagt gaaaactgct gcacacagca attcaggga gcaaaaatg tgctgaggag   3600
ctgtttacct aaaggttgtt cttggtgcta ttccttgtca aaatgtgaac acacacaaat   3660
gagtttgtg cattgtcatc cgtgggctgc cattgagcca gtaaccccca gtggtctcat   3720
ggtgctcttc gctccagttt ggggaatgct ggattcttc agccctgca gcctccagg   3780
tcaaaatgac actttgtcac tgagttttct acacagctct attagtaact gacagcacac   3840
gccttcaagg gaacttcaag ggaaacatgg aataaactaa gtctcaattg cc             3892
```

| SEQ ID NO: 16 | moltype = DNA length = 3846 |
|---|---|
| FEATURE | Location/Qualifiers |
| source | 1..3846 |
| | mol_type = genomic DNA |
| | organism = Homo sapiens |

SEQUENCE: 16

```
gttttacagt tgagtaatct cagataaaga caggaacatg gtgtttataa gctgcccttc     60
atggcagaga acacagacag aaacgaggga agagagagaca attggggacc ctgaagaaag    120
ggggccagca gcaggtaggt gccatcaggg acaagaacag cacctcccag ggtgggagac    180
cccaggcctt tctggcagca ggtctggatg gaaagtggac aggaggctca cccgtctgca    240
tccctgctc ctgccctgc tcggctacaa aaccaaagg gacagcagct gaccacaccc        300
cggtagccac tcctgcataa agctctcccc tcctgtgacc agctgaggac ctcaggctgc    360
agcggagcca tgcccagata cacggtgcac gtacgtgggg aatggctgac agtgccctgc    420
caggacgcgc agctcactgt gggctggctg ggccgggagg ccgtgaggcg ctatatcaag    480
aataagcccg acaatggtgg cttcacctcc gtggatgacg cgcacttcct tgtgcgccgg    540
tgcaagggcc tgggcctgct ggacaacgag gaccggctcg aggtggccct agagaacaac    600
gagttcgtgg aagtggttat agagggtgat gccatgtctc ctgacttcat tccatctcaa    660
ccagaaggag tttatctata cagcaagtac cgggagcctg aaaagtacat cgagttagat    720
ggagaccgtc tgaccacgga ggatctggtc aacttgggaa agggacgcta caaaataaag    780
ctcaccccaa cagctgagaa gagggtgcag aaatccaggg aggtcataga tagcatcata    840
aaagagaaaa cagggagctt caggtcaact tagtacgctc acattcttca ggtgttggga    900
aaccactaag tcctgagagg tgtcggatgc tcttggcttt aaggatcaat gtcttagcca    960
aaggatacag tggcattttcc ctggagaccc tcaaacaagt catagaaatg tttaatgcct   1020
cctgcctgcc ctatgtccca gagaaaggaa ccgttgtgc cagtggagac cttgccccac   1080
tctctcatct tgctcttggg ctagttggag aagggaagat gtggtctccg aagagtggct   1140
gggctgatgc taaatacgtg ctagaagccc atggattgaa accagttatt ttaaaaccaa   1200
aagagggcct ggcactcatc aatgggacgc agatgatcac atccctgggc tgtgaagctg   1260
tagagcgagc cagtgctatt gcacggcagg ctgacattgt ggcagccctg acccttgagg   1320
tgctgaaggg caccaccaaa gcctttgaca ctgacatcga tgctcttcga cctcaccgtg   1380
ggcaaattga agttgctttt cggtttcggt cactcttgga ctcagatcac cacccatcag   1440
aaatagcaga gagtcacagg ttctgtgatc gcgtccagga tgcatacacc ttgcgctgct   1500
gtccacaggt ccatggtgtg gtgaatgata caatagcatt tgtgaagaac atcattacca   1560
cagaactgaa cagcgcaaca gataatccta tggtcttttga caatagggga gagacagttt   1620
ctggaggaaa cttccatggt gaatacccag ccaaagccct agactacttg gccattggca   1680
tccatgaact tgctgcaatc agtgagagaa gaatcgagcg gctctgcaat ccctccctca   1740
gtgagctgcc tgccttcctg gtggctgaag gtggtcgaa ctctgggttc atgatagctc   1800
actgcacggc agcagccctt gtttctgaga caaggctct gtgccatccc tcgtctgttg   1860
actccctcc caccagcgca gccacggagg accacgtct catggaggga tgggcagcaa   1920
ggaaagccct cagggtcatc gagcatgtgg agcaagtgct ggccatcgag ctccttgcag   1980
cctgccaggg catagagttt ctacgtcccc tgaaaacaac cactccgctg gagaaggtct   2040
atgacctggt gcgctctgtt gtaaggccct ggataaaaga tcgcttcatg gccccggaca   2100
tcgaggcagc ccacaggctg ctcctggagc agaaggtttg ggaagtagct gctccataca   2160
ttgaaaaata cagaatggag catattccag aatcaagacc tctttctcca acagcctttt   2220
cactgcaatt tctgcacaag aaatccacca aaatcccgga gtctgaggac ctttaatggg   2280
cttttgtcatg aagtagcaga tgagagggca gtcagtttga cacaaagcaa tactaggctg   2340
aaggagagac ctgagaactt tcctaggtag atcaatccat tgtatcattc agttcttcta   2400
aagcctacgt tggttaggct gatggcagta ttatagttgc taaattcagc actgtgttcc   2460
tgttgtcgtg gttcaagacc caccaggtat tttcagatta taaaacttttt ctttctttct   2520
taacagtttc aacaggccac tcactcttaa gggtgagaag aataaccaca attgtatgtg   2580
cctgtttttt actcttagca ttagatgaat tcaaatttgg aaacagattg atagcaattt   2640
ttttctaaaa cattagactt ttgttaacct tttttaaattt gcttcaacaa                2700
gctctccacc agttgacttt cttttggctaa ttttactttg catgatatgc cttaatatgc    2760
cttcataaat aaccatttta agtcataatt tgtccttaag ctgcttttttt cttctattaa   2820
ttggatcata gtaaagagta gtcaataggg tcttcagcta ttaattgtag aggtgattaa    2880
aaccaacaag gagtttcatg tgcaaggag ataaggaatg aatataaaga ttgctatttg     2940
ggtggctctt attaaactgt gtattttgta cttatcacta cacgtatccc ccaaatgctt    3000
acatgggagt ttgaggttag tattttcact tccttggtgt tagtactcta ttcacattct    3060
tattgtaacc ttcctcattt cacagataag gaatctttgg ggattaacca acctcctttc    3120
tgtaatggta atcattaaaa taagtccttat tgataaaggt cagatggagc cctagagtgt    3180
attactgcat ctatttttt ccccgagaag ataaggacc ttcagggatg gcttaagtgt      3240
atctgtccag atgaaggatg gtcacatga cctcttggct tcccaagtct aagctctgta    3300
actttgcacc agtgtgtgca tatatgtgca aggccctttca agtggtctga aaccgtggct   3360
ctaaaaacca cagctggtgg agaggaggac agacacactt gccaccttgc ctacctaatt   3420
gccatctaaa atgggccgaa cagtggattt cacaatagag ttttcacccct ttagattttac   3480
aacctgtcag gtgaaactg aagtgaaaac tgctgcacac agcaattcag ggagcaaaaa    3540
atgtgctgag gagactgttt acctaaaggt tgttcttggt gctattcctt gtcaaaatgt    3600
gaacacacac aaatgaggtt tgtgcattgt catccgtggg tccattga gccagtaacc      3660
cccagtggtc tcatggtgct cttcgctcca gtttggggaa tgctggattc tttcagcccc    3720
tgcagccctc caggtcaaaa tgacactttg tcactgagtt ttctacacag ctctattagt    3780
aactgacagc acacgcttc aagggaactt caagggaaac atggaataaa ctaagtctca     3840
attgcc                                                                 3846
```

| SEQ ID NO: 17 | moltype = DNA length = 2637 |
|---|---|
| FEATURE | Location/Qualifiers |
| source | 1..2637 |
| | mol_type = genomic DNA |
| | organism = Homo sapiens |

```
SEQUENCE: 17
agataaagac aggaacatgg tgtttataag ctgcccttaa tggcagagaa cacagacaga    60
aacgagggaa gagagagaaa ttggggaccc tgaagaaagg gggccagcag caggtaggtg   120
ccatcaggga caagaacagc acctcccagg gtgggagacc ccaggccttt ctggcagcag   180
gtctggatgg aaagtggaca ggaggctcac ccgtctgcat cccctgctcc tgccccctgct  240
cggctacaaa aaccaaaggg acagcagctg accacacccc ggtagccact cctgcataaa   300
gctctcccct cctgtgacca gctgaggacc tcaggctgca gcggagccat gcccagatac   360
acggtgcacg tacgtgggga atggctggca gtgccctgcc aggacgcgca gctcactgtg   420
ggctggctgg gccgggaggc cgtgaggcgc tatatcaaga ataagcccga caatggtggc   480
ttcacctccg tggatgacgc gcacttcctt gtgcgccggt gcaagggcct gggcctgctg   540
gacaacgagg accggctcga ggtggcccta gagaacaacg agttcgtgga agtggttata   600
gagggtgatg ccatgtctcc tgacttcatt ccatctcaac cagaaggagt ttatctatac   660
agcaagtacc gggagcctga aaagtacatc gagttagatg gagaccgtct gaccacggag   720
gatctggtca acttgggaaa gggacgctac aaaataaagc tcaccccaac agctgagaag   780
agggtgcaga aatccaggga ggtcatagat agcatcataa aagagaaaac agttgtttac   840
ggtattacta caggttttgg gaaatttgcc agaactgtaa ttcctatcaa taagctacag   900
gagcttcagg tcaacttagt acgctcacat tcttcaggtg ttgggaaacc actaagtcct   960
gagaggtgtc ggatgctctt ggctttaagg atcaatgtct tagccaaagg atacagtggc  1020
atttccctgg agaccctcaa acaagtcata gaaatgttta atgcctcctg cctgccctat  1080
gtcccagaga aaggaaccgt tggtgccagt ggagaccttg ccccactctc tcatcttgct  1140
cttgggctag ttgagaagg gaagatgtgg tctccgaaga gtggctgggc tgatgctaaa   1200
tacgtgctag aagcccatgg attgaaacca gttattttaa aaccaaaaga gggcctggca  1260
ctcatcaatg ggacgcagat gatcacatcc ctgggctgtg aagctgtaga gcgagccagt  1320
gctattgcac ggcaggctga cattgtggca gccctgaccc ttgaggtgct gaagggcacc  1380
accaaagcct ttgacactga cattcatgct cttcgacctc accgtgggca aattgaagtt  1440
gcttttcggt ttcggtcact cttggactca gatcaccacc catcagaaat agcagagagt  1500
cacaggttct gtgatcgcgt ccaggatgca tacaccttgc gctgctgtcc acaggtccat  1560
ggtgtggtga atgatacaat agcatttgtg aagaacatca ttaccacaga actgaacagc  1620
gcaacgatata atcctatggt ctttgccaat aggggagaga cagtttctgg aggaaacttc  1680
catggtgaat acccagccaa agccctagac tacttgccaa ttggcatcca tgaacttgct  1740
gcaatcagtg agagaagaat cgagcggctc tgcaatccct ccctcagtga gctgcctgcc  1800
ttcctggtgg ctgaaggtgg tctgaactct gggttcatga tagctcactg cacggcagca  1860
gcccttgttt ctgagaacaa ggctctgtgc catccctcgt ctgttgactc cctctccacc  1920
agcgcagcca cggaggacca cgtctccatg ggaggatggg cagcaaggaa agccctcagg  1980
gtcatcgagc atgtggagca aagtgctggc atcgagctcc ttgcagcctg ccagggcata  2040
gagtttctac gtcccctgaa aacaaccact ccgctggaga aggtctatga cctggtgcgc  2100
tctgttgtaa ggtttgggaa gtagctgctc catacattga aaaatacaga atggagcata  2160
ttccagaatc aagacctctt tctccaacag ccttttcact gcaattctg cacaagaaat   2220
ccaccaaaat cccggagtct gaggaccttt aatgggcttt gtcatgaagt agcagatgag   2280
agggcagtca gtttagcaca aagcaatact aggctgaagg agagacctga gaactttcct  2340
aggtagatca atccattgta tcattcagtt cttctaaagc ctacgttggt taggctgatg  2400
gcagtattat agttgctaaa ttcagcactg tgttcctgtt gtcgtggttc aagacccacc  2460
aggtattttc agattataaa acttttcttt cttttcttaac agtttcaaca ggccactcac  2520
tcttaagggt gagaagaata accacaattg tatgtgcctg ttttttactc ttagcattag  2580
atgaattcaa atttggaaac agattgatag caattttttc taaaaacatt agactttt   2637

SEQ ID NO: 18        moltype = DNA   length = 3822
FEATURE              Location/Qualifiers
source               1..3822
                     mol_type = genomic DNA
                     organism = Homo sapiens
SEQUENCE: 18
agataaagac aggaacatgg tgtttataag ctgcccttaa tggcagagaa cacagacaga    60
aacgagggaa gagagagaaa ttggggaccc tgaagaaagg gggccagcag caggtaggtg   120
ccatcaggga caagaacagc acctcccagg gtgggagacc ccaggccttt ctggcagcag   180
gtctggatgg aaagtggaca ggaggctcac ccgtctgcat cccctgctcc tgccccctgct  240
cggctacaaa aaccaaaggg acagcagctg accacacccc ggtagccact cctgcataaa   300
gctctcccct cctgtgacca gctgaggacc tcaggctgca gcggagccat gcccagatac   360
acggtgcacg tacgtgggga atggctggca gtgccctgcc aggacgcgca gctcactgtg   420
ggctggctgg gccgggaggc cgtgaggcgc tatatcaaga ataagcccga caatggtggc   480
ttcacctccg tggatgacgc gcacttcctt gtgcgccggt gcaagggcct gggcctgctg   540
gacaacgagg accggctcga ggtggcccta gagaacaacg agttcgtgga agtggttata   600
gagggtgatg ccatgtctcc tgacttcatt ccatctcaac cagaaggagt ttatctatac   660
agcaagtacc gggagcctga aaagtacatc gagttagatg gagaccgtct gaccacggag   720
gatctggtca acttgggaaa gggacgctac aaaataaagc tcaccccaac agctgagaag   780
agggtgcaga aatccaggga ggtcatagat agcatcataa aagagaaaac agttgtttac   840
ggtattacta caggttttgg gaaatttgcc agaactgtaa ttcctatcaa taagctacag   900
gagcttcagg tcaacttagt acgctcacat tcttcaggtg ttgggaaacc actaagtcct   960
gagaggtgtc ggatgctctt ggctttaagg atcaatgtct tagccaaagg atacagtggc  1020
atttccctgg agaccctcaa acaagtcata gaaatgttta atgcctcctg cctgccctat  1080
gtcccagaga aaggaaccgt tggtgccagt ggagaccttg ccccactctc tcatcttgct  1140
cttgggctag ttgagaagg gaagatgtgg tctccgaaga gtggctgggc tgatgctaaa   1200
tacgtgctag aagcccatgg attgaaacca gttattttaa aaccaaaaga gggcctggca  1260
ctcatcaatg ggacgcagat gatcacatcc ctgggctgtg aagctgtaga gcgagccagt  1320
gctattgcac ggcaggctga cattgtggca gccctgaccc ttgaggtgct gaagggcacc  1380
accaaagcct ttgacactga cattcatgct cttcgacctc accgtgggca aattgaagtt  1440
gcttttcggt ttcggtcact cttggactca gatcaccacc catcagaaat agcagagagt  1500
cacaggttct gtgatcgcgt ccaggatgca tacaccttgc gctgctgtcc acaggtccat  1560
ggtgtggtga atgatacaat agcatttgtg aagaacatca ttaccacaga actgaacagc  1620
```

```
gcaacagata atcctatggt cttgccaat aggggagaga cagttctgg aggaaacttc   1680
catggtgaat acccagccaa agccctagac tacttggcca ttggcatcca tgaacttgct   1740
gcaatcagtg agagaagaat cgagcggctc tgcaatccct ccctcagtga gctgcctgcc   1800
ttcctggtgt ctgaaggtgg tctgaactct gggttcatga tagctcactg cacggcagca   1860
gcccttgttt ctgagaacaa ggctctgtgc catccctcgt ctgttgactc cctctccacc   1920
agcgcagcca cggaggacca cgtctccatg ggaggatggg cagcaaggaa agccctcagg   1980
gtcatcgagc atgtggagca agtgctggcc atcgagctcc ttgcagcctg ccagggcata   2040
gagtttctac gtcccctgaa aacaaccact ccgctggaga aggtctatga cctggtgcgc   2100
tctgttgtaa ggtttgggaa gtagctgctc catacattga aaaatacaga atggagcata   2160
ttccagaatc aagacctctt tctccaacag ccttttcact gcaatttctg cacaagaaat   2220
ccaccaaaat cccggagtct gaggaccttt aatgggcttt gtcatgaagt agcagatgag   2280
agggcagtca gtttagcaca aagcaatact aggctgaagg agagacctga gaactttcct   2340
aggtagatca atccattgta tcattcagtt cttctaaagc ctacgttggt taggctgatg   2400
gcagtattat agttgctaaa ttcagcactg tgttcctgtt gtcgtggttc aagacccacc   2460
aggtatttc agattataaa acttttcttt ctttcttaac agtttcaaca ggccactcac   2520
tcttaagggt gagaagaata accacaattg tatgtgcctg tttttttactc ttagcattag   2580
atgaattcaa atttggaaac agattgatag caattttttc taaaaacatt agacttttgt   2640
taacctttt ttttttttt aaattgctt caacaagctc tccaccagtt gactttcttt   2700
ggctaatttt actttgcatg atatgcctta atatgcctc ataataaacc attttaagtc   2760
ataattgtc cttaagctgc ttttttcttc tattaattgg atcatagtaa agagtagtca   2820
ataggtctt cagctattaa ttgtagaggt gattaaaacc aacaaggagt tcatgtgca   2880
aaggagataa ggaatgaata taagattgc tatttgggtg gctcttatta aactgtgtat   2940
tttgtactta tcactacacg tatccccaa atgcttacat gggagttga ggttagtatt   3000
ttcacttcct tggtgttagt actctattca cattcttatt gtaaccttcc tcatttcaca   3060
gataaggaat ctttggggat taaccaacct cctttctgta atggtaatca ttaaaataag   3120
tcctattgat aaaggtcaga tggagcccta gagtgtatta ctgcatctat tttttttccc   3180
gagaagataa aggaccttca gggatggctt aagtgtatct gtccagatga aggatgggtc   3240
acatgacctc ttggcttccc aagtctaagc tctgtgactt tgcaccagtg tgtgcatata   3300
tgtgcaaggc ccttcaagtg gtctgaaacc gtggctctaa aaccacagc tggtggagag   3360
gaggacagac acacttgcca ccttgcctac ctaattgcca tctaaaatgg gccgaacagt   3420
ggatttcaca atagagtttt caccctttag atttacaacc tgtcaggtgg aaactgaagt   3480
gaaaactgct gcacacagca attcaggag caaaaaatgt gctgaggaga ctgtttacct   3540
aaaggttgtt cttggtgcta ttccttgtca aaatgtgaac acacacaaat gaggtttgtg   3600
cattgtcatc cgtgggctgc cattgagcca gtaaccccca gtggtctcat ggtgctcttc   3660
gctccagttt ggggaatgct ggattctttc agcccctgca gccctccagg tcaaaatgac   3720
actttgtcac tgagtttctt acacagctct attagtaact gacagcacac gccttcaagg   3780
gaacttcaag ggaaacatgg aataaactaa gtctcaattg cc                     3822

SEQ ID NO: 19         moltype = DNA    length = 3825
FEATURE               Location/Qualifiers
source                1..3825
                      mol_type = genomic DNA
                      organism = Homo sapiens
SEQUENCE: 19
agataaagac aggaacatgg tgtttataag ctgcccttaa tggcagagaa cacagacaga   60
aacgagggaa gagagagaaa ttggggaccc tgaaagaagg gggccagcag caggtaggtg   120
ccatcaggga caagaacagc acctcccagg gtgggagaca ccaggccttt ctggcagcag   180
gtctggatgg aaagtggaca ggaggctcac ccgtctgcat cccctgctcc tgcccctgct   240
cggctacaaa aaccaagggg acagcagctg accacacccc ggtagccact cctgcataaa   300
gctctccct cctgtgacca gctgaggacc tcaggctgca gcggagccat gcccagatac   360
acggtgcacg tacgtgggga atggctggca gtgccctgcc aggacgcgca gtcactgtg   420
ggctggctgg gccgggaggc cgtgaggcgc tatatcaaga ataagcccga caatggtggc   480
ttcacctccg tggatgacgc gcacttcctt gtgcgccggt gcaagggcct gggcctgctg   540
gacaacgagg accggctcga ggtggcccta gagaacaacg agttcgtgga agtggttata   600
gagggtgatg ccatgtctcc tgacttcatt ccatctcaac cagaaggagt ttatctatac   660
agcaagtacc gggagcctga aaagtacatc gagttagatg agaccgtct gaccacggag   720
gatctggtca acttgggaaa gggacgctac aaaaataaagc tcaccccaac agctgagaag   780
aggggtgcaga aatccaggga ggtcatagat agcatcataa aagagaaaac agggagcttc   840
aggtcaactt agtacgctca cattcttcag gtgttgggaa accactaagt cctgagaggt   900
gtcggatgct cttggcttta aggatcaatg tcttagccaa aggatacagt ggcatttcc   960
tggagaccct caaacaagtc atagaaatgt ttaatgcctc ctgcctgccc tatgtcccag  1020
agaaaggaac cgttggtgcc agtggagacc ttgccccact ctctcatctt gctcttgggc  1080
tagttggaga agggaagatg tggtctccga agagtggctg ggctgatgct aaatacgtgc  1140
tagaagccca tggattgaaa ccagttattt taaaaccaaa agagggcctg gcactcatca  1200
atgggacgca gatgatcaca tccctgggct gtgaagctgt agagcgagcc agtgctattg  1260
cacggcaggc tgcatttgtg gcagccctga cccttgaggt gctgaagggc accaccaaag  1320
cctttgacac tgacattcat gctcttcgac ctcaccgtgg gcaaattgaa gttgcttttc  1380
ggtttcggtc actcttggac tcagatcacc acccatcaga aatagcagag agtcacaggt  1440
tctgtgatcg cgtccaggat cgatacacct tgcgctgctg tccacagtgc catgtgtgg  1500
tgaatgatac aatagcatt tgtgaagaaca tcattaccac agaactgaac agcgcaacag  1560
ataatcctat ggtcttgcc aatagggag agacagttc tggaggaaac ttccatggtg  1620
aatacccagc caaagcccta gactacttgg ccattggcat ccatgaactt gctgcaatca  1680
gtgagagaag aatcgagcgg ctctgcaatc cctccctcag tgagctgcct gccttcctgg  1740
tggctcagg tggtctgaac tctgggttca tgatagcctc ctgcacgcgca gcagcccttg  1800
tttctgagaa caaggctctg tgccatccct cgtctgttga ctccctctcc accagcgcag  1860
ccacggagga ccacgtctcc atgggaggat gggcagcaag gaaagccctc agggtcatcg  1920
agcatgtgga gcaagtgctg gccatcgagc tccttgcagc ctgccagggc atagagtttc  1980
tacgtcccct gaaaacaacc actccgctgg agaaggtcta tgacctggtg cgctctgttg  2040
taaggcctg gataaaagat cgcttcatgg ccccggacat cgaggcagcc cacaggctgc  2100
```

```
tcctggagca gaaggtttgg gaagtagctg ctccatacat tgaaaaatac agaatggagc  2160
atattccaga atcaagacct ctttctccaa cagccttttc actgcaattt ctgcacaaga  2220
aatccaccaa aatcccggag tctgaggacc tttaatgggc tttgtcatga agtagcagat  2280
gagagggcag tcagtttagc acaaagcaat actaggctga aggagagacc tgagaacttt  2340
cctaggtaga tcaatccatt gtatcattca gttcttctaa agcctacgtt ggttaggctg  2400
atggcagtat tatagttgct aaattcagca ctgtgttcct gttgtcgtgg ttcaagaccc  2460
accaggtatt ttcagattat aaaacttttc tttctttctt aacagtttca acaggccact  2520
cactcttaag ggtgagaaga ataaccacaa ttgtatgtgc ctgttttta ctcttagcat  2580
tagatgaatt caaatttgga aacagattga tagcaatttt ttctaaaaac attagacttt  2640
tgttaacctt ttttttttt tttaaatttg cttcaacaag ctctccacca gttgactttc  2700
tttggctaat tttactttgc atgatatgcc ttaatatgcc ttcataaata accattttaa  2760
gtcataattt gtccttaagc tgcttttttc ttctattaat tggatcatag taaagagtag  2820
tcaatagggt cttcagctat taattgtaga ggtgattaaa accaacaagg agtttcatgt  2880
gcaaaggaga taaggaatga atataaagat tgctatttgg gtggctctta ttaaactgtg  2940
tattttgtac ttatcactac acgtatcccc caaatgctta catgggagtt tgaggttagt  3000
attttcactt ccttggtgtt agtactctat tcacattctt attgtaacct tcctcatttc  3060
acagataagg aatctttggg gattaaccaa cctcctttct gtaatggtaa tcattaaaat  3120
aagtcctatt gataaaggtc agatggagcc ctagagtgta ttactgcatc tattttttc  3180
cccgagaaga taaggaccct tcagggatgg cttaagtgta tctgtccaga tgaaggatgg  3240
gtcacatgac ctcttggctt cccaagtcta agctctgtga ctttgcacca gtgtgtgcat  3300
atatgtgcaa ggcccttcaa gtggtctgaa accgtggctc taaaaccac agctggtgga  3360
gaggaggaca gacacacttg ccaccttgcc tacctaaatg ccatctaaaa tgggccgaac  3420
agtggatttc acaatagagt tttcacccct tagatttaca acctgtcagg tggaaactga  3480
agtgaaaact gctgcacaca gcaattcagg gagcaaaaaa tgtgctgagg agactgttta  3540
cctaaaggtt gttcttggtg ctattccttg tcaaaatgtg aacacacaca aatgaggttt  3600
gtgcattgtc atccgtgggc tgccattgag ccagtaaccc ccagtggtct catggtgctc  3660
ttcgctccag tttggggaat gctggattct ttcagcccct gcagccctcc aggtcaaaat  3720
gacactttgt cactgagttt tctacacagc tctattagta actgacagca cacgccttca  3780
agggaacttg aagggaaaca tggaataaac taagtctcaa ttgcc           3825

SEQ ID NO: 20         moltype = DNA  length = 3085
FEATURE               Location/Qualifiers
source                1..3085
                      mol_type = genomic DNA
                      organism = Homo sapiens
SEQUENCE: 20
agcagcaggt aggtgccatc agggacaaga acagcacctc ccagggtggg agaccccagg    60
cctttctggc agcaggtctg gatggaaagt ggacaggagg ctcacccgtc tgcatcccct   120
gctcctgccc ctgctcggct acaaaaacca aagggacagc agctgaccac acccccggtag  180
ccactcctgc ataaagctct ccccctcctgt gaccagctca ggacctcagg ctgccagcgga  240
gccatgccca gatacacggt gcacgtacgt ggggaatggc tggcagtgcc ctgccaggac   300
gcgcagctca ctgtgggctg gctgggccgg gaggccgtga ggcgctatat caagaataag   360
cccgacaatg gtggcttcac ctccgtggat gacgcgcact cttgtgcc ccggtgcaag   420
ggcctgggcc tgctggacaa cgaggaccgg ctcgaggtgg ccctagagaa caacgagttc   480
gtggaagtgg ttatagaggg tgatgccatg tctcctgact tcattccatc tcaaccagaa   540
ggagtttatc tatacagcaa gtaccgggag cctgaaaagt acatcgagtt agatgggagac  600
cgtctgacca cggaggatct ggtcaacttg ggaaaggaac gctacaaaat aaagctcacc   660
ccaacagctg agaagagggt gcagaaatcc agggaggtca tagatagcat cataaaaagg  720
aaaacagttg tttacggtat tactacaggt tttgggaaat ttgccagaac tgtaattcct   780
atcaataagc tacaggagct tcaggtcaac ttagtacgct cacattcttc aggtgtttggg  840
aaaccactaa gtcctgagag tgtgtcggatg ctcttgctta taaggatcaa tgtcttaagc   900
aaaggataca gtggcatttc cctggagacc ctcaaacaag tcatagaaat gtttaatgcc   960
tcctgcctgc cctatgtccc agagaaagga accgttggtg ccagtggaga ccttgcccca  1020
ctctctcatc ttgctcttgg gctagttgga aagggaaga tgtggtctcc gaagagtggc  1080
tgggctgatg ctaaatacgt gctagaagcc catggattga aaccagttat ttttaaaacca  1140
aaagagggcc tggcactcat caatgggacg cagatgatca catccctggg ctgtgaagct  1200
gtagagcgag ccagtgctat tgcacggcag gctgacattg tggcagccct gacccttgag  1260
gtgctgaagg gcaccaccaa agcctttgac actgacattc atgctcttcg acctcaccgt  1320
gggccaaattg aagttgcttt tcggtttcgg tcactcttgg actcagatca ccacccatca  1380
gaaatagcag agagtcacag gttctgtgat cgcgtccagg atgcatacac cttgcgctgc  1440
tgtccacagg tccatggtgt ggtgaatgat acaatagcat ttgtgaagaa catcattacc  1500
acagaactga acagcgcaac agataatcct atggtctttg ccaatagggg agagacagtt  1560
tctgaggaa acttccatgg tgaatacccca gccaagccc tagactactt ggccattggc   1620
atccataac ttgctgcaat cagtgagaga agaatccggac tgtctcgaca tccctccctc   1680
agtgagctgc ctgccttcct ggtggctgaa ggtggtctga actctgggtt catgatagct   1740
cactgcacgg cagcagccct tgtttctgag aacaaggctc tgtgccatcc ctcgtctgtt   1800
gactccctct ccaccagcgc agccacggag gaccacgtct ccatgggagg atgggcagca  1860
aggaaagccc tcagggtcat cgagctgtg gagcaagtgc tggccatcga gctccttgcg  1920
gcctgccagg gcatagagtt tctacgtccc ctgaaaacaa ccactccgct gggagaaggtc 1980
tatgacctgg tgcgctctgt tgtaaggccc tggataaaag atcgcttcat ggccccggac  2040
atcgaggcag cccacaggct gctcctggag cagaaggttt gggaagtagc tgtctccatac 2100
attgaaaaat acagaatgga gcatattcca gaatcaagac ctctttctcc aacagccttt  2160
tcactgcaat ttctgcacaa gaaatccacc aaaatcccgg agtctgagga cctttaatgg  2220
gctttgtcat gaagtagcag atgagagggc agtcagttta gcacaaagca atactaggct  2280
gaaggagaga cctgagaact ttcctaggta gatcaatcca ttgtatcatt cagttcttct  2340
aaagcctacg ttggttaggc tgatggcagt attatagttg ctaaattcag cactgtgttc  2400
ctgttgtcgt ggttcaagac cccaccaggta ttttcagatt ataaaacttt tctttctttc  2460
ttaacagttt caacaggcca ctcactctta agggtgagaa gaataaccac aattgtatgt  2520
gcctgttttt tactcttagc attagatgaa ttcaaatttg gaaacagatt gatagcaatt  2580
```

```
tttttctaaaa acattagact tttgttaacc tttttttttt tttttaaatt tgcttcaaca   2640
agctctccac cagttgactt tctttggcta attttacttt gcatgatatg ccttaatatg   2700
ccttcataaa taaccatttt aagtcataat ttgtccttaa gctgctttttt tcttctatta   2760
attggatcat agtaaagagt agtcaatagg gtcttcagct attaattgta gaggtgatta   2820
aaaccaacaa ggagtttcat gtgcaaagga gataaggaat gaatataaag attgctattt   2880
gggtggctct tattaaactg tgtattttgt acttatcact acacgtatcc cccaaatgct   2940
tacatgggag tttgaggtta gtattttcac ttccttggtg ttagtactct attcacattc   3000
ttattgtaac cttcctcatt tcacagataa ggaatctttg gggattaacc aacctccttt   3060
ctgtaatggt aatcattaaa ataag                                         3085
```

```
SEQ ID NO: 21            moltype = DNA   length = 2804
FEATURE                  Location/Qualifiers
source                   1..2804
                         mol_type = genomic DNA
                         organism = Homo sapiens
SEQUENCE: 21
agacagaaac gagggaagag agagaaattg gggaccctga agaaggggg ccagcagcag    60
gtaggtgcca tcagggacaa gaacagcacc tcccagggtg ggagaccccca ggcctttctg   120
gcagcaggtc tggatggaaa gtggacagga ggctcacccg tctgcatccc ctgctcctgc   180
ccctgctcgg ctacaaaaac caaagggaca gcagctgacc acaccccggt agccactcct   240
gcataaagct ctcccctcct gtgaccagct gaggacctca ggctgcagcg gagccatgcc   300
cagatacacg gtgcacgtac gtggggaatg gctggcagtg ccctgccagg acgcgcagct   360
cactgtgggc tggctgggcc gggaggccgt gaggcgctat atcaagaata agcccgacaa   420
tggtggcttc acctccgtgg atgacgcgca cttccttgtg cgccggtgca agggcctggg   480
cctgctggac aacgaggacc ggctcgaggt ggccctagaa acaacgagt tcgtggaagt   540
ggttatagag ggtgatgcca tgtctcctga cttcattcca tctcaaccag aaggagttta   600
tctatacagc aagtaccggg agcctgaaaa gtacatcgag ttagatggag accgtctgac   660
cacgaggat ctggtcaact tgggaaaggg acgctacaaa ataaagctca cccaacagc    720
tgagaagagg gtgcagaaat ccaggaggt catagatagc atcataaaag agaaacagg    780
gagcttcagg tcaacttagt acgctcacat tcttcagtg ttgggaaacc actaagtcct   840
gagaggtgtc ggatgctctt ggctttaagg atcaatgtct tagccaaagg atacagtggc   900
atttccctgg agaccctcaa acaagtcata gaaatgttta atgcctcctg cctgccctat   960
gtcccagaga aggaaccgt tggtgccagt ggagaccttg ccccactctc tcatcttgct  1020
cttgggctag ttggagaagg gaagatgtgg tctccgaaga gtggctgggc tgatgctaaa  1080
tacgtgctag aagcccatgg attgaaacca gttattttaa aaccaaaaga gggcctggca  1140
ctcatcaatg ggacgcagat gatcacatcc ctgggctgtg aagctgtaga gcgagccagt  1200
gctattgcac ggcaggctga cattgtggca gccctgaccc ttgaggtgct gaagggcacc  1260
accaaagcct ttgacactga cattcatgct cttcgacctc accgtgggca aattgaagtt  1320
gcttttcggt ttcggtcact cttggactca gatcaccacc catcagaaat agcagagagt  1380
cacaggttct gtgatcgcgt ccaggatgca tacaccttgc gctgctgtcc acaggtccat  1440
ggtgtggtga atgatacaat agcatttgtg aagaacatca ttaccacaga actgaacagc  1500
gcaacagata atcctatggt ctttgccaat aggggagaga caatttctgg aggaaacttc  1560
catggtgaat acccagccaa agccctagac tacttgccag ttggcatcca tgaacttgct  1620
gcaatcagtg agagaagaat cgagcggctc tgcaatccct ccctcagtga gctgcctgcc  1680
ttcctggtgg ctgaaggtgg tctgaactct gggttcatga tagctcactg cacggcagca  1740
gcccttgttt ctgagaacaa ggctctgtgc catccctcgt ctgttgactc cctctccacc  1800
agcgcggcca cggaggacca cgtctccatg ggaggatggg cagcaaggaa agccctcagg  1860
gtcatcgagc atatggagca agtgctggcc atcgagtcc ttgcagcctg cagggcata   1920
gagtttctac gtcccctgaa aacaaccact ccgctggaga aggtctatga cctggtgcgc  1980
tctgttgtaa ggccctggat aaaagatcgc ttcatggccc cggacatcga ggcagcccac  2040
aggctgctcc tggagcagaa ggtttggaa gtagctgctc catacattga aaatacagga  2100
atggagcata ttccagaatc aagaccctctt tctccaacag ccttttcact gcaatttctg  2160
cacaagaaat ccaccaaaat cccggagtct gaggacccttt aatgggcttt gtcatgaagt  2220
agcagatgag agggcagtca gtttagcaca aagcaatact aggctgaagg agagacctga  2280
gaacttcct aggtagatca tccattgta tcattcagtt cttctaaagc ctacgttggt   2340
taggctgatg gcagtattat agttgctaaa ttcagcactg tgttcctgtt gtcgtggttc  2400
aagacccacc aggtatttct agattataaa acttttcttt cttcttaac agtttcaaca   2460
ggccactcac tcttaagggt gagaagaata accacaattg tatgtgcctg tttttttactc  2520
ttagcattag atgaatttcaa atttggaaac agattgatag caatttttttc taaaaacatt  2580
agactttttgt taacctttttt ttttttttttt aaatttgctt caacaagctc tccaccagtt  2640
gactttcttt ggctaatttt actttgcatg atatgcctta atatgccttc ataaataacc   2700
atttaagtc ataatttgtc cttaagctgc ttttttcttc tattaattgg atcatagtaa   2760
agagtagtca atagggtctt cagctattaa ttgtagaggt gatt                   2804
```

```
SEQ ID NO: 22            moltype = DNA   length = 1474
FEATURE                  Location/Qualifiers
source                   1..1474
                         mol_type = genomic DNA
                         organism = Homo sapiens
SEQUENCE: 22
gagtaatctc agataaagac aggaacatgg tgtttataag ctgcccttaa tggcagagaa    60
cacagacaga aacgagggaa gagagagaaa ttggggaccc tgaagaaagg gggccagcag   120
caggtaggtg ccatcaggga caagaacagc acctcccagg gtgggagacc ccaggccttt   180
ctggcagcag gtctggatgg aaagtggaca ggaggctcac ccgtctgcat cccctgctcc   240
tgccccctgct cgcctacaaa aaccaaaggg acagcagctg accacacccc ggtagcact   300
cctgcataaa gctctcccct cctgtgacca gctgaggacc tcaggctgca gcggagccat   360
gcccagatac acggtgcacg tacgtgggga atggctggag gaaacttcca tggtgaatac   420
ccagccaaag ccctagacta cttggccatt ggcatccatg aacttgctgc aatcagtgag   480
agaagaatcg agcggctctg caatccctcc ctcagtgagc tgcctgcctt cctggtggct   540
```

```
gaaggtggtc tgaactctgg gttcatgata gctcactgca cggcagcagc ccttgtttct    600
gagaacaagg ctctgtgcca tccctcgtct gttgactccc tctccaccag cgcagccacg    660
gaggaccacg tctccatggg aggatgggca gcaaggaaag ccctcagggt catcgagcat    720
gtggagcaag tgctggccat cgagctcctt gcagcctgcc agggcataga gtttctacgt    780
cccctgaaaa caaccactcc gctggagaag gtctatgacc tggtcgcgtc tgttgtaagg    840
ccctggataa aagatcgctt catggccccg gacatcgagg cagcccacag gctgctcctg    900
gagcagaagg tttgggaagt agctgctcca tacattgaaa aatacagaat ggagcatatt    960
ccagaatcaa gacctctttc tccaacagcc ttttcactgc aatttctgca caagaaatcc   1020
accaaaatcc cggagtctga ggacctttaa tgggctttgt catgaagtag cagatgagag   1080
ggcagtcagt ttagcacaaa gcaatactag gctgaaggag agacctcgaga actttcctag   1140
gtagatcaat ccattgtata attcagttct tctaaagcct acgttggtta ggccgatggc   1200
agtattatag ttgctaaatt cagcactgtg ttcctgttgt cgtggttcaa gacccaccag   1260
gtattttcag attataaaac ttttctttct ttcttaacag tttcaacagg ccactcactc   1320
ttaagggtga gaagaataac cacaattgta tgtgcctgtt ttttactctt agcattagac   1380
gaattcaaat ttggaaacag attgatagca atttttttcta aaaacattag acttttgtta   1440
acctttttt tttttttttt tttaaatttg cttc                                1474

SEQ ID NO: 23          moltype = DNA    length = 2271
FEATURE                Location/Qualifiers
source                 1..2271
                       mol_type = genomic DNA
                       organism = Homo sapiens
SEQUENCE: 23
gccatcaggg acaagaacag cacctcccag ggtgggagac cccaggcctt tctggcagca    60
ggtctggatg gaaagtggac aggaggctca cccgtctgca tcccctgctc ctgcccctgc   120
tcggctacaa aaaccaaagg gacagcagct gaccacacca cggtagccac tcctgcataa   180
agctctcccc tcctgtgacc agctgaggac ctcaggctgc agcggagcca tgcccagata   240
cacggtgcac gtacgtgggg aatggctggc agtgccctgc caggacgcgc agctcactgt   300
gggctggctg gccggagg ccgtgaggcg ctatatcaag aataagcccg acaatggtgg    360
cttcacctcc gtggatgacg cgcacttcct tgtgcgccgg tgcaagggcc tgggcctgct   420
ggacaacgag gaccggctcg aggtggccct agagaacaag gagttcgtgg aagtggttat   480
agagggtgat gccatgtctc ctgacttcat tccatctcaa ccagaaggag tttatctata   540
cagcaagtac cgggagcctg aaaagtacat cgagttagat ggagaccgtc tgaccacgga   600
ggatctggtc aacttgggaa agggacgcta caaaataaag ctcaccccaa cagctgagaa   660
gagggtgcag aaatccaggg aggtcataga tagcatcata aaagagaaaa cagggagctt   720
caggtcaact tagtacgctc acattcttca ggtgttggga aaccactaag tcctgagagg   780
tgtcggatgc tcttggcttt aaggatcaat gtcttagcca aaggatacag tggcatttcc   840
ctggagaccc tcaaacaagt catagaaatg tttaatgcct cctgcctgcc ctatgtccca   900
gagaaaggaa ccgttggtgc cagtggagac cttgccccgc tctctcatct tgctcttggg   960
ctagttggag aagggaagat gtggtctccg aagagtggcc gggctgatgc taaatacgtg   1020
ctagaagccc atggattgaa accagttatt ttaaaaccaa aagagggcct ggcactcatc   1080
aatgggacgc agatgatcac atccctgggc tgtgaagctg tagagcgagc cagtgctatt   1140
gcacggcagg ctgacattgt ggcagccctg acccttgagg tgctgaaggg caccaccaaa   1200
gcctttgaca ctgacattca tgctcttcga cctcaccgtg ggcaaattga agttgctttt   1260
cggtttcggt cactcttgga ctcagatcac cacccatcag aaatagcaga gagtcacagg   1320
ttctgtgatc gcgtccagga tgcatacacc ttgcgctgct gtccacaggt ccatggtgtg   1380
gtgaatgaca caatagcatt tgtgaagaac atcattacca cagaactgaa cagcgcaaca   1440
gataatccta tggtctttgc caataggggga gagacaattt ctggaggaaa cttccatgcc   1500
cctagactac ttggccattg gcatccatga acttgctgca atcagtgaga aagaatcga   1560
gcggctctgc aatccctccc tcagtgagct gcctgccttc ctggtggctg aaggtggtct   1620
gaactctggg ttcatgatag ctcactgcac ggcagcagcc cttgtttctg agaacaaggc   1680
tctgtgccat ccctcgtctg ttgactccct ctccaccagc gcagccacgg aggaccacgt   1740
ctccatggga ggatgggcag caaggaaagc cctcagggtc atcgagcatg tggagcaagt   1800
gctggccatc gagctccttg cagcctgcca gggcataga tttctacgtc ccctgaaaac   1860
aaccactccg ctggagaagg tctatgacct ggtcgctct gttgtaaggc cctggataaa   1920
agatcgcttc atggccccgg acatcgagg agcccacagg ctgctcctgg agcagaaggt   1980
ttgggaagta gctgctccat acattgaaaa atacagaatg gagcatattc agaatcaag   2040
acctcttttct ccaacagcct tttcactgca atttctgcac aagaaatcca ccaaaatccc   2100
ggagtctgag gaccttaat gggctttgtc atgaagtagc agatgagagg gcagtcagtt   2160
tagcacaaag caatactagg ctgaaggaga gacctgagaa ctttcctagg tagatcaatc   2220
cattgtatca ttcagttctt ctaaagccta cgttggttag gctgatggca g             2271

SEQ ID NO: 24          moltype = DNA    length = 2355
FEATURE                Location/Qualifiers
source                 1..2355
                       mol_type = genomic DNA
                       organism = Homo sapiens
SEQUENCE: 24
gccatcaggg acaagaacag cacctcccag ggtgggagac cccaggcctt tctggcagca    60
ggtctggatg gaaagtggac aggaggctca cccgtctgca tcccctgctc ctgcccctgc   120
tcggctacaa aaaccaaagg gacagcagct gaccacaccc ggtagccac tcctgcataa   180
agctctcccc tcctgtgacc agctgaggac ctcaggctgc agcggagcca tgcccagata   240
cacggtgcac gtacgtgggg aatggctggc agtgccctgc caggacgcgc agctcactgt   300
gggctggctg gccggagg ccgtgaggcg ctatatcaag aataagcccg acaatggtgg    360
cttcacctcc gtggatgacg cgcacttcct tgtgcgccgg tgcaagggcc tgggcctgct   420
ggacaacgag gaccggctcg aggtggccct agagaacaac gagttcgtgg aagtggttat   480
agagggtgat gccatgtctc ctgacttcat tccatctcaa ccagaaggag tttatctata   540
cagcaagtac cgggagcctg aaaagtacat cgagttagat ggagaccgtc tgaccacgga   600
ggatctggtc aacttgggaa agggacgcta caaaataaag ctcaccccaa cagctgagaa   660
```

```
gagggtgcag aaatccaggg aggtcataga tagcatcata aaagagaaaa cagttgttta   720
cggtattact acaggttttg ggaaatttgc cagaactgta attcctatca ataagctaca   780
ggagcttcag gtcaacttag tacgctcaca ttcttcaggt gttgggaaac cactaagtcc   840
tgagaggtgt cggatgctct tggctttaag gatcaatgtc ttagccaaag gatacagtgg   900
catttccctg gagaccctca aacaagtcat agaaatgttt aatgcctcct gcctgcccta   960
tgtcccagag aaaggaaccg ttggtgccag tggagacctt gccccactct ctcatcttgc  1020
tcttgggcta gttggagaag ggaagatgtg gtctccgaag agtggctggg ctgatgctaa  1080
atacgtgcta gaagcccatg gattgaaacc agttatttta aaaccaaaag agggcctggc  1140
actcatcaat gggacgcaga tgatcacatc cctgggctgt gaagctgtag agcgagccag  1200
tgctattgca cggcaggctg acattgtggc agccctgacc cttgaggtgc tgaagggcac  1260
caccaaagcc tttgacactg acattcatgc tcttcgacct caccgtgggc aaattgaagt  1320
tgcttttcgg tttcggtcac tcttggactc agatcaccac ccatcagaaa tagcagagag  1380
tcacaggttc tgtgatcgcg tccaggatgc atacaccttg cgctgctgtc cacaggtcca  1440
tggtgtggtg aatgatacaa tagcatttgt gaagaacatc attaccacag aactgaacag  1500
cgcaacagat aatcctatgg tctttgccaa taggggagag acaatttctg gaggaaactt  1560
ccatggtgaa tacccagcca aagccctaga ctacttggcc attggcatcc atgaacttgc  1620
tgcaatcagt gagagaagaa tcgagcggct ctgcaatccc tccctcagtg agctgcctgc  1680
cttcctggtg gctgaaggtg gtctgaactc tgggttcatg atagctcact gcacggcagc  1740
agcccttgtt tctgagaaca aggctctgtg ccatccctcg tctgttgact ccctctccac  1800
cagcgcagcc acgaggacc acgtctccat gggaggatgg gcagcaagga aagccctcag  1860
ggtcatcgag catgtggagc aagtgctggc catcgagctc cttgcagcct gccagggcat  1920
agagtttcta cgtcccctga aaacaaccac tccgctggag aaggtctatg acctggtgcg  1980
ctctgttgta aggccctgga taaaagatcg cttcatggcc ccggacatcg aggcagccca  2040
caggctgctc ctggagcaga aggtttggga agtagctgct ccatacattg aaaaatacag  2100
aatgagcat attccagaat caagacctct ttctccaaca gccttttcac tgcaatttct  2160
gcacaagaaa tccaccaaaa tcccggagtc tgaggaccttt taatgggctt tgtcatgaag  2220
tagcagatga gagggcagtc agtttagcac aaagcaatac taggctgaag gagagacctg  2280
agaactttcc taggtagatc aatccattgt atcattcagt tcttctaaag cctacgttgg  2340
ttaggctgat ggcag                                                    2355

SEQ ID NO: 25        moltype = DNA   length = 3913
FEATURE              Location/Qualifiers
source               1..3913
                     mol_type = genomic DNA
                     organism = Homo sapiens
SEQUENCE: 25
gttttacagt tgagtaatct cagataaaga caggaacatg gtgtttataa gctgccctta    60
atggcagaga acacagacag aaacgaggga agagagagaa attggggacc ctgaagaaag   120
ggggcagca gcaggtaggt gccatcaggg acaagaacag cacctcccag ggtgggagac   180
cccaggcctt tctggcagca ggtctggatg gaaagtggac aggaggctca cccgtctgca   240
tcccctgctc ctgcccctgc tcggctacaa aaaccaaagg gacagcagct gaccacaccc   300
cggtagccac tcctgcataa agctctcccc tcctgtgacc agctgaggac ctcaggctgc   360
agcggagcca tgcccagata cacgtgcaca gtactgtggg aatggctgac agtgccctgc   420
caggacgcgc agctcactgt gggctggctg ggcgggagg ccgtgaggcg ctatatcaag   480
aataagcccg acaatggtgg cttcacctcc gtggatgacg cgcacttcct tgtgcgccgg   540
tgcaagggc tgggcctgct ggacaacgag gaccggctcg aggtggccct agagaacaac   600
gagttcgtgg aagtggttat agagggtgat gccatgtctc ctgacttcat tccatctcaa   660
ccagaaggag tttatctata cagcaagtac cgggagcctg aaaagtacat cgagttagat   720
ggagaccgtc tgaccacgga ggatctggtc aacttgggaa agggacgcta caaaataaag   780
ctcacccca cagctgagaa gagggtgcag aaatccaggg aggtcataga tagcatcata   840
aaagagaaaa cagttgttta cggtattact acaggttttg ggaaatttgc cagaactgta   900
attcctatca ataagctaca ggagcttcag gtcaacttag tacgctcaca ttcttcaggt   960
gttgggaaac cactaagtcc tgagaggtgt cggatgctct tggctttaag gatcaatgtc  1020
ttagccaaag gatacagtgg catttccctg gagaccctca aacaagtcat agaaatgttt  1080
aatgcctcct gcctgcccta tgtcccagag aaaggaaccg ttggtgccag tggagacctt  1140
gccccactct ctcatcttgc tcttgggcta gttggagaag ggaagatgtg gtctccgaag  1200
agtggctggg ctgatgctaa atacgtgcta gaagcccatg gattgaaacc agttatttta  1260
aaaccaaaag agggcctggc actcatcaat gggacgcaga tgatcacatc cctgggctgt  1320
gaagctgtag agcgagccag tgctattgca cggcaggctg acattgtggc agccctgacc  1380
cttgaggtgc tgaagggcac caccaaagcc tttgacactg acattcatgc tcttcgacct  1440
caccgtgggc aaattgaagt tgcttttcgg tttcggtcac tcttggactc agatcaccac  1500
ccatcagaaa tagcagagag tcacaggttc tgtgatcgcg tccaggatgc atacaccttg  1560
cgctgctgtc cacaggtcca tggtgtggtg aatgatacaa tagcatttgt gaagaacatc  1620
attaccacag aactgaacag cgcaacagat aatcctatgg tctttgccaa taggggagag  1680
acaatttctg gaggaaactt ccatggtgaa tacccagcca aagccctaga ctacttggcc  1740
attggcatcc atgaacttgc tgcaatcagt gagagaagaa tcgagcggct ctgcaatccc  1800
tccctcagtg agctgcctgc cttcctggtg gctgaaggtg gtctgaactc tgggttcatg  1860
atagctcact gcacggcagc agcccttgtt tctgagaaca aggctctgtg ccatccctcg  1920
tctgttgact ccctctccac cagcgcagcc acggaggacc acgtctccat gggaggatgg  1980
gcagcaagga aagccctcag ggtcatcgag catgtggagc aagtgctggc catcgagctc  2040
cttgcagcct gccagggcat agagtttcta cgtcccctga aaacaaccac tccgctggag  2100
aaggtctatg acctggtgcg ctctgttgta aggccctgga taaaagatcg cttcatggcc  2160
ccggacatcg aggcagccca caggctgctc ctggagcaga aggtttggga agtagctgct  2220
ccatacattg aaaaatacag aatgagcat attccagaat caagacctct ttctccaaca  2280
gccttttcac tgcaatttct gcacaagaaa tccaccaaaa tcccggagtc tgaggacctt  2340
taatgggctt tgtcatgaag tagcagatga gagggcagtc agtttagcac aaagcaatac  2400
taggctgaag gagagacctg agaactttcc taggtagatc aatccattgt atcattcagt  2460
tcttctaaag cctacgttgg ttaggctgat ggcagtatta tagttgctaa attcagcact  2520
gtgttcctgt tgtcgtggtt caagacccac caggtatttt cagattataa aacttttctt  2580
```

```
                                         -continued
tctttcttaa cagtttcaac aggccactca ctcttaaggg tgagaagaat aaccacaatt    2640
gtatgtgcct gttttttact cttagcatta gatgaattca aatttggaaa cagattgata    2700
gcaattttt  ctaaaaacat tagacttttg ttaacctttt tttttttttt taaatttgct    2760
tcaacaagct ctccaccagt tgactttctt tggctaattt tactttgcat gatatgcctt    2820
aatatgcctt cataaataac catttaagt  cataatttgt ccttaagctg ctttttttct    2880
ctattaattg gatcatagta aagagtagtc aatagggtct tcagctatta attgtagagg    2940
tgattaaaac caacaaggag tttcatgtgc aaaggagata aggaatgaat ataaagattg    3000
ctatttgggt ggctcttatt aaactgtgta ttttgtactt atcactacac gtatccccca    3060
aatgcttaca tgggagtttg aggttagtat tttcacttcc ttggtgttag tactctattc    3120
acattcttat tgtaaccttc ctcatttcac agataaggaa tctttgggga ttaaccaacc    3180
tccttctgt  aatggtaatc attaaaataa gtcctattga taaaggtcag atggagccct    3240
agagtgtatt actgcatcta ttttttttcc cgagaagata aaggaccttc agggatggct    3300
taagtgtatc tgtccagatg aaggatgggt cacatgacct cttggcttcc caagtctaag    3360
ctctgtgact ttgcaccagt gtgtgcatat atgtgcaagg cccttcaagt ggtctgaaac    3420
cgtggctcta aaaaccacag ctggtggaga ggaggacaga cacacttgcc accttgccta    3480
cctaattgcc atctaaaatg ggccgaacag tggattcac  aatagagttt tcacccttta    3540
gatttacaac ctgtcaggtg gaaactgaag tgaaactgc  tgcacacagc aattcaggga    3600
gcaaaaaatg tgctgaggag actgtttacc taaaggttgt tcttggtgct attccttgtc    3660
aaaatgtgaa cacacacaaa tgaggtttgt gcattgtcat ccgtgggctg ccattgagcc    3720
agtaacccc  agtggtctca tggtgctctt cgctccagtt tggggaatgc tggattcttt    3780
cagccctgc  agcctccag  gtcaaaatga cactttgtca ctgagttttc tacacagctc    3840
tattagtaac tgacagcaca cgccttcaag ggaacttcaa gggaaacatg gaataaaacta   3900
agtctcaatt gcc                                                       3913

SEQ ID NO: 26           moltype = AA  length = 657
FEATURE                 Location/Qualifiers
source                  1..657
                        mol_type = protein
                        organism = Homo sapiens
SEQUENCE: 26
MPRYTVHVRG EWLAVPCQDA QLTVGWLGRE AVRRYIKNKP DNGGFTSVDD AHFLVRRCKG    60
LGLLDNEDRL EVALENNEFV EVVIEGDAMS PDFIPSQPEG VYLYSKYREP EKYIELDGDR    120
LTTEDLVNLG KGRYKIKLTP TAEKRVQKSR EVIDSIIKEK TVVYGITTGF GKFARTVIPI    180
NKLQELQVNL VRSHSSGVGK PLSPERCRML LALRINVLAK GYSGISLETL KQVIEMFNAS    240
CLPYVPEKGT VGASGDLAPL SHLALGLVGE GKMWSPKSGW ADAKYVLEAH GLKPVILKPK    300
EGLALINGTQ MITSLGCEAV ERASAIARQA DIVAALTLEV LKGTTKAFDT DIHALRPHRG    360
QIEVAFRFRS LLDSDHHPSE IAESHRFCDR VQDAYTLRCC PQVHGVVNDT IAFVKNIITT    420
ELNSATDNPM VFANRGETVS GGNFHGEYPA KALDYLAIGI HELAAISERR IERLCNPSLS    480
ELPAFLVAEG GLNSGFMIAH CTAAALVSEN KALCHPSSVD SLSTSAATED HVSMGGWAAR    540
KALRVIEHVE QVLAIELLAA CQGIEFLRPL KTTTPLEKVY DLVRSVVRPW IKDRFMAPDI    600
EAAHRLLLEQ KVWEVAAPYI EKYRMEHIPE SRPLSPTAFS LQFLHKKSTK IPESEDL       657

SEQ ID NO: 27           moltype = AA  length = 449
FEATURE                 Location/Qualifiers
source                  1..449
                        mol_type = protein
                        organism = Homo sapiens
SEQUENCE: 27
MLLALRINVL AKGYSGISLE TLKQVIEMFN ASCLPYVPEK GTVGASGDLA PLSHLALGLV    60
GEGKMWSPKS GWADAKYVLE AHGLKPVILK PKEGLALING TQMITSLGCE AVERASAIAR    120
QADIVAALTL EVLKGTTKAF DTDIHALRPH RGQIEVAFRS LLDSDHHP   SEIAESHRFC    180
DRVQDAYTLR CCPQVHGVVN DTIAFVKNII TTELNSATDN PMVFANRGET VSGGNFHGEY    240
PAKALDYLAI GIHELAAISE RRIERLCNPS LSELPAFLVA EGGLNSGFMI AHCTAAALVS    300
ENKALCHPSS VDSLSTSAAT EDHVSMGGWA ARKALRVIEH VEQVLAIELL AACQGIEFLR    360
PLKTTTPLEK VYDLVRSVVR PWIKDRFMAP DIEAAHRLLL EQKVWEVAAP YIEKYRMEHI    420
PESRPLSPTA FSLQFLHKKS TKIPESEDL                                      449

SEQ ID NO: 28           moltype = AA  length = 591
FEATURE                 Location/Qualifiers
source                  1..591
                        mol_type = protein
                        organism = Homo sapiens
SEQUENCE: 28
MPRYTVHVRG EWLAVPCQDA QLTVGWLGRE AVRRYIKNKP DNGGFTSVDD AHFLVRRCKG    60
LGLLDNEDRL EVALENNEFV EVVIEGDAMS PDFIPSQPEG VYLYSKYREP EKYIELDGDR    120
LTTEDLVNLG KGRYKIKLTP TAEKRVQKSR EVIDSIIKEK TVVYGITTGF GKFARTVIPI    180
NKLQELQVNL VRSHSSGVGK PLSPERCRML LALRINVLAK GYSGISLETL KQVIEMFNAS    240
CLPYVPEKGT VGASGDLAPL SHLALGLVGE GKMWSPKSGW ADAKYVLEAH GLKPVILKPK    300
EGLALINGTQ MITSLGCEAV ERASAIARQA DIVAALTLEV LKGTTKAFDT DIHALRPHRG    360
QIEVAFRFRS LLDSDHHPSE IAESHRFCDR VQDAYTLRCC PQVHGVVNDT IAFVKNIITT    420
ELNSATDNPM VFANRGETVS GGNFHGEYPA KALDYLAIGI HELAAISERR IERLCNPSLS    480
ELPAFLVAEG GLNSGFMIAH CTAAALVSEN KALCHPSSVD SLSTSAATED HVSMGGWAAR    540
KALRVIEHVE QVLAIELLAA CQGIEFLRPL KTTTPLEKVY DLVRSVVRFG K             591

SEQ ID NO: 29           moltype = AA  length = 219
FEATURE                 Location/Qualifiers
source                  1..219
                        mol_type = protein
                        organism = Homo sapiens
```

```
SEQUENCE: 29
MAGGNFHGEY PAKALDYLAI GIHELAAISE RRIERLCNPS LSELPAFLVA EGGLNSGFMI   60
AHCTAAALVS ENKALCHPSS VDSLSTSAAT EDHVSMGGWA ARKALRVIEH VEQVLAIELL  120
AACQGIEFLR PLKTTTPLEK VYDLVRSVVR PWIKDRFMAP DIEAAHRLLL EQKVWEVAAP  180
YIEKYRMEHI PESRPLSPTA FSLQFLHKKS TKIPESEDL                        219

SEQ ID NO: 30          moltype = AA  length = 167
FEATURE                Location/Qualifiers
source                 1..167
                       mol_type = protein
                       organism = Homo sapiens
SEQUENCE: 30
MPRYTVHVRG EWLAVPCQDA QLTVGWLGRE AVRRYIKNKP DNGGFTSVDD AHFLVRRCKG   60
LGLLDNEDRL EVALENNEFV EVVIEGDAMS PDFIPSQPEG VYLYSKYREP EKYIELDGDR  120
LTTEDLVNLG KGRYKIKLTP TAEKRVQKSR EVIDSIIKEK TGSFRST                167
```